United States Patent
Hashimoto et al.

(10) Patent No.: US 9,846,120 B2
(45) Date of Patent: Dec. 19, 2017

(54) LIGHT MEASUREMENT APPARATUS, METHOD, PROGRAM AND RECORDING MEDIUM

(71) Applicant: ADVANTEST CORPORATION, Tokyo (JP)

(72) Inventors: Masaichi Hashimoto, Miyagi (JP); Akiyoshi Irisawa, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 359 days.

(21) Appl. No.: 14/427,061

(22) PCT Filed: Aug. 22, 2013

(86) PCT No.: PCT/JP2013/073070
§ 371 (c)(1),
(2) Date: Mar. 10, 2015

(87) PCT Pub. No.: WO2014/045820
PCT Pub. Date: Mar. 27, 2014

(65) Prior Publication Data
US 2015/0241346 A1 Aug. 27, 2015

(30) Foreign Application Priority Data
Sep. 24, 2012 (JP) ................. 2012-210073

(51) Int. Cl.
*G01N 21/59* (2006.01)
*G01N 21/3586* (2014.01)
*G01J 9/00* (2006.01)

(52) U.S. Cl.
CPC ............. *G01N 21/59* (2013.01); *G01J 9/00* (2013.01); *G01N 21/3586* (2013.01)

(58) Field of Classification Search
CPC ........ G01N 21/59; G01N 21/3586; G01J 9/00
(Continued)

(56) References Cited

U.S. PATENT DOCUMENTS

| | | | | |
|---|---|---|---|---|
| 3,722,258 A | * | 3/1973 | Besson ................. | G04F 10/00 368/47 |
| 7,342,651 B1 | * | 3/2008 | Woolfson ............. | G01S 7/484 356/28 |

(Continued)

FOREIGN PATENT DOCUMENTS

| | | |
|---|---|---|
| JP | 2010-002218 | 1/2010 |
| JP | 2011-007590 | 1/2011 |

(Continued)

OTHER PUBLICATIONS

International Search Report from Japan for PCT/JP2013/073070, dated Nov. 5, 2013.

*Primary Examiner* — David Porta
*Assistant Examiner* — Gisselle Gutierrez
(74) *Attorney, Agent, or Firm* — Greenblum & Bernstein, P.L.C.

(57) ABSTRACT

A light measurement apparatus includes a master laser, a slave laser, an illumination light pulse, and a signal-under-measurement generator. The master laser generates as an output a master laser light pulse, and the slave laser generates as an output a slave laser light pulse having a repetition frequency or a phase different from that of the master laser light pulse. The illumination light pulse generator receives the master laser light pulse and generates as an output an illumination light pulse, and the signal-under-measurement generator, at a point in time when receiving a light pulse under measurement obtained by illuminating the object under measurement with the illumination light pulse and further the slave laser light pulse, generates as an output a signal under measurement according to a power of the light pulse under measurement. The apparatus corrects an error in a measurement of the signal under measurement.

10 Claims, 35 Drawing Sheets

(58) Field of Classification Search
USPC .................................................. 250/341.5
See application file for complete search history.

(56) References Cited

U.S. PATENT DOCUMENTS

| | | | |
|---|---|---|---|
| 8,183,528 B2 | 5/2012 | Kato et al. | |
| 8,399,835 B2 | 3/2013 | Hashimoto et al. | |
| 8,481,938 B2 | 7/2013 | Nishina et al. | |
| 8,493,057 B2 | 7/2013 | Nishina et al. | |
| 8,514,399 B2* | 8/2013 | Kajiki | G01J 3/42 |
| | | | 250/341.5 |
| 9,709,497 B2* | 7/2017 | Nakagawa | G01N 21/27 |
| 2003/0197537 A1* | 10/2003 | Saint-Laurent | G06F 1/10 |
| | | | 327/165 |
| 2008/0251740 A1* | 10/2008 | Dilhaire | G01J 11/00 |
| | | | 250/578.1 |
| 2010/0014079 A1 | 1/2010 | Yamashita et al. | |
| 2010/0294934 A1* | 11/2010 | Hashimoto | G01N 21/3581 |
| | | | 250/338.1 |
| 2011/0304853 A1* | 12/2011 | Yamada | H01S 5/0656 |
| | | | 356/479 |
| 2012/0032083 A1 | 2/2012 | Itsuji | |
| 2012/0155500 A1* | 6/2012 | Yamashita | H01S 3/1394 |
| | | | 372/32 |
| 2012/0163404 A1 | 6/2012 | Yamashita et al. | |
| 2012/0286797 A1 | 11/2012 | Kato et al. | |
| 2013/0240736 A1 | 9/2013 | Nishina et al. | |
| 2014/0166883 A1 | 6/2014 | Ono et al. | |
| 2014/0268131 A1* | 9/2014 | Tamada | G01N 21/65 |
| | | | 356/301 |
| 2015/0194786 A1* | 7/2015 | Yamashita | H01S 3/10053 |
| | | | 372/25 |

FOREIGN PATENT DOCUMENTS

| | | |
|---|---|---|
| JP | 4782889 | 7/2011 |
| JP | 4786767 | 7/2011 |
| JP | 2012-037293 | 2/2012 |
| WO | 2010/137536 | 12/2010 |

\* cited by examiner $\Delta Vd1 = \Delta Vd1b + \Delta Vd1m + \Delta Vd1s + \Delta Vd1T$

LIGHT MEASUREMENT APPARATUS, METHOD, PROGRAM AND RECORDING MEDIUM

TECHNICAL FIELD

The present invention relates to measurements of light.

BACKGROUND ART

Methods (refer to Japanese Unexamined Patent Publication No. 2010-2218 (Patent Document 1), and Japanese Unexamined Patent Publication No. 2011-7590 (Patent Document 2) for example) are conventionally known in which a terahertz detector (e.g., photoconductive switch) receives terahertz light A (which is a pulse) that is provided by a terahertz generator (for example, photoconductive switch) to an object under measurement and passes through the object under measurement, and light B of a pulse period slightly different from the pulse period of the terahertz light A, and then the detector measures the object under measurement.

In the above described related arts, a master laser provides a master laser light pulse to the terahertz generator, while a slave laser provides a slave laser light pulse (light B) to the terahertz detector. A repetition frequency of the master laser light pulse, however, is slightly deferent from that of the slave laser light pulse. Note that a technique that causes the repetition frequency of the master laser light pulse to slightly differ from that of the slave laser light pulse is described in Japanese Patent No. 4782889 (Patent Document 3) and Japanese Patent No. 4786767 (Patent Document 4).

Furthermore, a trigger signal is generated on the basis of the master laser light pulse and the slave laser light pulse. The trigger signal serves as a time origin point of a signal detected using the terahertz detector (refer to, for example, Patent Document 1, FIG. 6).

SUMMARY OF THE INVENTION

In the above related arts, however, it is contemplated that ambient temperature changes may cause the lengths of optical paths of the terahertz light A, the slave laser light pulse (light B) and the master laser light pulse to extend and contract. The extension and contraction of the optical path length prevents obtainment of correct information of a lag, relative to the time origin point, of a signal detected using the terahertz detector—i.e., of correct phase information.

Further, in the above related arts, it is contemplated that ambient temperature changes may cause misalignment between optical axes of the terahertz light A, the slave laser light pulse (light B) and the master laser light pulse. Such misalignment of the optical axes results in variations in generation efficiency and detection sensitivity of the terahertz light A. Further, there are also fluctuations in output power from the master laser and the slave laser. Because of this, the amplitude of the signal detected by the terahertz detector cannot in some cases be measured correctly.

Accordingly, it is an object of the present invention to correctly obtain a measurement result (e.g., phase information or amplitude) of an object under measurement by means of light, such as terahertz light.

According to the present invention, a light measurement apparatus that corrects an error in a measurement of a signal under measurement, includes: a master laser that generates as an output a master laser light pulse; a slave laser that generates as an output a slave laser light pulse having a repetition frequency or a phase different from that of the master laser light pulse; an illumination light pulse generator that receives the master laser light pulse and generates as an output an illumination light pulse; and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement.

According to the thus constructed light measurement apparatus, a master laser generates as an output a master laser light pulse. A slave laser generates as an output a slave laser light pulse having a repetition frequency or a phase different from that of the master laser light pulse. An illumination light pulse generator receives the master laser light pulse and generates as an output an illumination light pulse. A signal-under-measurement generator, at a point in time when receiving a light pulse under measurement obtained by illuminating the object under measurement with the illumination light pulse and further the slave laser light pulse, generates as an output the signal under measurement according to a power of the light pulse under measurement. Furthermore, the apparatus corrects an error in a measurement of a signal under measurement.

According to the present invention, the light measurement apparatus may correct an error in measurement at an output point of the signal under measurement.

According to the present invention, the light measurement apparatus may further include: a signal measuring unit that measures the output point of the signal under measurement; a monitor signal generator that receives the illumination light pulse and the slave laser light pulse and generates as an output a monitor signal; a time measuring unit that measures an output point of the monitor signal; a time difference derivation unit that derives a lag between a measurement result obtained by the time measuring unit and a measurement result obtained by the time measuring unit before a point in time when the former measurement result is obtained; and an error correction unit that corrects the output point of the signal under measurement, based on a result derived by the time difference derivation unit, wherein a difference in time between the signal under measurement and the monitor signal may be constant.

According to the present invention, the light measurement apparatus may further include: a trigger signal generator that generates as an output a trigger signal at a point in time when simultaneously receiving the master laser light pulse and the slave laser light pulse, wherein the signal measuring unit measures the output point of the signal under measurement relative to the trigger signal, and wherein the error correction unit corrects an output point of the trigger signal generated from the trigger signal generator.

According to the light measurement apparatus of the present invention, the error correction unit may correct the measurement result obtained by the signal measuring unit.

According to the light measurement apparatus of the present invention, the time measuring unit may measure the monitor signal at a plurality times, and wherein the time difference derivation unit may derive the lag between the measurement result obtained by the time measuring unit and the measurement result obtained at the last time by the time measuring unit.

According to the light measurement apparatus of the present invention, the time difference derivation unit may derive a lag between the measurement result obtained by the time measuring unit and the measurement result obtained at the last time by the time measuring unit, the latter result being a result that has been corrected by the error correction unit.

According to the light measurement apparatus of the present invention, the signal-under-measurement generator may double as the monitor signal generator, and the light pulse under measurement and the illumination light pulse may be received by the signal-under-measurement generator in such a way that both pulses do not overlap with each other in a time domain.

According to the light measurement apparatus of the present invention, the difference in optical path between an optical path where the object under measurement is present and an optical path where the object under measurement is not present, each path being located between the illumination light pulse generator and the signal-under-measurement generator, may be great enough for the signal-under-measurement generator to receive the light pulse under measurement and the illumination light pulse in such a way that both pulses do not overlap with each other in the time domain.

According to the present invention, the light measurement apparatus may include an optical system in which any selected one of the light pulse under measurement and the illumination light pulse is provided to the signal-under-measurement generator.

According to the present invention, the light measurement apparatus may further include a signal measuring unit that measures the output point of the signal under measurement; a time and temperature characteristic recording unit that records a relationship of the output point of the output from the signal-under-measurement generator with respect to an environmental temperature; a time difference derivation unit that derives, based on information recorded by the time and temperature characteristic recording unit, a lag between the output point of the signal under measurement at a reference temperature and the output point of the signal under measurement at an environmental temperature at a point in time when the signal under measurement is measured; and an error correction unit that corrects the output point of the signal under measurement, based on a result derived by the time difference derivation unit.

According to the present invention, the light measurement apparatus may further include a trigger signal generator that generates as an output a trigger signal at a point in time when simultaneously receiving the master laser light pulse and the slave laser light pulse, wherein the signal measuring unit measures the output point of the signal under measurement relative to the trigger signal, and wherein the error correction unit corrects an output point of the trigger signal generated by the trigger signal generator.

According to the light measurement apparatus of the present invention, the error correction unit may correct a measurement result obtained by the signal measuring unit.

According to the light measurement apparatus of the present invention, the signal measuring unit may measure the signal under measurement at a plurality of times, and wherein the reference temperature may be an environmental temperature at a point in time when the signal under measurement was measured at the last time.

According to the present invention, the light measurement apparatus may correct an error in measurement of an amplitude of the signal under measurement.

According to the present invention, the light measurement apparatus may further include a signal measuring unit that measures the amplitude of the signal under measurement; a monitor signal generator that receives the illumination light pulse and the slave laser light pulse and generates as an output a monitor signal; an amplitude measuring unit that measure an amplitude of the monitor signal; a monitor and bias amplitude characteristic recording unit that records a relationship of the amplitude of the monitor signal with respect to a bias voltage applied to the illumination light pulse generator; a correction value derivation unit that derives, based on information recorded by the monitor and bias amplitude characteristic recording unit, a correction value of the bias voltage, the correction value causing the measurement result obtained by the amplitude measuring unit to correspond to the measurement result obtained by the amplitude measuring unit before a point in time when the former result is obtained; and an amplitude error correction unit that corrects an amplitude of the signal under measurement, based on a result derived by the correction value derivation unit.

According to the light measurement apparatus of the present invention, the amplitude error correction unit may vary the bias voltage by the correction value of the bias voltage.

According to the present invention, the light measurement apparatus may further include a device and bias amplitude characteristic recording unit that records a relationship of an amplitude of an output from the signal-under-measurement generator with respect to the bias voltage, wherein, based on information recorded by the device and bias amplitude characteristic recording unit, the amplitude error correction unit corrects a measurement result obtained by the signal measuring unit by a variation value of the amplitude of the signal under measurement, the value corresponding to the correction value of the bias voltage.

According to the light measurement apparatus of the present invention, the amplitude measuring unit may measure the monitor signal at a plurality of times, and the correction value derivation unit may derive the correction value of the bias voltage, based on the measurement result obtained by the amplitude measuring unit and the measuring result obtained at the last time by the amplitude measuring unit.

According to the light measurement apparatus of the present invention, the correction value derivation unit may derive the correction value of the bias voltage, based on the measurement result obtained by the amplitude measuring unit and the measurement result obtained at the last time by the amplitude measuring unit, the latter result being a result that has been corrected by the amplitude error correction unit.

According to the light measurement apparatus of the present invention, the signal-under-measurement generator may double as the monitor signal generator, and the light pulse under measurement and the illumination light pulse may be received by the signal-under-measurement generator in such a way that both pulses do not overlap with each other in a time domain.

According to the light measurement apparatus of the present invention, the difference in optical path between an optical path where the object under measurement is present and an optical path where the object under measurement is not present, each path being located between the illumination light pulse generator and the signal-under-measurement generator, may be great enough for the signal-under-measurement generator to receive the light pulse under measurement and the illumination light pulse in such a way that both pulses do not overlap with each other in the time domain.

According to the present invention, the light measurement apparatus may further include an optical system in which any selected one of the light pulse under measurement and the illumination light pulse is provided to the signal-under-measurement generator.

According to the present invention, the light measurement apparatus may further include a signal measuring unit that measures the amplitude of the signal under measurement; a device amplitude characteristic recording unit that records a relationship of the amplitude of an output from the signal-under-measurement generator with respect to an amplitude variation factor including any one or more of a bias voltage applied to the illumination light pulse generator, a power of the master laser light pulse, and a power of the slave laser light pulse and an environmental temperature; an amplitude error derivation unit that derives an error in an amplitude of the signal under measurement between a reference amplitude variation factor and a measured amplitude variation factor at a point in time when the signal under measurement is measured, based on information recorded by the device amplitude characteristic recording unit; and an amplitude error correction unit that corrects an amplitude of the signal under measurement, based on a result derived by the amplitude error derivation unit.

According to the present invention, the light measurement apparatus may further include a device and bias amplitude characteristic recording unit that records a relationship of an amplitude of an output from the signal-under-measurement generator with respect to the bias voltage; and a correction value derivation unit that derives, based on information recorded by the device and bias amplitude characteristic recording unit, a correction value of the bias voltage required to vary the amplitude of the signal under measurement by a value that cancel an derived error in the amplitude of the signal under measurement, wherein the amplitude error correction unit varies the bias voltage by the correction value of the bias voltage.

According to the light measurement apparatus of the present invention, the amplitude error correction unit may correct the measurement result obtained by the signal measuring unit, by a value required to cancel an derived error in the amplitude of the signal under measurement.

According to the light measurement apparatus of the present invention, the signal measuring unit may measure the signal under measurement at a plurality of times, and the reference amplitude variation factor may be a measurement amplitude variation factor at a point in time when the signal under measurement was measured at the last time.

The present invention is a method of measuring light with using a light measurement apparatus including; a master laser that generates as an output a master laser light pulse; a slave laser that generates as an output a slave laser light pulse having a repetition frequency or a phase different from that of the master laser light pulse; an illumination light pulse generator that receives the master laser light pulse and generates as an output an illumination light pulse; and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement, the method including; a correcting step that corrects an error in a measurement of a signal under measurement.

The present invention is a program of instructions for execution by a computer to perform a process for measuring light with using a light measurement apparatus including; a master laser that generates as an output a master laser light pulse; a slave laser that generates as an output a slave laser light pulse having a repetition frequency or a phase different from that of the master laser light pulse; an illumination light pulse generator that receives the master laser light pulse and generates as an output an illumination light pulse; and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement, the process including: a correcting step that corrects an error in a measurement of a signal under measurement.

The present invention is a computer-readable medium having a program of instructions for execution by a computer to perform a process for measuring light with using a light measurement apparatus including: a master laser that generates as an output a master laser light pulse; a slave laser that generates as an output a slave laser light pulse having a repetition frequency or a phase different from that of the master laser light pulse; an illumination light pulse generator that receives the master laser light pulse and generates as an output an illumination light pulse; and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement, the process including: a correcting step that corrects an error in a measurement of a signal under measurement.

MODES FOR CARRYING OUT THE INVENTION

In the following, preferred embodiment of the present invention will be described with reference to the accompanying drawings.

First Embodiment

Light measurement apparatuses 1 according to a first embodiment through a fourth embodiment each measure a time of a signal under measurement relative to a trigger signal.

Figure 1:
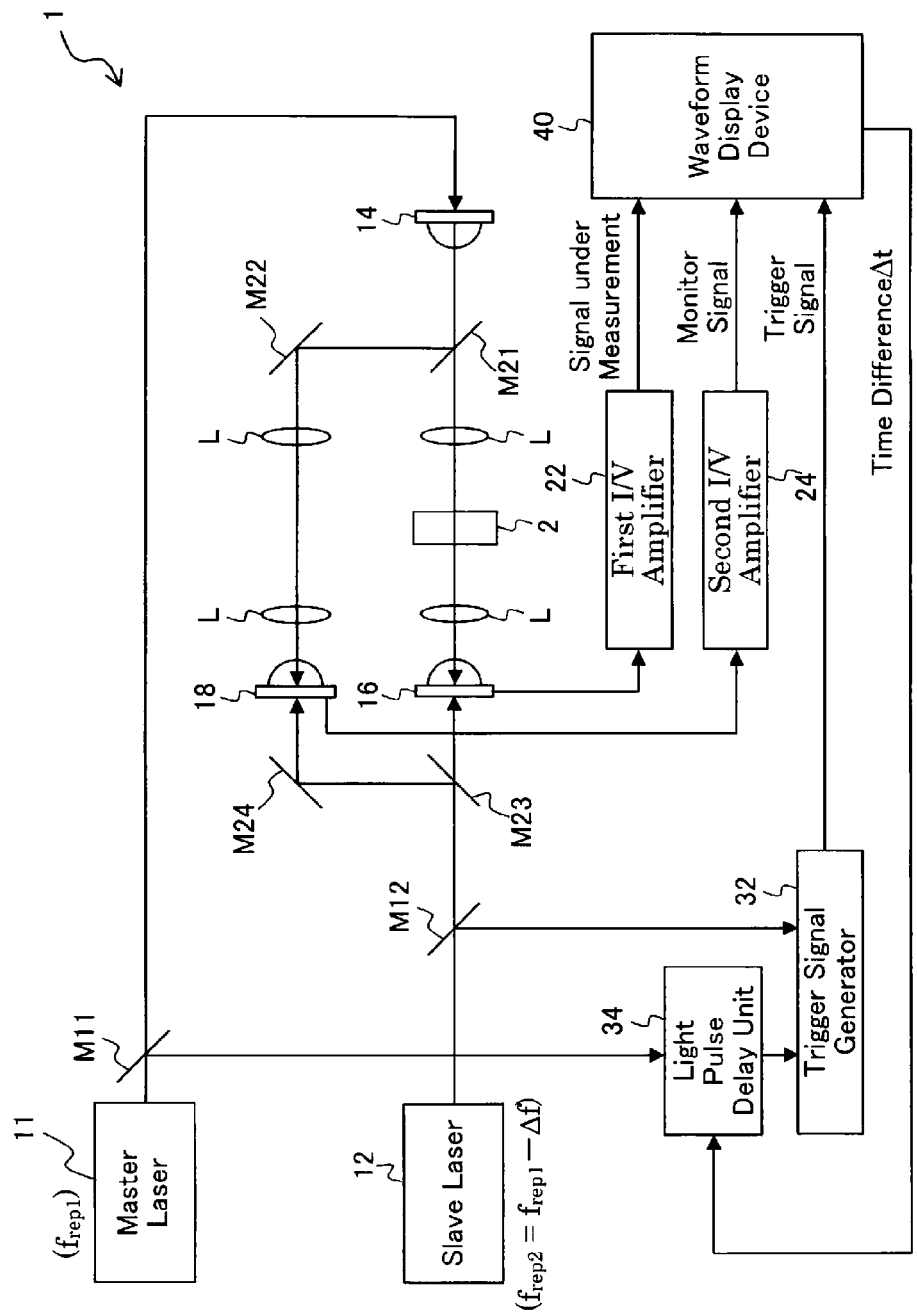
FIG. 1 is a diagram showing a configuration of the light measurement apparatus 1 according to the first embodiment of the present invention.

FIG. 1 is a diagram showing a configuration of the light measurement apparatus 1 according to the first embodiment of the present invention. The light measurement apparatus 1 according to the first embodiment includes a master laser 11, a slave laser 12, half mirrors M11, M12, M21 and M23, mirrors M22, M24, a lens L, an illumination light pulse generator 14, a signal-under-measurement generator 16, a monitor signal generator 18, a first I/V amplifier 22, a second I/V amplifier 24, a trigger signal generator 32, a light pulse delay unit (error correction unit) 34, and a waveform display device 40. The light measurement apparatus 1 according to the first embodiment is a device that measures an object under measurement 2.

Note that the half mirrors M11, M12, M21 and M23 are merely examples, and any suitable devices other than half mirrors may be used that can cause separation of a light beam.

The master laser 11 generates as an output a master laser light pulse. A repetition frequency of the master laser light pulse is $f_{rep1}$. The frequency $f_{rep1}$ is in the order of, e.g., 50 MHz. The master laser light pulse is separated by the half mirror M11 into light that is to be provided to the light pulse delay unit 34 and light that is to be provided to the illumination light pulse generator 14.

The slave laser 12 generates as an output a slave laser light pulse having a repetition frequency different from that of the master laser light pulse. The repetition frequency of the slave laser light pulse is represented as $f_{rep2}$ ($=f_{rep1}-\Delta f$), where $\Delta f$ is not zero. The frequency $\Delta f$ is a value of approximately 1 kHz or less (e.g., the order of 5 Hz). Note that even if the slave laser light pulse has the same repetition frequency as that of the master laser light pulse, it will suffice if the slave pulse has a different phase from that of the master pulse. It will suffice if a phase shift between the slave laser light pulse and the master laser light pulse is caused to vary with time, for example.

The slave laser light pulse is separated by the half mirror M12 into light that is to be provided to the trigger signal generator 32, and light that is to be provided to the signal-under-measurement generator 16 and the monitor signal generator 18. The light that is to be provided to the signal-under-measurement generator 16 and the monitor signal generator 18 is further separated by the half mirror M23 into light that is to be provided to the signal-under-measurement generator 16 and light that is to be provided to the monitor signal generator 18. The light that is to be provided to the monitor signal generator 18 is reflected from the mirror M24 and then provided to the monitor signal generator 18.

The illumination light pulse generator 14 receives the master laser light pulse and generates as an output an illumination light pulse. The illumination light pulse generator 14 is, for example, a photoconductive switch, and a bias voltage is applied to this switch. The illumination light pulse is, for example, an electromagnetic wave having a frequency of 0.01 [THz] or more and 100 [THz] or less, and the light pulse is contemplated to be a terahertz wave (for example, its frequency is 0.03 [THz] or more and 10 [THz] or less).

The illumination light pulse is separated by the half mirror M21 into the light that is to be provided to the signal-under-measurement generator 16 and the light that is to be provided to the monitor signal generator 18.

The illumination light pulse which is provided to the signal-under-measurement generator 16 is directed to the object under measurement 2 while being focused by the lens L. An illumination light pulse that has been passed through the object under measurement 2 (a light pulse under measurement) is provided to the signal-under-measurement generator 16 while being focused by the lens L.

The illumination light pulse which is provided to the monitor signal generator 18 is reflected from the mirror M22 and provided to the monitor signal generator 18 while being further focused by two lenses L.

The signal-under-measurement generator 16 receives a light pulse under measurement obtained by illuminating the object under measurement 2 with an illumination light pulse. The signal-under-measurement generator 16, at a point in time when receiving the light pulse under measurement and further a slave laser light pulse, generates as an output a signal under measurement according to the power of the light pulse under measurement. The signal-under-measurement generator 16 is a photoconductive switch, for example.

The monitor signal generator 18 receives the illumination light pulse and the slave laser light pulse, and generates as an output a monitor signal. The monitor signal generator 18 serves as, e.g., a photoconductive switch.

The first I/V amplifier 22, while amplifying the signal under measurement (which is a current signal) generated as an output by the signal-under-measurement generator 16, converts the signal into a voltage signal, and provides the voltage signal to the waveform display device 40.

The second I/V amplifier 24, while amplifying the monitor signal (which is a current signal) generated as an output by the monitor signal generator 18, converts the signal into a voltage signal, and provides the voltage signal to the waveform display device 40.

The trigger signal generator 32 generates an output trigger signal at a point in time when simultaneously receiving the master laser light pulse and the slave laser light pulse. Note, however, that the trigger signal generator 32 receives the master laser light pulse via the light pulse delay unit 34, and the trigger signal is provided to the waveform display device 40.

The trigger signal generator 32 includes, for example, an optical coupler that generates as an output a light pulse at a point in time when simultaneously receiving the master laser light pulse and the slave laser light pulse, and a photodetector that performs photoelectric conversion of the output from the optical coupler to generate an output trigger signal, which is an electrical signal.

The light pulse delay unit (error correction unit) 34 receives a master laser light pulse from the half mirror M11, delays the received pulse and provides the delayed pulse to the trigger signal generator 32. Note that the light pulse delay unit 34 varies the time that causes the master laser light pulse to be delayed by a time difference $\Delta t$ received from a time difference derivation unit 48 of the waveform display device 40. Note again that the light pulse delay unit 34 may delay the slave laser light pulse rather than the master laser light pulse, and further may receive a trigger signal and delay the pulse. In any cases, the light pulse delay unit 34 corrects by the time difference $\Delta t$ an output point of the trigger signal generated from the trigger signal generator 32 (refer to FIG. 4(*c*) and FIG. 5(*c*)). Based on the result (time difference $\Delta t$) derived by the time difference derivation unit 48, the light pulse delay unit 34 thereby corrects the output point of the signal under measurement resulting from the output point of the trigger signal being set at a time-origin point.

The waveform display device 40 displays a waveform of the signal under measurement.

Figure 2:
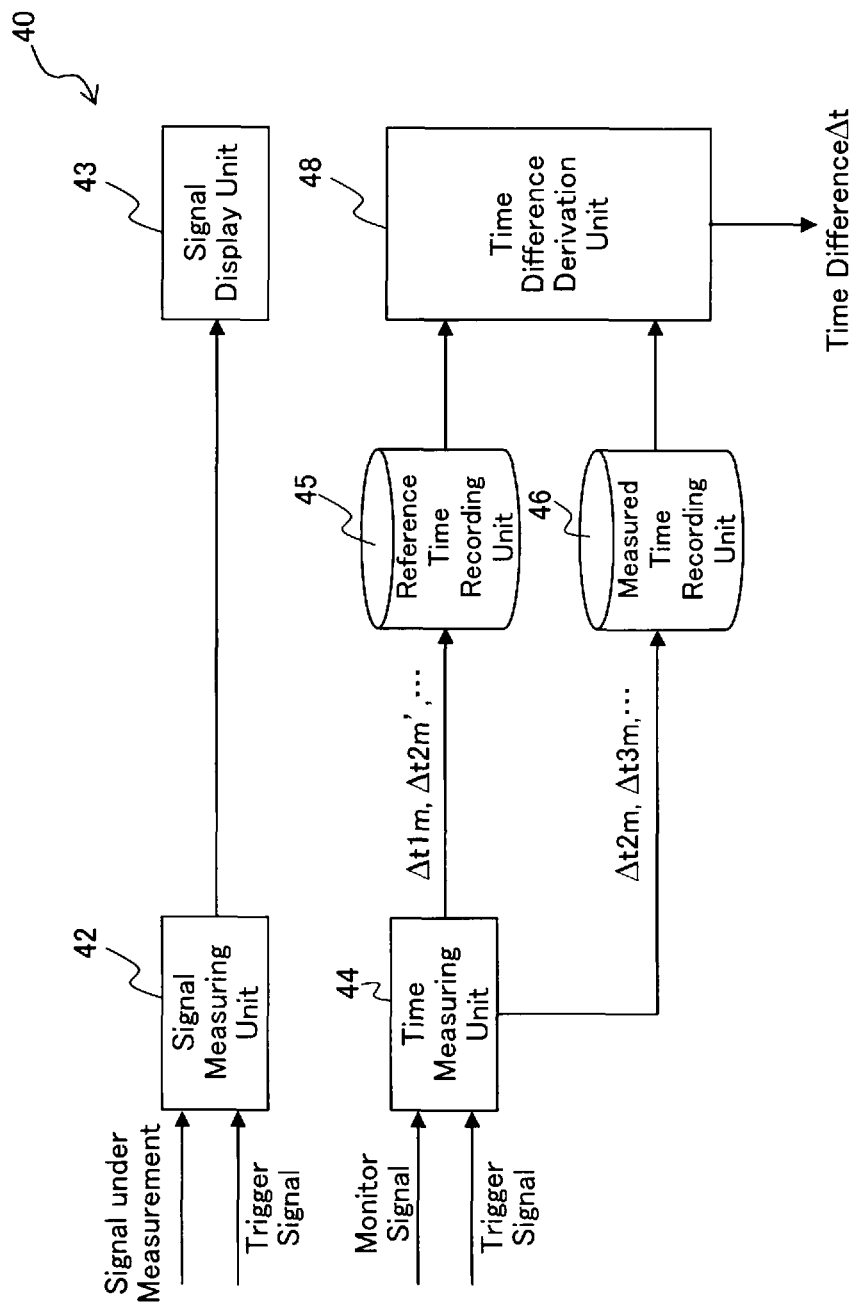
FIG. 2 is a functional block diagram showing a configuration of the waveform display device 40 according to the first embodiment.

FIG. 2 is a functional block diagram showing a configuration of the waveform display device 40 according to the first embodiment. The waveform display device 40 according to the first embodiment has a signal measuring unit 42, a signal display unit 43, a time measuring unit 44, a reference time recording unit 45, a measured time recording unit 46, and the time difference derivation unit 48.

The signal measuring unit 42 receives a signal under measurement and a trigger signal, and measures an output point of the signal under measurement relative to the trigger signal (it will suffice if, for example, the output start point is a point between the start and the end of the output). Add to this, the signal measuring unit 42 measures voltage of the signal under measurement with the voltage associated with a time relative to the trigger signal.

The signal display unit 43 displays a measurement result obtained by the signal measuring unit 42, and the displayed result is a waveform of the signal under measurement.

The time measuring unit 44 measures an output point (e.g., output start point) of the monitor signal at a plurality of times.

Figure 4:
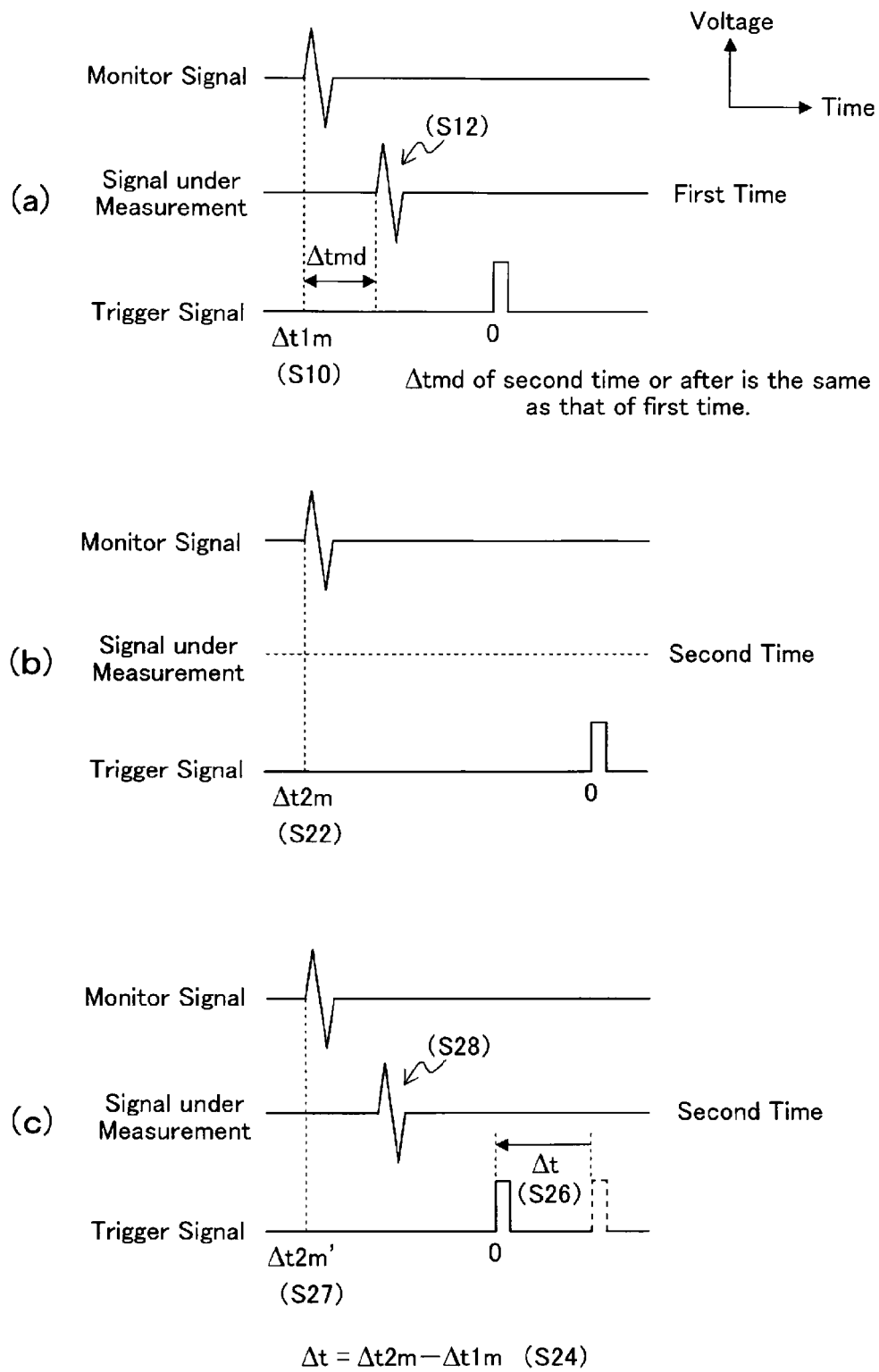
FIG. 4 is a set of time charts for a monitor signal, a signal under measurement, and a trigger signal, at the first time and second time measurements.
Figure 5:
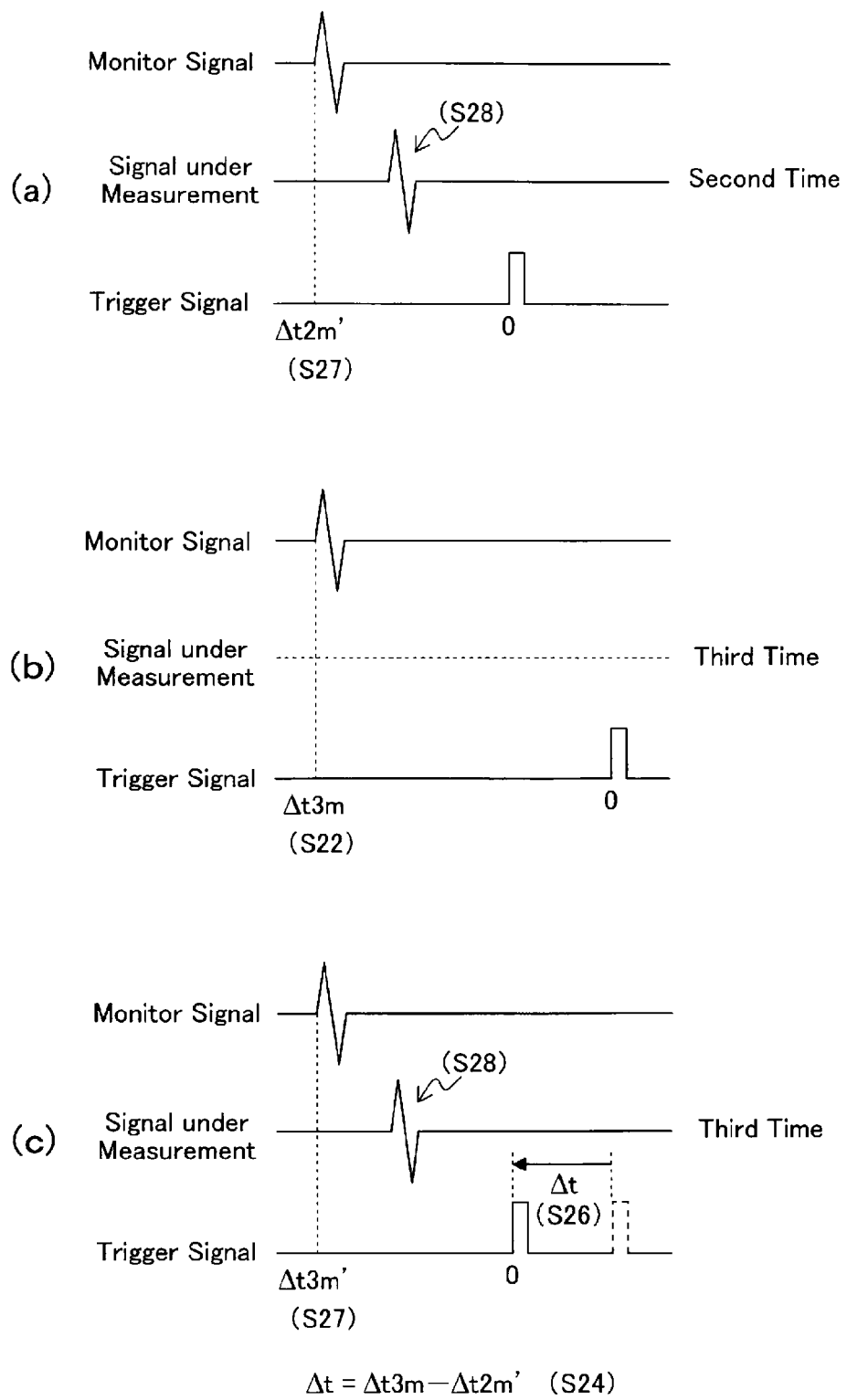
FIG. 5 is a set of time charts for a monitor signal, a signal under measurement, and a trigger signal, at the second time and the third time measurement.

The measured time recoding unit 46 records measurement results (e.g., output start point for a monitor signal, $\Delta t2m$, $\Delta t3m$) obtained by the time measuring unit 44 (refer to FIG. 4(*b*) and FIG. 5(*b*)).

The reference time recording unit 45 records measurement results (e.g., output start points of a monitor signal, $\Delta t1m$, $\Delta t2m'$) obtained by the time measuring unit 44 before a point in time when the measurement result obtained by the time measuring unit 44 (what is recorded in the measured time record unit 46) is acquired (refer to FIG. 4(*a*) and FIG. 5(*a*)).

For example, the measured time recording unit 46 records a measurement result $\Delta t2m$ at the second time of the output start point of the monitor signal, and the reference time recording unit 45 records a measurement result $\Delta t1m$ at the first time of the output start point of the monitor signal (refer to FIG. 4(*b*) and FIG. 4(*a*)).

For example, the measured time recording unit 46 records a measurement result $\Delta t3m$ at the third time of the output start point of the monitor signal, and the reference time recording unit 45 records a measurement result $\Delta t2m'$ at the second time of the output start point of the monitor signal (refer to FIG. 5(b) and FIG. 5(a)).

The time difference derivation unit 48 derives a lag between the measurement result (information recorded by the measured time recording unit 46) obtained by the time measuring unit 44 and the measurement result (information recorded by the reference time recording unit 45) obtained by the time measuring unit 44 before a point in time when the former measurement result is obtained.

For example, the time difference derivation unit 48 derives a lag $\Delta t$ ($=\Delta t2m-\Delta t1m$, $\Delta t3m-\Delta t2m'$) between the measurement result (information recorded by the measured time recording unit 46, $\Delta t2m$, $\Delta t3m$) obtained by the time measuring unit 44 and the last time result (information recorded by the reference time recording unit 45, $\Delta t1m$. $\Delta t2m'$) obtained by the time measuring unit 44 (refer to FIG. 4(c) and FIG. 5(c)).

For example, the time difference derivation unit 48 derives a lag $\Delta t$ ($=\Delta t3m-\Delta t2m'$) between the measurement result (information recorded by the measured time recording unit 46, $\Delta t3m$) obtained by the time measuring unit 44 and the last time measurement result obtained by the time measuring unit 44 which is a measurement result (information recorded by the reference time recording unit 45, $\Delta t2m'$) that has been corrected by the light pulse delay unit (error correction unit) 34 (refer to FIG. 5(c)).

The operation of the first embodiment will next be described.

Figure 3:
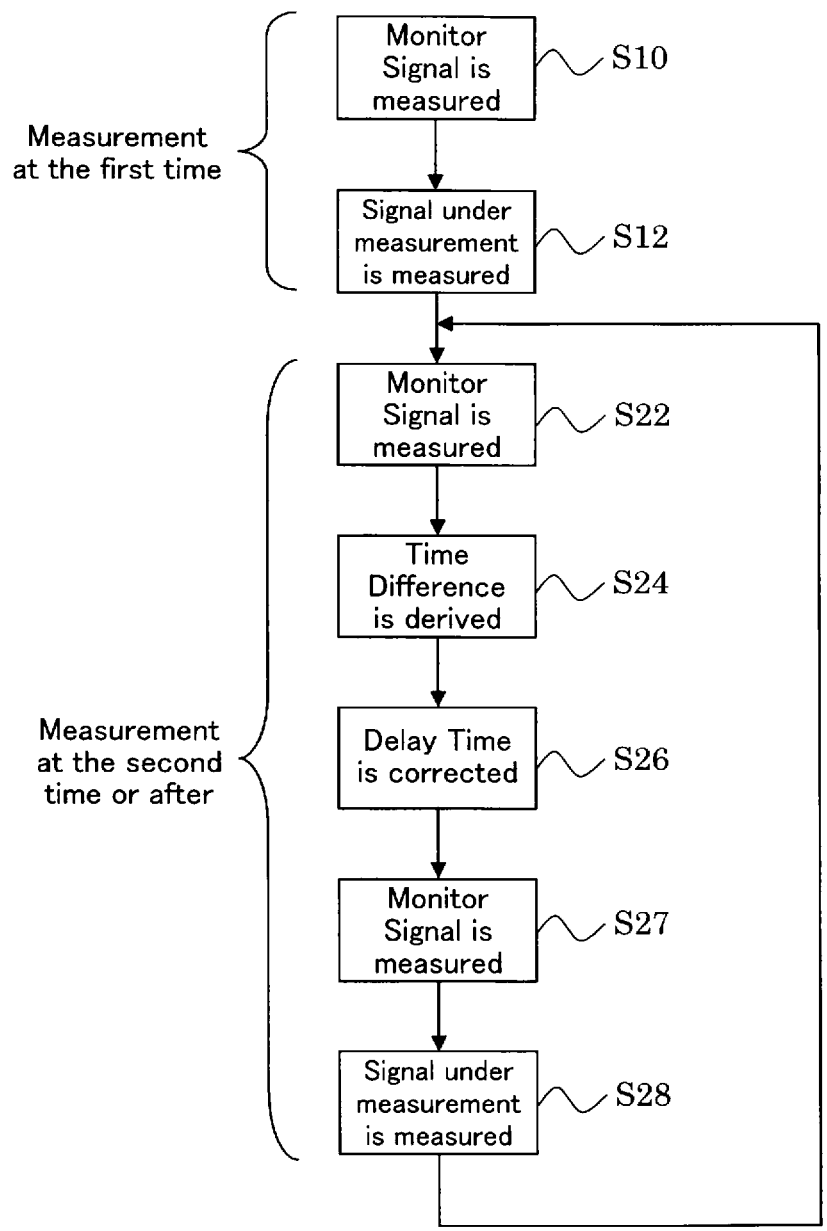
FIG. 3 is a flow chart showing the operation of the first embodiment.

FIG. 3 is a flow chart showing the operation of the first embodiment. FIG. 4 is a set of time charts for a monitor signal, a signal under measurement, and a trigger signal, at the first time and second time measurements. FIG. 5 is a set of time charts for a monitor signal, a signal under measurement, and a trigger signal, at the second time and the third time measurement. Note that in FIGS. 4 and 5, the vertical axis represents voltage and the horizontal axis, time (the same applied to FIG. 7).

A master laser light pulse generated as an output from the master laser 11 is provided via the half mirror M11 to the illumination light pulse generator 14. An illumination light pulse is generated as an output from the illumination light pulse generator 14. The illumination light pulse passes through the half mirror M21 and further through the object under measurement 2, and then becomes a light pulse under measurement, which is provided to the signal-under-measurement generator 16. Moreover, the illumination light pulse is reflected from the half mirror M21 and further from the mirror M22, and then provided to the monitor signal generator 18.

In addition, a slave laser light pulse generated as an output from the slave laser 12 is provided via the half mirrors M12, M23 to the signal-under-measurement generator 16. The slave laser light pulse passes through the half mirror M12, and is reflected from the half mirror M23 and the half mirror M24 and then provided to the monitor signal generator 18.

A signal under measurement (which is a current signal) is generated as an output from the signal-under-measurement generator 16, and converted, while being amplified by the first I/V amplifier 22, into a voltage signal, which is provided to the waveform display device 40. A monitor signal (which is a current signal) is generated as an output from the monitor signal generator 18 and is converted, while being amplified by the second I/V amplifier 24, into a voltage signal, which is provided to the waveform display device 40.

Note that the master laser light pulse and the slave laser light pulse are reflected from the half mirrors M11, M12, respectively, and are provided to the trigger signal generator 32, however, with the master laser light pulse being provided via the light pulse delay unit 34 to the trigger signal generator 32. Note again that the trigger signal generator 32 generates a trigger signal at a point in time when simultaneously receiving the master laser pulse and the slave laser light pulse, and that the trigger signal is provided to the waveform display device 40.

FIG. 4(a) is a time chart for a monitor signal, a signal under measurement and a trigger signal, at the first time measurement. The signal under measurement and the trigger signal are provided to the signal measuring unit 42, and the monitor signal and the trigger signal are provided to the time measuring unit 44.

Here, referring to FIG. 3 and FIG. 4(a), the time measuring unit 44 measures an output point (e.g., the output start point $\Delta t1m$) of a monitor signal relative to a trigger signal (S10: measurement at the first time). Further, the signal measuring unit 42 measures an output point (e.g., output start point) of a signal under measurement relative to a trigger signal, and voltage of the signal under measurement (S12: measurement at the first time).

The measurement result ($\Delta t1m$) obtained by the time measuring unit 44 is recorded in the reference time recording unit 45. The measurement result obtained by the signal measuring unit 42 is displayed on the signal display unit 43.

Note that the time difference $\Delta tmd$ between the output start point of the monitor signal and that of the signal under measurement is assumed to be constant. The conditions that the time difference $\Delta tmd$ are constant are that the difference is constant (preferably zero) between the optical path length from the illumination light pulse generator 14 to the signal-under-measurement generator 16 and that from the illumination light pulse generator 14 to the monitor signal generator 18, and further that the difference is constant (preferably zero) between the optical path length from the half mirror M23 to the signal-under-measurement generator 16 and that from the half mirror M23 to the monitor signal generator 18.

FIG. 4(b) is a time chart for a monitor signal and a trigger signal at the second time measurement. After a certain period of time has elapsed after the signal under measurement has been measured (S12: measurement at the first time), the time measuring unit 44 measures an output point (e.g., output start point $\Delta t2m$) of a monitor signal relative to a trigger signal (S22: measurement at the second time).

Here, the measurement result $\Delta t1m$ at the first time of the output start point of the monitor signal is different from the measurement result $\Delta t2m$ at the second time thereof. This is thought to result from the fact that the change of the ambient temperature (environmental temperature) of the light measurement apparatus 1 at the first and second time measurements causes extensions and contractions of the optical path lengths of the master laser light pulse, the slave laser light pulse, and the illumination light pulse. From the fact that the measurement error of the monitor signal is $\Delta t2m-\Delta t1m$, and the time $\Delta tmd$ between the monitor signal and the signal under measurement is constant, it can be mentioned that the measurement error in the output point of the signal under measurement is also $\Delta t2m-\Delta t1m$.

The measurement result $\Delta t2m$ at the second time obtained by the time measuring unit 44 is recorded in the measured time recording unit 46.

FIG. 4(c) is a time chart for a monitor signal, a signal under measurement, and a trigger signal, at the second time measurement. The time difference derivation unit 48 derives a lag (time difference) $\Delta t$ ($=\Delta t2m-\Delta t1m$) between a measurement result (information recorded by the measured time recording unit 46, Δt2m) at the second time obtained by the time measuring unit 44 and a measurement result (information recorded by the reference time recording unit 45, Δt1m) at the first time obtained by the time measuring unit 44 (S24).

The time difference Δt generated as an output from the time difference derivation unit 48 is provided to the light pulse delay unit (error correction unit) 34. The light pulse delay unit 34 shifts the master laser light pulse by the time difference Δt (S26). As a result of this, the trigger signal is shifted by the time difference Δt, thereby correcting the error in the measurement of the output points of the monitor signal and the signal under measurement.

Here, the time measuring unit 44 measures an output point (e.g., output start point Δt2m') of the monitor signal relative to the trigger signal (S27: measurement at the second time). The point Δt2m' is substantially equal to Δt1m, and is recorded in the reference time recording unit 45. Further, the signal measuring unit 42 measures an output point (e.g., output start point) of the signal under measurement relative to the trigger signal, and voltage of the signal under measurement (S28: measurement at the second time).

Further, after a certain period of time has elapsed after measuring the signal under measurement (S27: measurement at the second time), the time measuring unit 44 measures an output point (e.g., output start point Δt3m) of a monitor signal relative to a trigger signal (S22: measurement at the third time).

FIG. 5(a) is a time chart for a monitor signal, a signal under measurement, and a trigger signal, at the second time measurement. FIG. 5(b) is a time chart for a monitor signal, and a trigger signal, at the third time measurement.

Here, the measurement result Δt2m' (measurement result wherein the measurement error has been corrected by the light pulse delay unit 34) at the second time of output start point of the monitor signal is different from the measurement result Δt3m at the third time thereof. This is thought to result from the fact that the change of the ambient temperature (environmental temperature) of the light measurement apparatus 1 at the second and third time measurements has caused the optical path lengths of the master laser light pulse, the slave laser light pulse, and the illumination light pulse to extend and contract. From the fact that the measurement error of the monitor signal is Δt3m−Δt2m', and the time Δtmd between the monitor signal and the signal under measurement is constant, it can be mentioned that the measurement error of the signal under measurement is also Δt3m−Δt2m'.

The measurement result Δt3m at the third time obtained by the time measuring unit 44 is recorded in the measured time recording unit 46.

FIG. 5(c) is a time chart for a monitor signal, a signal under measurement, and a trigger signal, at the third time measurement. The time difference derivation unit 48 derives a lag (time difference) Δt (=Δt3m−Δt2m') between a measurement result (information recorded by the measured time recording unit 46, Δt3m) at the third time obtained by the time measuring unit 44 and a measurement result (information recorded by the reference time recording unit 45, Δt2m') at the second time obtained by the time measuring unit 44 (S24).

The time difference Δt generated as an output from the time difference derivation unit 48 is provided to the light pulse delay unit (error correction unit) 34. The light pulse delay unit 34 shifts the master laser light pulse by the time difference Δt (S26). As a result of this, the trigger signal is shifted by the time difference Δt, thereby correcting the error in the measurement of the output points of the monitor signal and the signal under measurement.

Here, the time measuring unit 44 measures an output point (e.g., output start point Δt3m') of the monitor signal relative to the trigger signal (S27: measurement at the third time). The point Δt3m' is substantially equal to Δt2m'. The point Δt2m' is substantially equal to Δt1m, thereby resulting in the point Δt3m' being substantially equal to Δt1m. The point Δt3m' is recorded in the reference time recording unit 45. Further, the signal measuring unit 42 measures an output point (e.g., output start point) of the signal under measurement relative to the trigger signal, and voltage of the signal under measurement (S28: measurement at the third time).

According to the first embodiment, the time difference derivation unit 48 derives an error in the measurement result (output point) of the object under measurement 2 by means of light, such as terahertz light (illumination light pulse)— the error resulting from the changed ambient temperature (environmental temperature) of the light measurement apparatus 1, and then the light pulse delay unit 34 corrects the error—as a result, the phase information in the measurement result of the object under measurement 2 can be obtained correctly.

Figure 10:
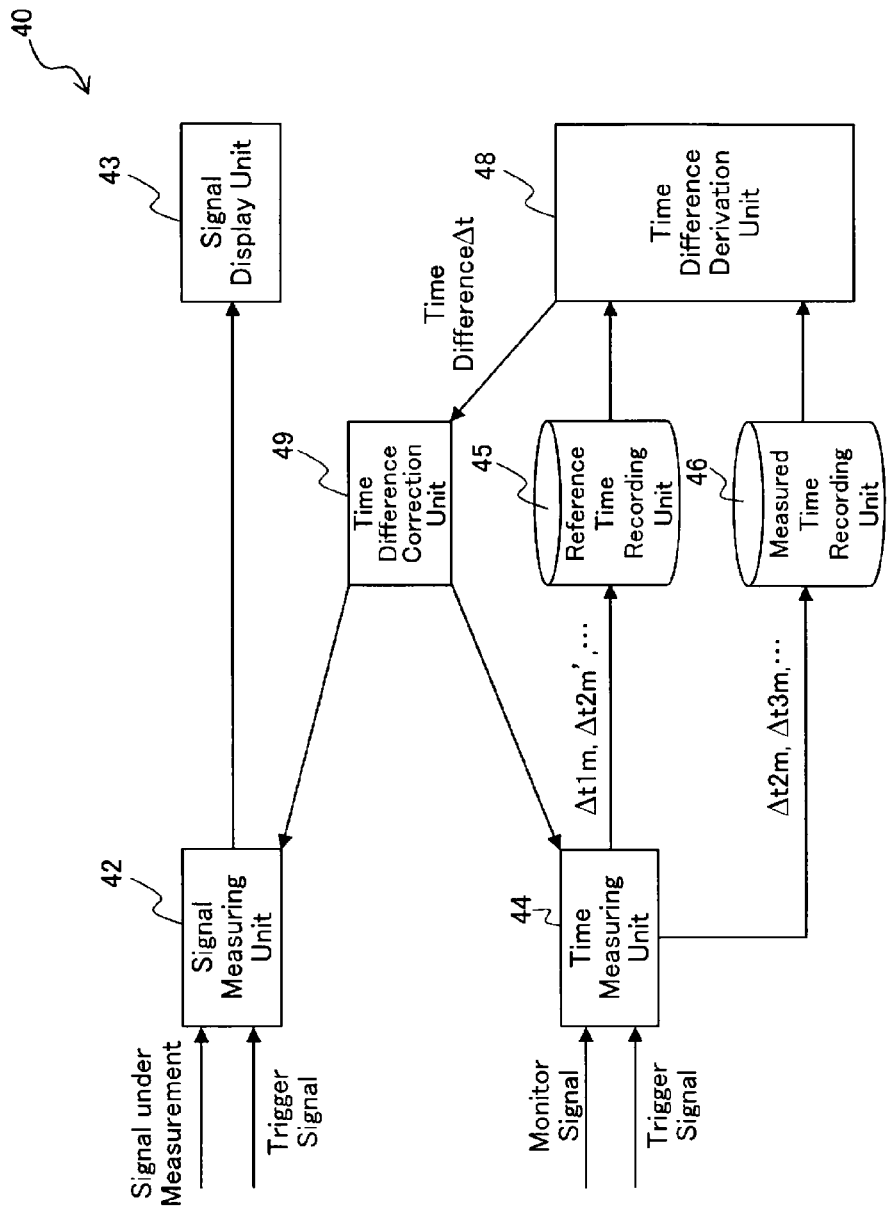
FIG. 10 is a functional block diagram showing a configuration of the waveform display device 40 according to a modification (where error correction is made without using the light pulse delay unit 34) of the first embodiment.

Note that although in the first embodiment the light pulse delay unit 34 has shifted the trigger signal by Δt to correct the error, error correction can also be made without using the light pulse delay unit 34. FIG. 10 is a functional block diagram showing a configuration of the waveform display device 40 according to a modification (where error correction is made without using the light pulse delay unit 34) of the first embodiment.

The waveform display device 40 according to the modification of the first embodiment is configured to further add a time difference correction unit (error correction unit) 49 to the waveform display device 40 according to the first embodiment.

The time difference derivation unit 48 in the waveform display device 40 according to the modification of the first embodiment provides the derived time difference Δt not to the light pulse delay unit 34, but to the time difference correction unit 49. The time difference correction unit 49 provides the time difference Δt to the signal measuring unit 42 and the time measuring unit 44, to shift times of the signal under measurement and the monitor signal by −Δt in the signal measuring unit 42 and the time measuring unit 44. Note that should measurement results obtained by the signal measuring unit 42 and the time measuring unit 44 be assumed to be generated as output digital data, it will suffice if the measuring units vary by −Δt the data of time in the digital data and thereafter generate as an output the changed data. In this way, the measurement results obtained by the signal measuring unit 42 are corrected.

Second Embodiment

The light measurement apparatus 1 according to the second embodiment differs from the apparatus 1 of the first embodiment in that the signal-under-measurement generator 16 doubles as a monitor signal generator.

Figure 6:
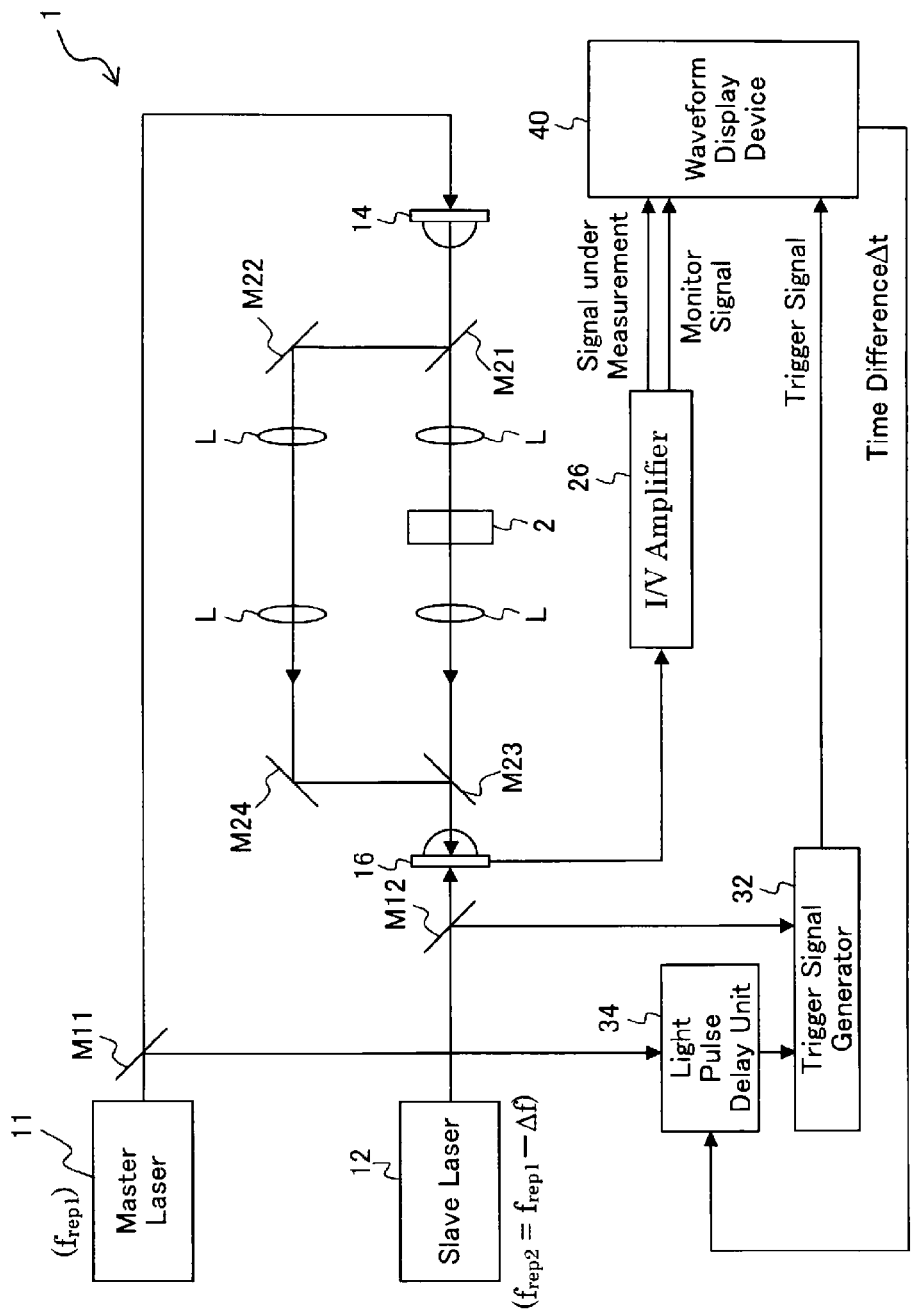
FIG. 6 is a diagram showing a configuration of the light measurement apparatus 1 according to the second embodiment of the present invention.

FIG. 6 is a diagram showing a configuration of the light measurement apparatus 1 according to the second embodiment of the present invention. The light measurement apparatus 1 according to the second embodiment includes the master laser 11, the slave laser 12, the half mirrors M11, M12, M21 and M23, the mirrors M22, M24, the lens L, the illumination light pulse generator 14, the signal-under-measurement generator 16, an I/V amplifier 26, the trigger signal generator 32, the light pulse delay unit (error correction unit) 34, and the waveform display device 40. Elements similar to the first embodiment are designated hereinafter with the same reference numerals as those of the first embodiment, and their description will not be provided herein.

The master laser 11, the slave laser 12, the half mirrors M11, M12, the lens L, the illumination light pulse generator 14, the trigger signal generator 32, the light pulse delay unit (error correction unit) 34, and the waveform display device 40, are the same as those in the first embodiment and thus, their description will not be provided.

A slave laser light pulse generated as an output from the slave laser 12 passes through the half mirror M12 and is provided to the signal-under-measurement generator 16.

An illumination light pulse is separated by the half mirror M21 into light to be directed toward the object under measurement 2 and light not to be directed theretoward. The former (light to be directed toward the object under measurement 2) passes through the object under measurement 2 (light pulse under measurement), and is provided to the signal-under-measurement generator 16. The signal-under-measurement generator 16 receives the light pulse under measurement and generate as an output a signal under measurement. The latter (light not to be directed toward the object under measurement 2: illumination light pulse) is reflected from the mirrors M22, M24 and the half mirror M23, and then provided to the signal-under-measurement generator 16. The signal-under-measurement generator 16 receives the latter (illumination light pulse) and generates as an output a monitor signal.

In this way, the signal-under measurement generator 16 generates as an output a signal under measurement, and also a monitor signal. In other words, the signal-under-measurement generator 16 doubles as a monitor signal generator.

While amplifying the signal under measurement and the monitor signal generated as an output from the signal-under-measurement generator 16, the I/V amplifier 26 converts the amplified signals into voltage signals, which are provided to the waveform display device 40.

Figure 7:
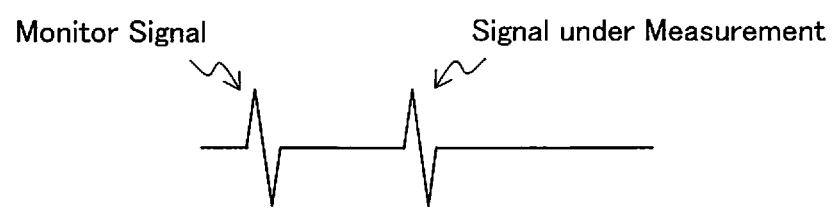
FIG. 7 is a diagram showing a waveform of the signal under measurement and the monitor signal each generated as an output from the I/V amplifier 26 according to the second embodiment.

FIG. 7 is a diagram showing a waveform of the signal under measurement and the monitor signal each generated as an output from the I/V amplifier 26 according to the second embodiment. Note that in FIG. 7, the vertical axis represents voltage and the horizontal axis, time. Referring to FIG. 7, the signal under measurement and the monitor signal do not overlap with each other in the time domain. For this purpose, it will suffice if the light pulse under measurement and the illumination light pulse may be received by the signal-under-measurement generator 16 in such a way that the pulses do not overlap with each other in the time domain. In the second embodiment, by increasing (but to a constant value) the optical path difference between an optical path where the object under measurement 2 is present (path of light passing through the object under measurement 2) and an optical path where the object under measurement 2 is not present (path of light reflected from the mirrors M22, M24)—each path being located between the illumination light pulse generator 14 and the signal-under-measurement generator 16—the light pulse under measurement and the illumination light pulse are configured or designed to be received by the signal-under-measurement generator 16 in such a way that both pulses do not overlap with each other in the time domain.

The operation of the second embodiment is the same as that of the first embodiment.

According to the second embodiment, advantageous effects similar to those of the first embodiment can be achieved without using the monitor signal generator 18.

Note that as with the modification (refer to FIG. 10) of the first embodiment, also in the second embodiment, the time difference correction unit (error correction unit) 49 can correct the errors without using the light pulse delay unit 34.

Third Embodiment

The light measurement apparatus 1 according to the third embodiment differs from the apparatus 1 according to the second embodiment in that the former includes an optical system (the mirrors M21, M22, M23, M24, and stages Stg 1, Stg 2) in which any selected one of a light pulse under measurement and an illumination light pulse is provided to the signal-under-measurement generator 16.

Figure 8:
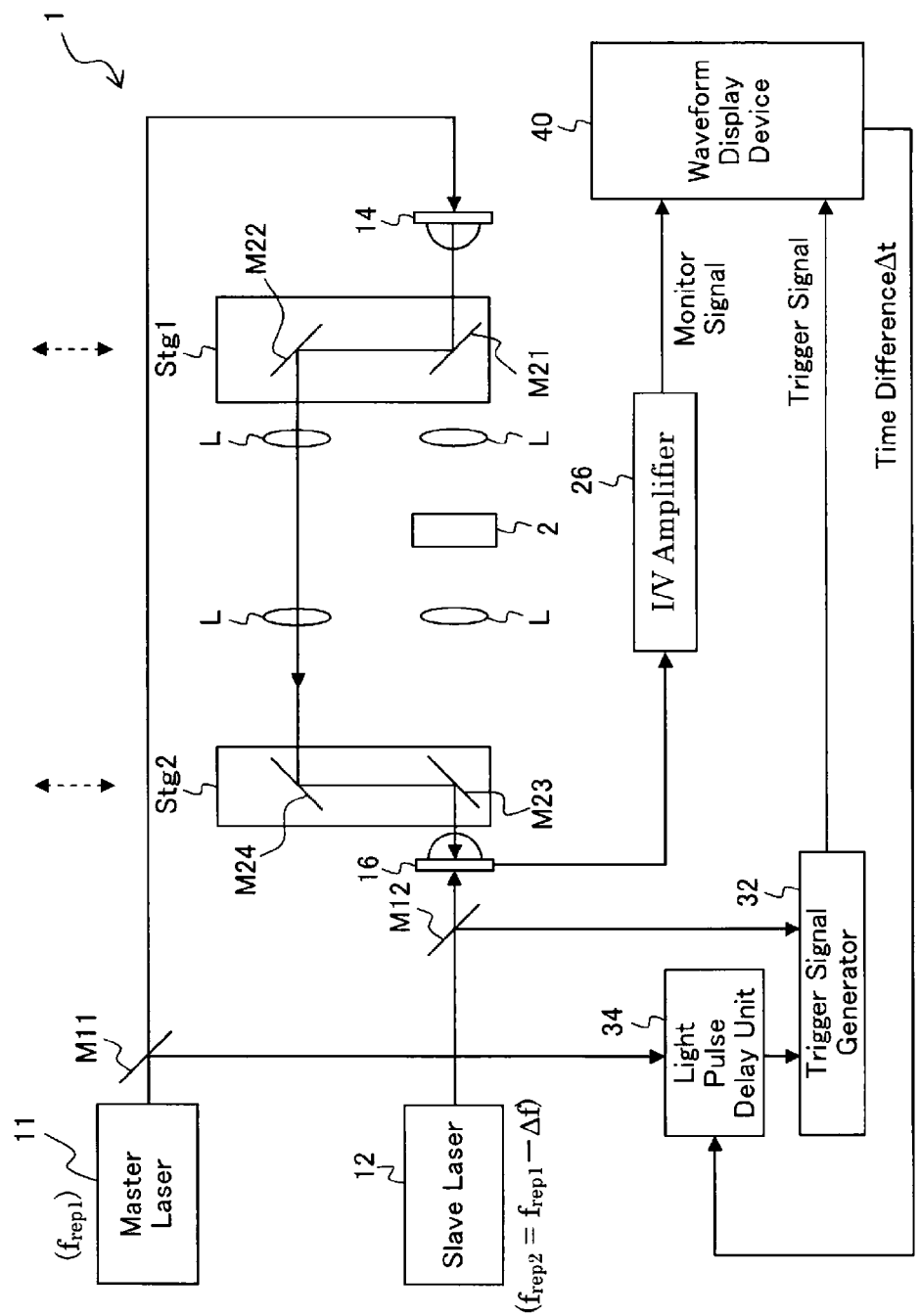
FIG. 8 is a diagram showing a configuration of the light measurement apparatus 1 according to the third embodiment of the present invention (at the time when the monitor signal is acquired)
Figure 9:
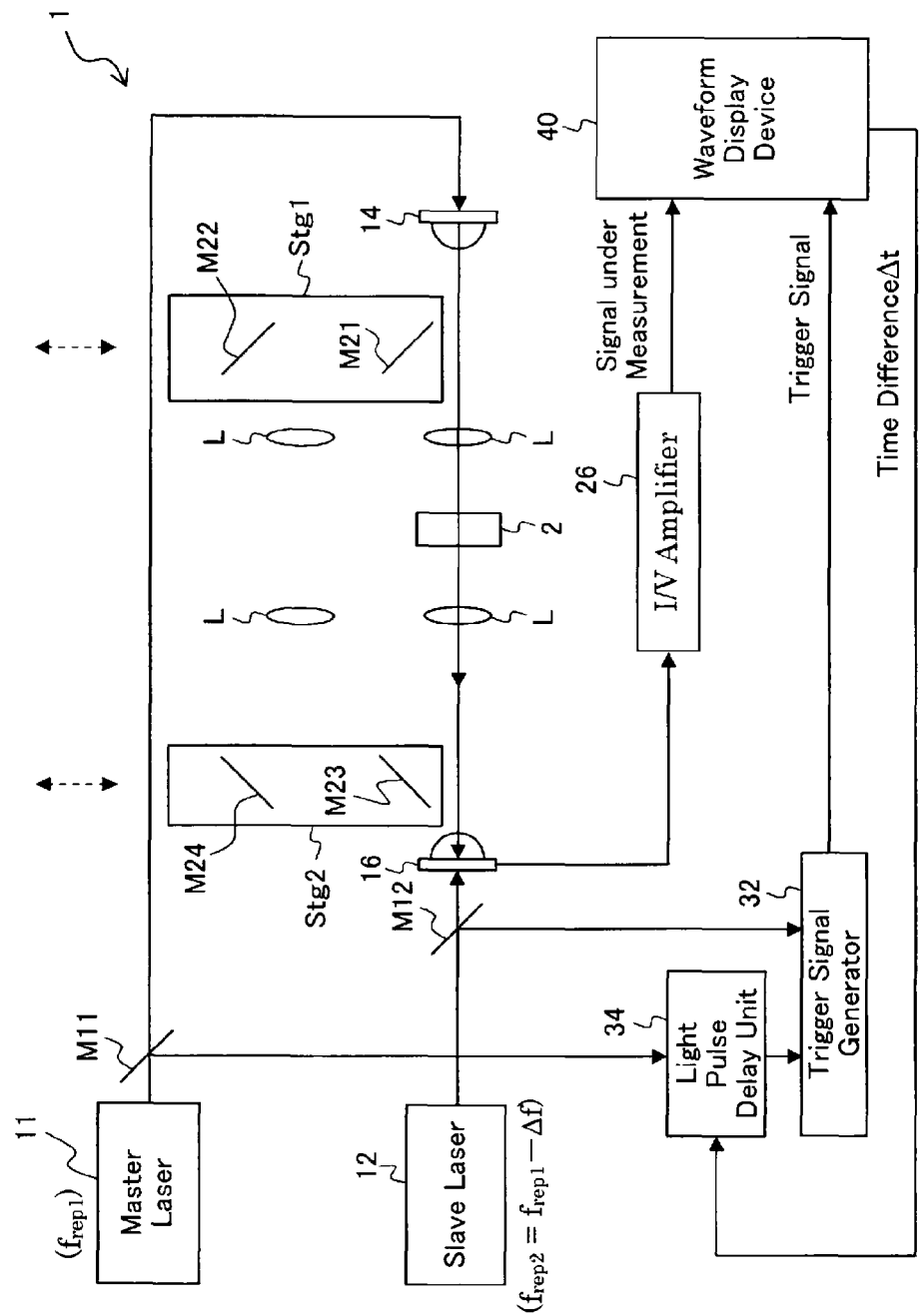
FIG. 9 is a diagram showing a configuration of the light measurement apparatus 1 according to the third embodiment of the present invention (at the time when the signal under measurement is acquired)

FIG. 8 is a diagram showing a configuration of the light measurement apparatus 1 according to the third embodiment of the present invention (at the time when the monitor signal is acquired). FIG. 9 is a diagram showing a configuration of the light measurement apparatus 1 according to the third embodiment of the present invention (at the time when the signal under measurement is acquired). The light measurement apparatus 1 according to the third embodiment includes the master laser 11, the slave laser 12, the half mirrors M11, M12, the mirrors M21, M23, M22, M24, stages Stg1, Stg2, the lens L, the illumination light pulse generator 14, the signal-under-measurement generator 16, the I/V amplifier 26, the trigger signal generator 32, the light pulse delay unit (error correction unit) 34, and the waveform display device 40. Elements similar to the second embodiment are designated hereinafter with the same reference numerals as those of the second embodiment, and their description will not be provided herein.

The master laser 11, the slave laser 12, the half mirrors M11, M12, the lens L, the illumination light pulse generator 14, the signal-under-measurement generator 16, the I/V amplifier 26, the trigger signal generator 32, the light pulse delay unit (error correction unit) 34, and the waveform display device 40, are the same as those in the second embodiment and thus, their description will not be provided.

Although in the second embodiment, reference numerals M21 and M23 each represent a half mirror, they represent a mirror in the third embodiment. The mirrors M21, M22 are mounted on the stage Stg1, while the mirrors M23, M24 are mounted on the stage Stg2.

The stage Stg1 allows the mirror M21 to move to a place where the mirror reflects an illumination light pulse (refer to FIG. 8) or alternatively, where the mirror does not reflect the illumination light pulse (refer to FIG. 9). The stage Stg2 allows the mirror M23 to move to a place where the mirror reflects an illumination light pulse (refer to FIG. 8) or alternatively, where the mirror does not reflect the illumination light pulse (refer to FIG. 9). Note that dotted arrows in FIG. 8 and FIG. 9 indicate directions in which the stage Stg1 and the stage Stg2 are allowed to move.

Referring to FIG. 8, in situations where the stage Stg1 and the stage Stg2 causes the mirror M21 and the mirror M23 to move, respectively, to the place where they reflect an illumination light pulse, the illumination light pulse is provided from the illumination light pulse generator 14 to the signal-under-measurement generator 16. Thus, the signal-under-measurement generator 16 generates as an output a monitor signal.

Referring to FIG. 9, in situations where the stage Stg1 and the stage Stg2 causes the mirror M21 and the mirror M23 to move, respectively, to the place where they do not reflect an illumination light pulse, the light pulse under measurement is provided to the signal-under-measurement generator 16. Thus, the signal-under-measurement generator 16 generates as an output a signal under measurement.

This causes the light pulse under measurement and the illumination light pulse to be received by the signal-under-measurement generator 16 in such a way that both pulses do not overlap with each other in the time domain. In the third embodiment, the optical path difference between an optical path (refer to FIG. 9) where the object under measurement 2 is present and that (refer to FIG. 8) where the object under measurement 2 is not present may be zero if it is a constant value, each path being located between the illumination light pulse generator 14 and the signal-under-measurement generator 16.

The operation of the third embodiment is similar to that of the first embodiment.

According to the third embodiment, advantageous effects similar to those of the first embodiment are achieved without using the monitor signal generator 18.

Note that, as with the examples of modifications of the first embodiment (refer to FIG. 10), also in the third embodiment, error correction can be made by the time difference correction unit (error correction unit) 49 without using the light pulse delay unit 34.

Fourth Embodiment

The fourth embodiment differs from the first embodiment in that an error in the phase measurement of a signal under measurement is corrected by measuring an ambient temperature (environmental temperature) of the light measurement apparatus 1 without using a monitor signal.

Figure 11:
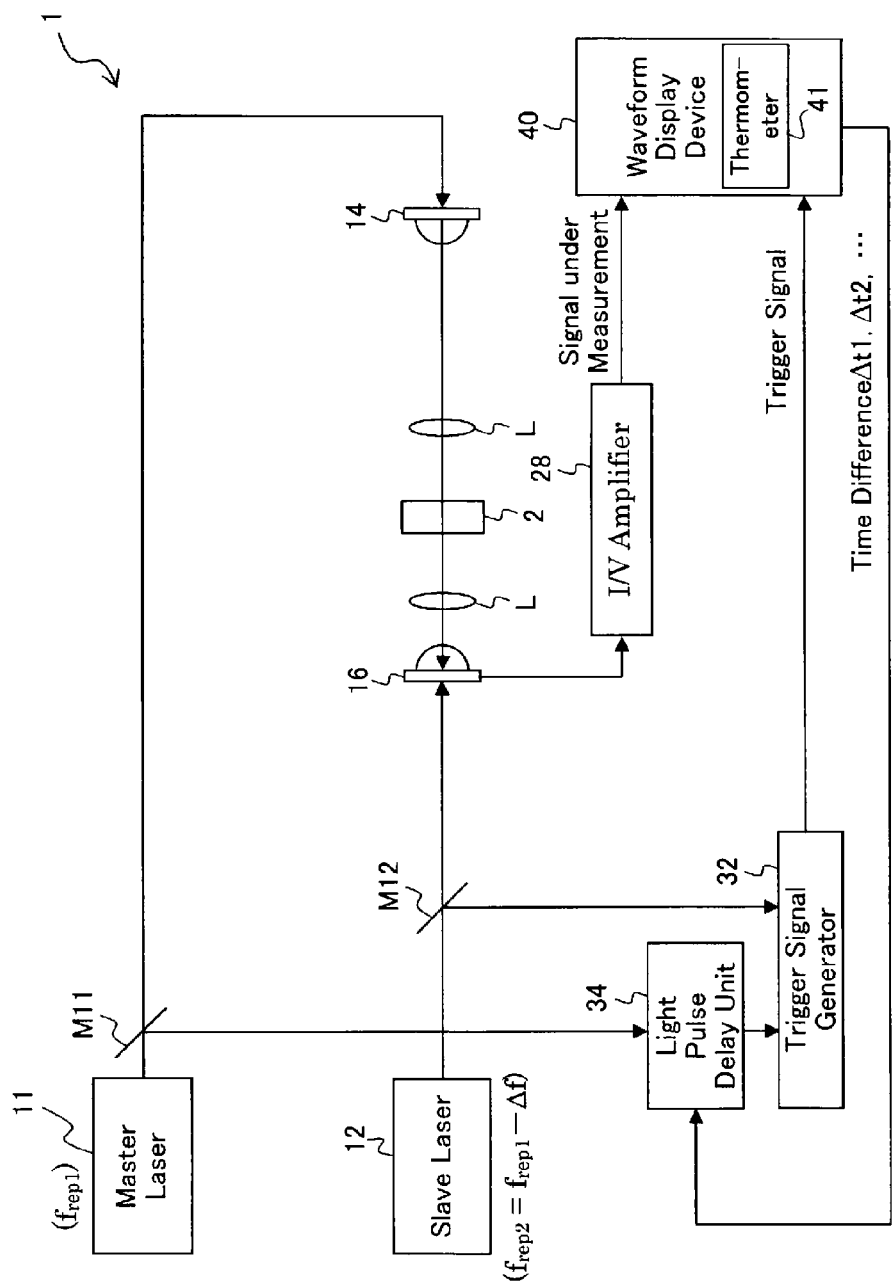
FIG. 11 is a diagram showing a configuration of the light measurement apparatus 1 according to the fourth embodiment of the present invention.

FIG. 11 is a diagram showing a configuration of the light measurement apparatus 1 according to the fourth embodiment of the present invention. The light measurement apparatus 1 according to the fourth embodiment includes the master laser 11, the slave laser 12, the half mirrors M11, M12, the lens L, the illumination light pulse generator 14, the signal-under-measurement generator 16, a I/V amplifier 28, the trigger signal generator 32, the light pulse delay unit (error correction unit) 34, and the waveform display device 40. Elements similar to the first embodiment are designated hereinafter with the same reference numerals as those of the first embodiment, and their description will not be provided herein.

The master laser 11, the slave laser 12, the half mirrors M11, M12, the lens L, the illumination light pulse generator 14, the signal-under-measurement generator 16, the trigger signal generator 32, and the light pulse delay unit (error correction unit) 34, are the same as those in the first embodiment and thus, their description will not be provided.

While amplifying the signal under measurement (which is a current signal) generated as an output from the signal-under-measurement generator 16, the IN amplifier 28 converts the amplified signal into a voltage signal, which is provided to the waveform display device 40.

The waveform display device 40 displays a waveform of the signal under measurement.

Figure 12:
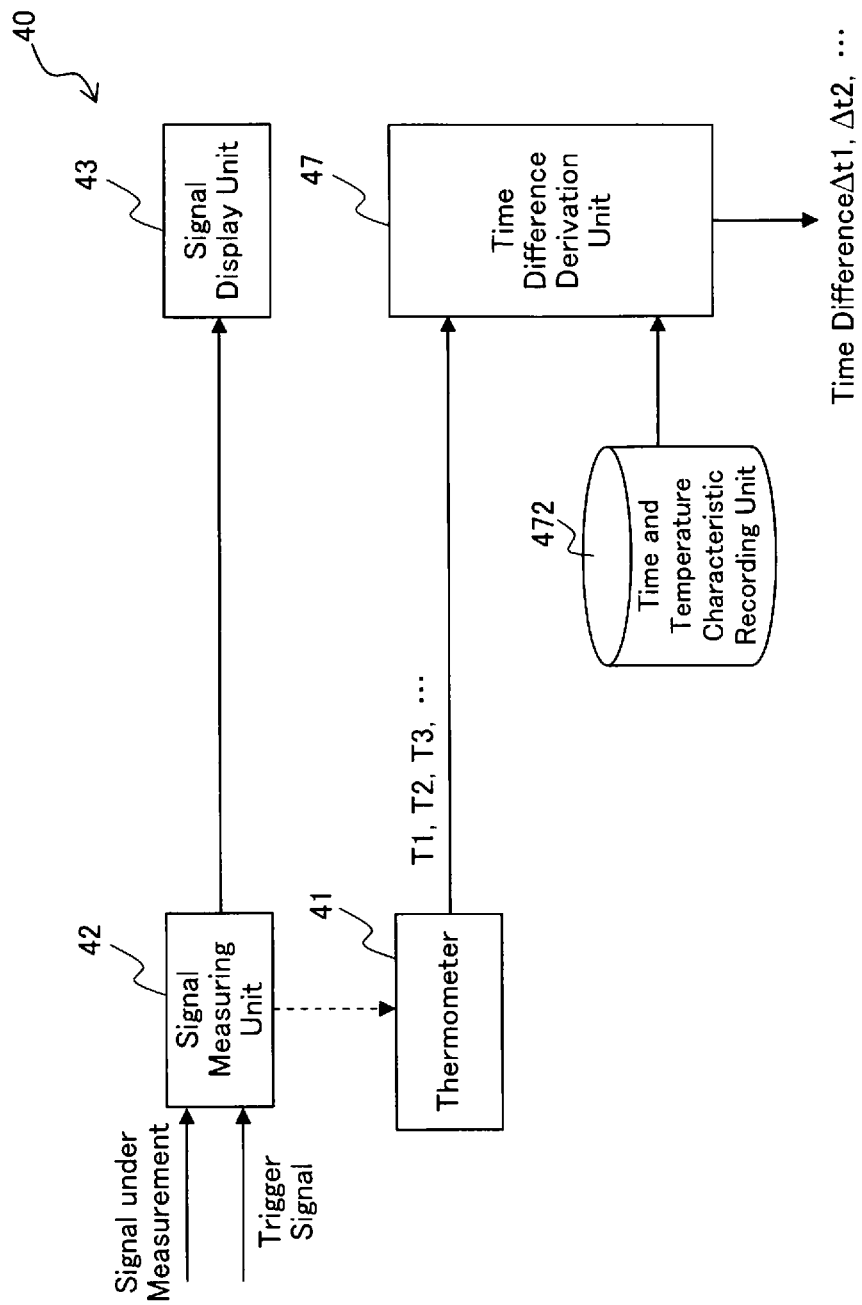
FIG. 12 is a functional block diagram showing a configuration of the waveform display device 40 according to the fourth embodiment.

FIG. 12 is a functional block diagram showing a configuration of the waveform display device 40 according to the fourth embodiment. The waveform display device 40 according to the fourth embodiment has a thermometer 41, the signal measuring unit 42, the signal display unit 43, a time and temperature characteristic recording unit 472 and a time difference derivation unit 47. The signal measuring unit 42 and the signal display unit 43 are the same as those in the first embodiment, and their description will not be provided. Note, however, that the signal measuring unit 42 communicates to the thermometer 41 an instruction that the signal measuring unit 42 starts measurement of a signal under measurement and makes measurements at a plurality of times.

The thermometer 41, at a point in time when receiving from the signal measuring unit 42 the instruction that the signal measuring unit 42 starts the measurement of the signal under measurement, measures the ambient temperatures of the light measurement apparatus 1 (environmental temperatures T1, T2, T3, . . . ), and provides them to the time difference derivation unit 47. For example, the environmental temperature of the signal under measurement at the first time measurement is represented as T1, the environmental temperature of the signal under measurement at the second time measurement is represented as T2, and the environmental temperature of the signal under measurement at the third time measurement is represented as T3. Strictly speaking, the measurement of the environmental temperature using the thermometer 41 is made just before measuring the signal under measurement. However, since in general, environmental temperatures will not cause a large momentary variation, environmental temperatures measured just before (or just after) measuring the signal under measurement can be regarded as those at the time of measuring the signal under measurement.

Note that although the foregoing description assumes that the thermometer 41 is contained within the waveform display device 40, the invention is not limited to the fact that the thermometer 41 is placed within the waveform display device 40. The thermometer 41 may be disposed, for example, in the neighborhood of the light pulse delay unit 34. In other words, it will suffice if the thermometer 41 may be located at any place that allows for measurement of environmental temperatures.

The time and temperature characteristic recording unit 472 records the relationship of the output point (e.g., output start point $\Delta t1m+\Delta tmd$: refer to FIG. 4) of the output from the signal-under-measurement generator 16 with respect to environmental temperatures. This relationship can be acquired by, for example, measuring the output start point of the signal under measurement while the environmental temperature is caused to vary with the light measurement apparatus 1 placed in a thermostat oven and with the object under measurement 2 placed out of the light measurement apparatus 1. Note that the relationship to be recorded may be data between an environmental temperature and an output point of an output from the signal-under-measurement generator 16, or alternatively, may be a mathematical expression showing a relationship between the environmental temperature and the output point of the output from the signal-under-measurement generator 16.

Figure 13:
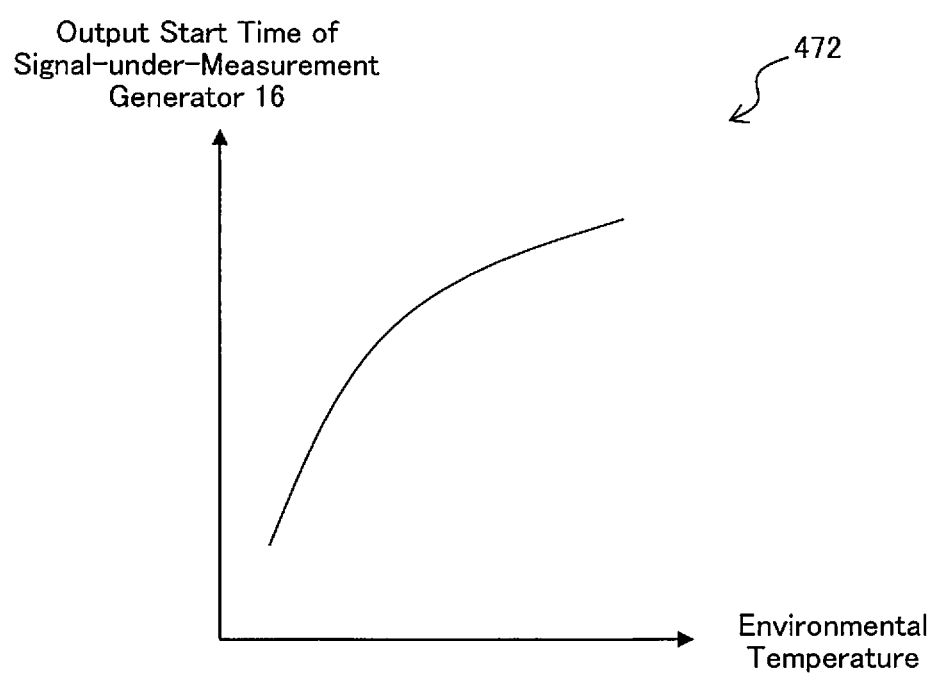
FIG. 13 is a graph showing one example of information recorded by the time and temperature characteristic recording unit 472.

FIG. 13 is a graph showing one example of information recorded by the time and temperature characteristic recording unit 472. As the environmental temperature rises, the optical path length of e.g., the light pulse under measurement extends, causing the output start point of output from the signal-under-measurement generator 16 to vary (e.g., to delay). For this reason, FIG. 13 illustrates that as the environmental temperature rises, the output start point (start time) of an output from the signal-under-measurement generator 16 varies (e.g., increases monotonously). Note that although, in FIG. 13, the output start point of the output from the signal-under-measurement generator 16 is shown in a curve, the point is also thought to follow in a straight line.

Based on the information recorded by the time and temperature characteristic recording unit 472, the time difference derivation unit 47 derives a lag (time differences $\Delta t1$, $\Delta t2$) in the output point of the signal under measurement for environmental temperatures (environmental temperatures T2, T3) at the point in time when the reference temperatures (environmental temperatures T1, T2) and the signal under measurement are measured.

Figure 15:
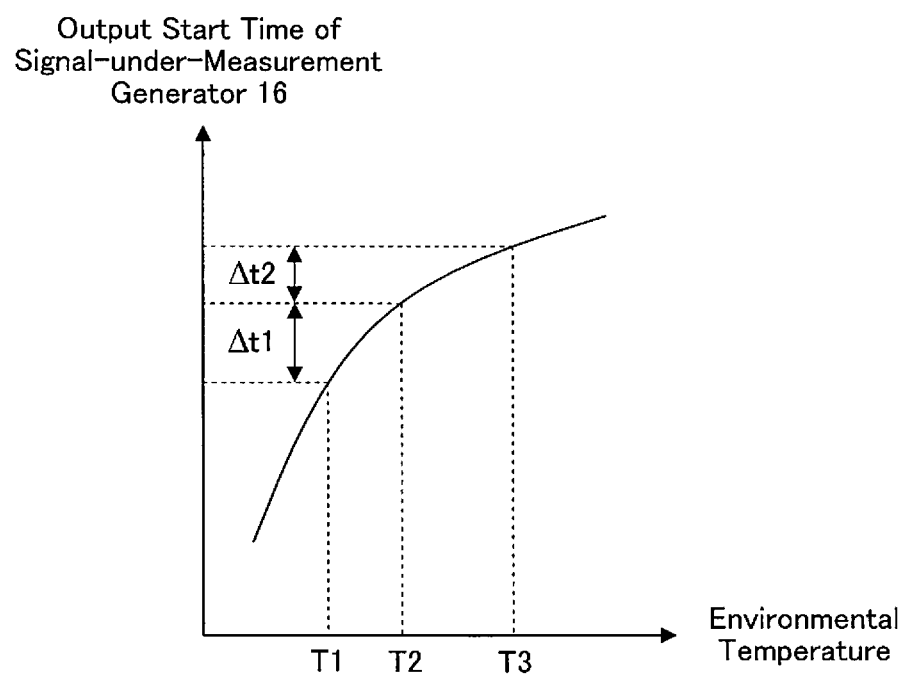
FIG. 15 is a graph showing a time difference derived by the time difference derivation unit 47.

FIG. 15 is a graph showing a time difference derived by the time difference derivation unit 47. Note that the output start point (start time) of the signal under measurement, as shown in FIG. 15 is the same as that in FIG. 13.

If the reference temperature is assumed to be the environmental temperature at the point in time when signal under measurement was measured at the last time, then the lag (time difference) is $\Delta t1$ in the output point of the signal under measurement for the reference temperature T1 (first time) and the environmental temperature T2 (second time). This means that the output start point of the signal under measurement is presumed to be delayed by $\Delta t1$, due to the fact that the environmental temperature increases from T1 to T2 between the point in time when the signal under measurement is measured at the first time and the point in time when it is measured at the second time.

Between the reference temperature T2 (second time) and the environmental temperature T3 (third time), the lag (time difference) is $\Delta t2$ at the output point of the signal under measurement. This means that the output start point of the signal under measurement is presumed to be delayed by $\Delta t2$, due to the fact that the environmental temperature increases from T2 to T3 between the point in time when the signal under measurement is measured at the second time and the point in time when it is measured at the third time.

The time difference derivation unit 47 provides the time differences $\Delta t1$, $\Delta t2$, . . . to the light pulse delay unit (error correction unit) 34. Note that the light pulse delay unit 34 extends the time that causes the master laser light pulse to be delayed by the time differences $\Delta t1$, $\Delta t2$, . . . received from the time difference derivation unit 47 of the waveform display device 40. This corrects the output point of the trigger signal so that the point is delayed by the time differences $\Delta n$, $\Delta t2$, . . . , thus correcting the lags $\Delta t1$, $\Delta t2$, . . . in the output point of the signal under measurement resulting from the output point of the trigger signal being set at the time origin point.

The operation of the fourth embodiment will next be described.

Figure 14:
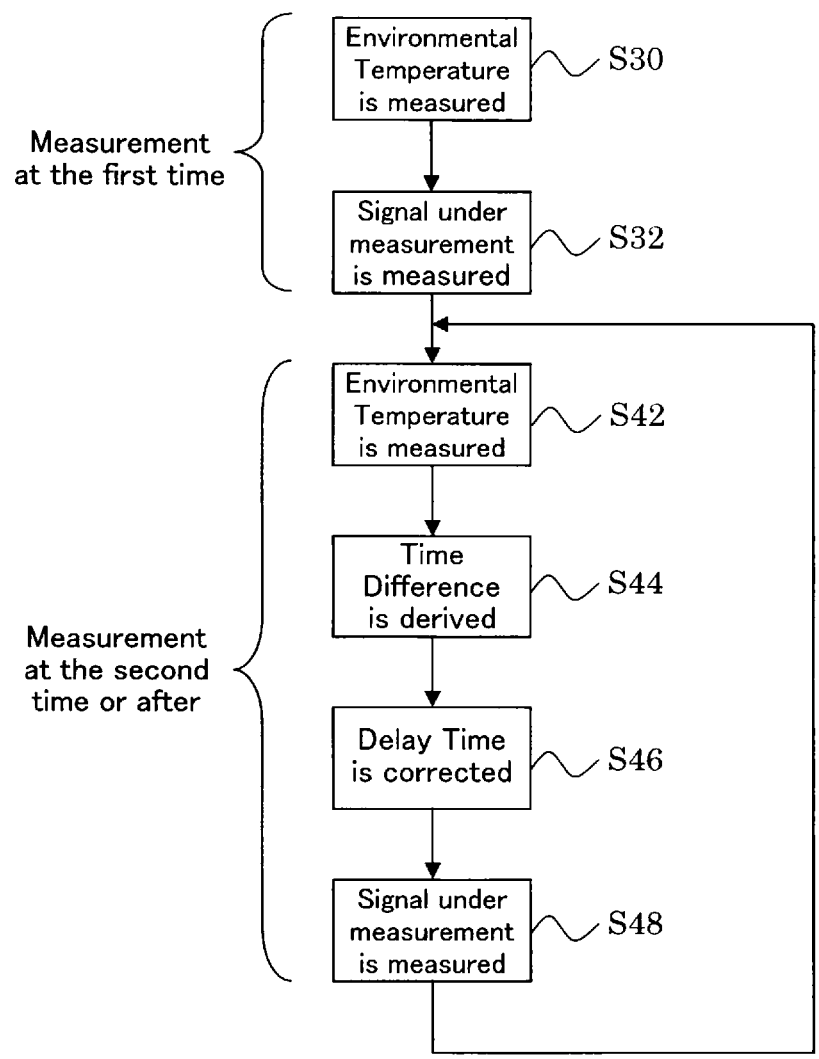
FIG. 14 is a flow chart showing the operation of the fourth embodiment.

FIG. 14 is a flow chart showing the operation of the fourth embodiment.

A master laser light pulse generated as an output from the master laser 11 is provided via the half mirror M11 to the illumination light pulse generator 14. An illumination light pulse is generated as an output from the illumination light pulse generator 14. The illumination light pulse passes through the object under measurement 2 and then becomes a light pulse under measurement, which is provided to the signal-under measurement generator 16.

Moreover, a slave laser light pulse generated as an output from the slave laser 12 is provided via the half mirror M12 to the signal-under-measurement generator 16.

A signal under measurement (which is a current signal) is generated as an output from the signal-under measurement generator 16 and is converted, while being amplified by the I/V amplifier 28, into a voltage signal, which is provided to the waveform display device 40.

Note that the master laser light pulse and the slave laser light pulse are reflected from the half mirrors M11, M12, respectively, and are provided to the trigger signal generator 32, however, with the master laser light pulse being provided via the light pulse delay unit 34 to the trigger signal generator 32. Note again that the trigger signal generator 32 generates an output trigger signal at a point in time when simultaneously receiving the master laser pulse and the slave laser light pulse, and the trigger signal is provided to the waveform display device 40.

Here, the thermometer 41 measures the environmental temperature T1 (S30: measurement at the first time), which is provided to the time difference derivation unit 47. Further, the signal measuring unit 42 measures the output point (e.g., output start point) of the signal under measurement, relative to the trigger signal, and the voltage of the signal under measurement (S32: measurement at the first time). The measurement result obtained by the signal measuring unit 42 is displayed on the signal display unit 43.

After a certain period of time has elapsed after the signal under measurement has been measured (S32: measurement at the first time), the thermometer 41 measures the environmental temperature T2 (S42: measurement at the second time).

Here, based on the information recorded by the time and temperature characteristic recording unit 472, the time difference derivation unit 47 derives a lag (time difference $\Delta t1$) at the output point of the signal under measurement between the reference temperature (environmental temperature T1: measurement at the first time) and the environmental temperature (environmental temperature T2: measurement at the second time) at the point in time when the signal under measurement are measured (S44). It is presumed that the increase in environmental temperature from T1 to T2 causes the output start point of the signal under measurement to be delayed by $\Delta t1$.

The time difference derivation unit 47 provides the time difference $\Delta t1$ to the light pulse delay unit (error correction unit) 34. Note that the light pulse delay unit 34 extends the time that causes the master laser light pulse to be delayed by the time difference $\Delta t1$ received from the time difference derivation unit 47 of the waveform display device 40. This causes the output point of the trigger signal to be delayed by the time difference $\Delta t1$, thus correcting the time lag $\Delta t1$ in the output point of the signal under measurement resulting from the output point of the trigger signal being set at the time origin point (S46).

Thereafter, the signal measuring unit 42 measures the output point (e.g., output start point) of the signal under measurement relative to the trigger signal, and the voltage of the signal under measurement (S48: measurement at the second time).

After a certain period of time has elapsed after the signal under measurement has been measured (S48: measurement at the second time), the thermometer 41 measures the environmental temperature T3 (S42: measurement at the third time).

Here, based on the information recorded by the time and temperature characteristic recording unit 472, the time difference derivation unit 47 derives a lag (time difference $\Delta t2$) at the output point of the signal under measurement between the reference temperature (environmental temperature T2: measurement at the second time) and the environmental temperature (environmental temperature T3: measurement at the third time) at the point in time when the signal under measurement have been measured (S44). It is presumed that the rise of the environmental temperature from T2 to T3 causes the output start point of the signal under measurement to be delayed by $\Delta t2$.

The time difference derivation unit 47 provides the time difference Δt2 to the light pulse delay unit (error correction unit) 34. Note that the light pulse delay unit 34 extends the time that causes the master laser light pulse to be delayed by the time difference Δt2 received from the time difference derivation unit 47 of the waveform display device 40. This causes the output point of the trigger signal to be delayed by the time difference Δt2, thus correcting the lag Δt2 in the output point of the signal under measurement resulting from the output point of the trigger signal being set at the time origin point (S46).

Thereafter, the signal measuring unit 42 measures the output point (e.g., output start point) of the signal under measurement relative to the trigger signal, and the voltage of the signal under measurement (S48: measurement at the third time)

According to the fourth embodiment, the time difference derivation unit 48 presumes from the environmental temperature an error in the measurement result (output point) of the object under measurement 2 by means of light, such as terahertz light (illumination light pulse)—the error resulting from the changed ambient temperature (environmental temperature) of the light measurement apparatus 1, and then the light pulse delay unit 34 corrects the error—as a result, the phase information in the measurement result of the object under measurement 2 can be obtained correctly.

Figure 16:
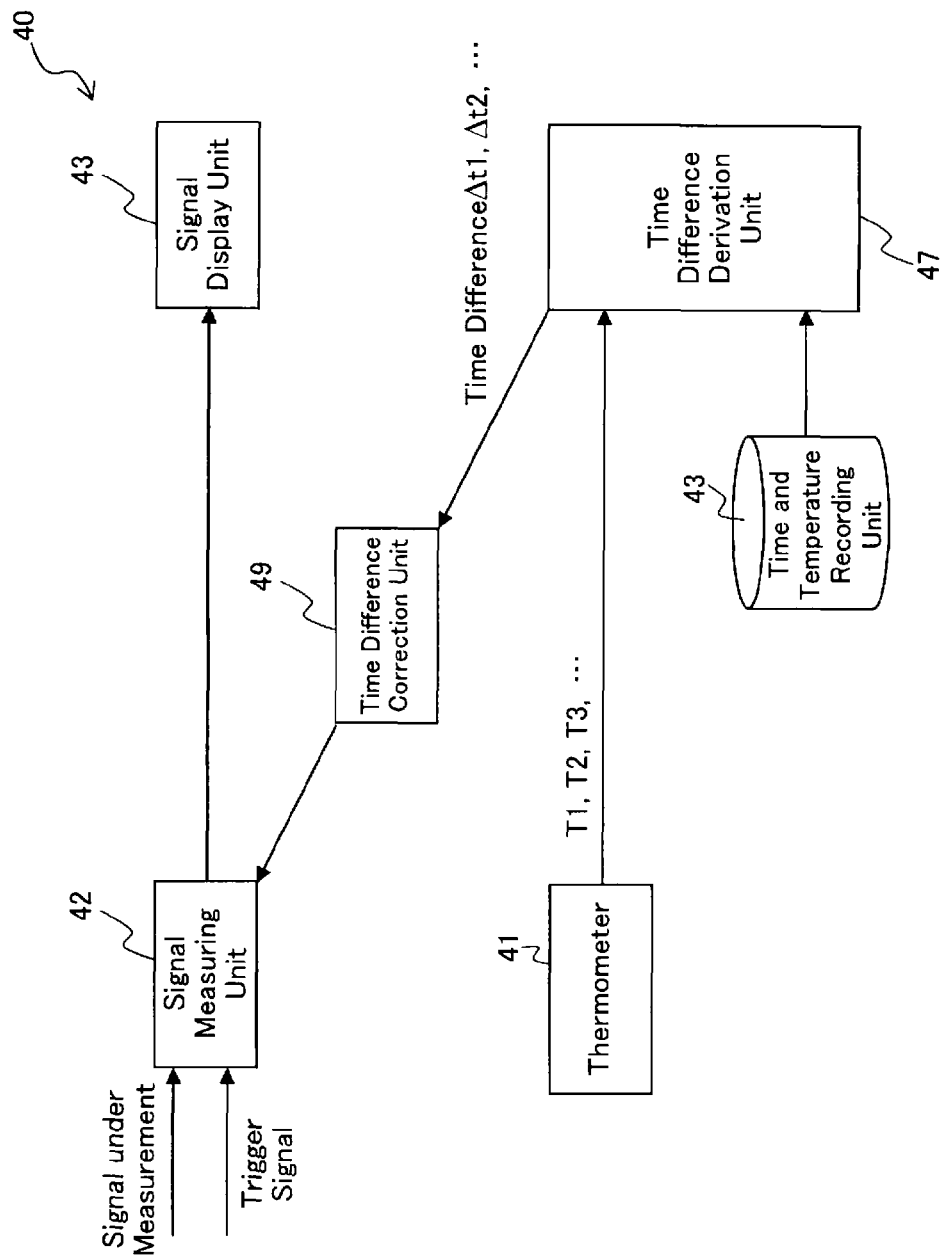
FIG. 16 is a functional block diagram illustrating a configuration of the waveform display device 40 according to a modification (error correction is made without using the light pulse delay unit 34) of the fourth embodiment.

Note that although in the fourth embodiment the light pulse delay unit 34 has corrected errors by shifting the trigger signal by Δt1, Δt2, . . . , error correction can also be made without using the light pulse delay unit 34. FIG. 16 is a functional block diagram illustrating a configuration of the waveform display device 40 according to a modification (error correction is made without using the light pulse delay unit 34) of the fourth embodiment.

The waveform display device 40 according to the modification of the fourth embodiment is configured such that the time difference correction unit (error difference correction unit) 49 is further added to the waveform display device 40 in the fourth embodiment.

The time difference derivation unit 47 in the waveform display device 40 according to the modification of the fourth embodiment provides the derived time differences Δt1, Δt2, . . . not to the light pulse delay unit 34, but to the time difference correction unit 49. The time difference correction unit 49 provides the time differences Δt1, Δt2, . . . to the signal measuring unit 42, where the time of the signal under measurement is caused to be shifted by −Δt1, −Δt2, . . . . Note that if the signal measuring unit 42 is assumed to generate as an output the measurement results after the results have been processed to digital data, it will suffice if time data in this digital data may be generated as an output with it altered by −Δt. In this way, the measurement results obtained by the signal measuring unit 42 are corrected.

Fifth Embodiment

The light measurement apparatus 1 according to a fifth embodiment through an eighth embodiment measures the amplitude of a signal under measurement.

Figure 17:
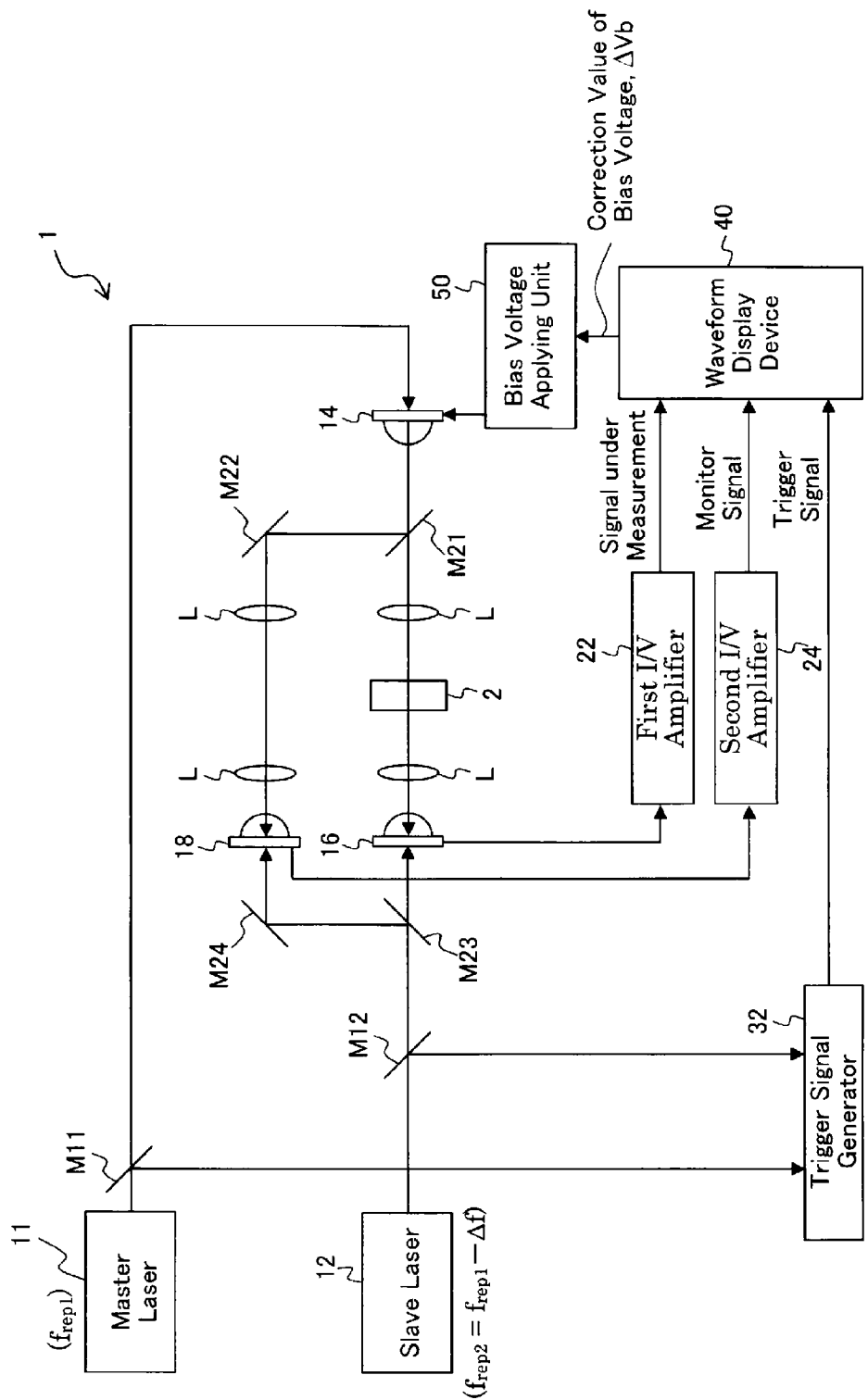
FIG. 17 is a diagram showing a configuration of the light measurement apparatus 1 according to the fifth embodiment of the present invention.

FIG. 17 is a diagram showing a configuration of the light measurement apparatus 1 according to the fifth embodiment of the present invention. The light measurement apparatus 1 according to the fifth embodiment includes the master laser 11, the slave laser 12, the half mirrors M11, M12, M21 and M23, the mirrors M22, M24, the lens L, the illumination light pulse generator 14, the signal-under-measurement generator 16, the monitor signal generator 18, the first I/V amplifier 22, the second I/V amplifier 24, the trigger signal generator 32, the waveform display device 40, and a bias voltage applying unit (amplitude error correction unit) 50. The light measurement apparatus 1 according to the fifth embodiment is a device that measures the object under measurement 2.

Note that the half mirrors M11, M12, M21 and M23 are merely examples, and any suitable devices other than half mirrors may be used that can cause separation of a light beam.

The master laser 11 generates as an output a master laser light pulse. A repetition frequency of the master laser light pulse is $f_{rep1}$. The frequency $f_{rep1}$ is in the order of, e.g., 50 MHz. The master laser light pulse is separated by the half mirror M11 into light that is to be provided to the trigger signal generator 32 and light that is to be provided to the illumination light pulse generator 14.

The slave laser 12 generates as an output a slave laser light pulse having a repetition frequency different from that of the master laser light pulse. The repetition frequency of the slave laser light pulse is represented as $f_{rep2}$ ($=f_{rep1}-\Delta f$), where Δf is not zero. The frequency Δf is a value of approximately 1 kHz or less (e.g., the order of 5 Hz). Note that even if the slave laser light pulse has the same repetition frequency as that of the master laser light pulse, then it will suffice if the slave pulse has a different phase from that of the master pulse. It will suffice if a phase shift between the slave laser light pulse and the master laser light pulse is caused to vary with time, for example.

The slave laser light pulse is separated by the half mirror M12 into light that is to be provided to the trigger signal generator 32, and light that is to be provided to the signal-under-measurement generator 16 and the monitor signal generator 18. The light that is to be provided to the signal-under-measurement generator 16 and the monitor signal generator 18 is further separated by the half mirror M23 into light that is to be provided to the signal-under-measurement generator 16 and light that is to be provided to the monitor signal generator 18. The light that is to be provided to the monitor signal generator 18 is reflected from the mirror M24 and then provided to the monitor signal generator 18.

The illumination light pulse generator 14 receives the master laser light pulse to generate as an output an illumination light pulse. The illumination light pulse generator 14 serves as, for example, a photoconductive switch, and a bias voltage is applied to this switch. The illumination light pulse is, for example, an electromagnetic wave having a frequency of 0.01 [THz] or more and 100 [THz] or less, and the light pulse is contemplated to be a terahertz wave (for example, its frequency is 0.03 [THz] or more and 10 [THz] or less).

The illumination light pulse is separated by the half mirror M21 into the light that is to be provided to the signal-under-measurement generator 16 and the light that is to be provided to the monitor signal generator 18.

The illumination light pulse which is provided to the signal-under-measurement generator 16 is directed to the object under measurement 2 while being focused by the lens L. An illumination light pulse that has been passed through the object under measurement 2 (a light pulse under measurement) is provided to the signal-under-measurement generator 16 while being focused by the lens L.

The illumination light pulse which is provided to the monitor signal generator 18 is reflected from the mirror M22 and provided to the monitor signal generator 18 while being further focused by two lenses L.

The signal-under-measurement generator 16 receives a light pulse under measurement obtained by illuminating the object under measurement 2 with an illumination light pulse. The signal-under-measurement generator 16, at a point in time when receiving the light pulse under measurement and further a slave laser light pulse, generates as an output a signal under measurement according to the power of the light pulse under measurement. The signal-under-measurement generator 16 serves as, e.g., a photoconductive switch.

The monitor signal generator 18 receives the illumination light pulse and the slave laser light pulse, and generates as an output a monitor signal. The monitor signal generator 18 serve as, for example, a photoconductive switch.

The first I/V amplifier 22, while amplifying the signal under measurement (which is a current signal) generated as an output from the signal-under-measurement generator 16, converts the amplified signal into a voltage signal, and provides the voltage signal to the waveform display device 40.

The second I/V amplifier 24, while amplifying the monitor signal (which is a current signal) generated as an output from the monitor signal generator 18, converts the amplified signal into a voltage signal, and provides the voltage signal to the waveform display device 40.

The trigger signal generator 32 generates an output trigger signal at a point in time when simultaneously receiving a master laser light pulse and a slave laser light pulse. The trigger signal is provided to the waveform display device 40.

The trigger signal generator 32 includes, for example, an optical coupler that generates as an output a light pulse at a point in time when simultaneously receiving the master laser light pulse and the slave laser light pulse, and a photodetector that performs photoelectric conversion of an output from the optical coupler, to generate an output trigger signal, which is an electrical signal.

A bias voltage applying unit (amplitude error correction unit) 50 applies a bias voltage to the illumination light pulse generator 14. The bias voltage applying unit 50 corrects an amplitude of a signal under measurement by causing a bias voltage that is applied to the illumination light pulse generator 14 to vary by a result (bias voltage correction value ΔVb) derived by a correction value derivation unit 418 of the waveform display device 40. The amplitude of the signal under measurement varies according to the amplitude of a light pulse under measurement; the amplitude of the light pulse under measurement varies according to the amplitude of an illumination light pulse; and the amplitude of the illumination light pulse varies according to a bias voltage that is applied to the illumination light pulse generator 14. Thus, varying the bias voltage that is applied to the illumination light pulse generator 14 allows for correction of the amplitude of the signal under measurement.

The waveform display device 40 display a waveform of a signal under measurement.

Figure 18:
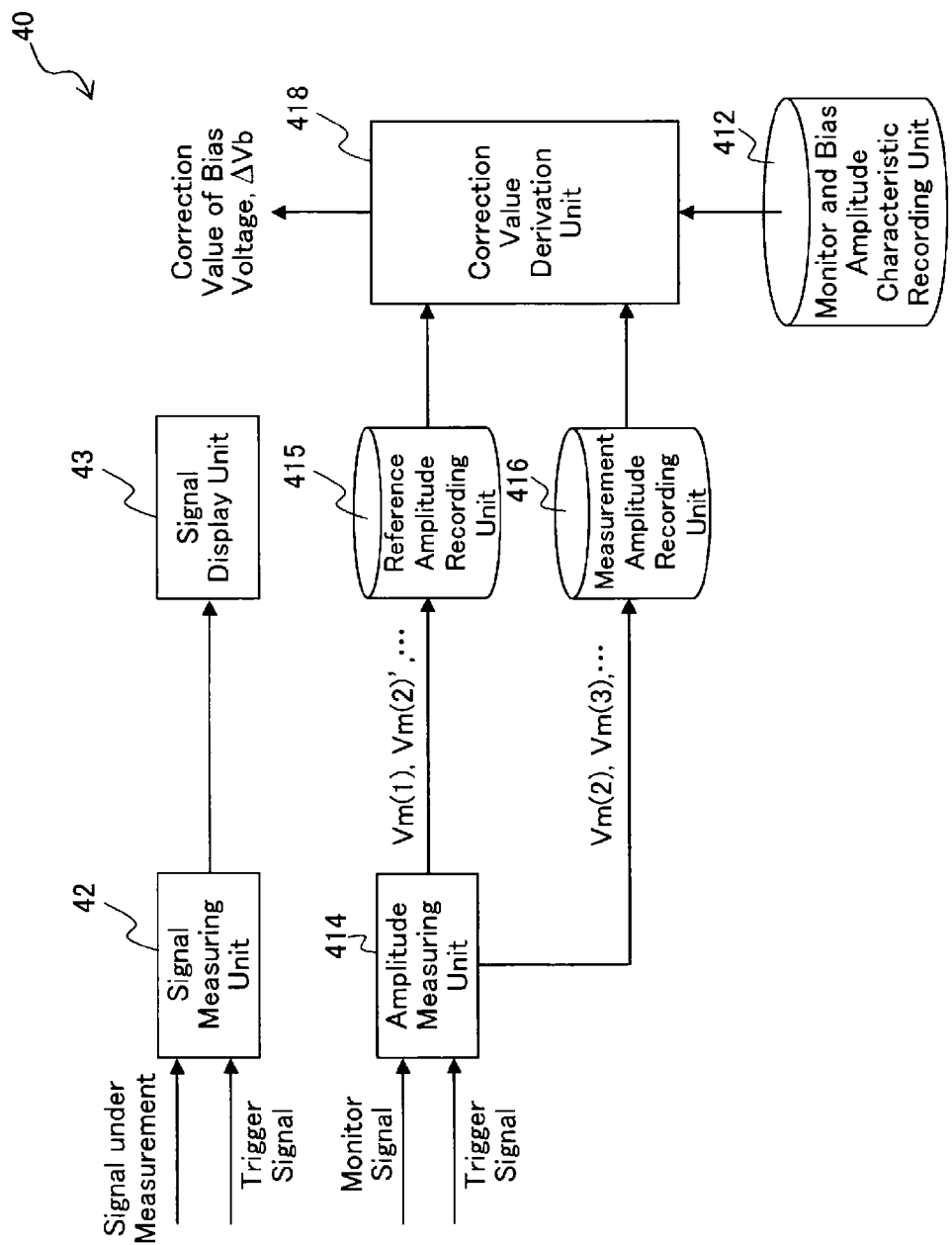
FIG. 18 is a functional block diagram showing a configuration of the waveform display device 40 according to the fifth embodiment.

FIG. 18 is a functional block diagram showing a configuration of the waveform display device 40 according to the fifth embodiment. The waveform display device 40 according to the fifth embodiment has the signal measuring unit 42, the signal display unit 43, a monitor and bias amplitude characteristic recording unit 412, an amplitude measuring unit 414 a reference amplitude recording unit 415, a measurement amplitude recording unit 416 and the correction value derivation unit 418.

The signal measuring unit 42 receives a signal under measurement and a trigger signal, and measures an output point of the signal under measurement relative to the trigger signal (it will suffice if the output start point is a point between the start and end of the output, for example). Add to this, the signal measuring unit 42 measures the amplitude of the signal under measurement with the amplitude associated with a time relative to the trigger signal.

The signal display unit 43 displays a measurement result obtained by the signal measuring unit 42, and the measurement result is a waveform of the signal under measurement.

The monitor and bias amplitude characteristic recording unit 412 records the relationship of the amplitude of the monitor signal with respect to the bias voltage that is applied to the illumination light pulse generator 14. The amplitude of the monitor signal may in some cases vary according to changes of e.g., the ambient temperature (environmental temperature) of the light measurement apparatus 1, even if the bias voltage is constant that is applied to the illumination light pulse generator 14. Thus, the above described relationship can be acquired by measuring the amplitude of the monitor signal while varying the bias voltage that is applied to the illumination light pulse generator 14 with the environmental temperature and the like maintained constant. Note that the relationship to be recorded may be data between a bias voltage that is applied to the illumination light pulse generator 14 and the amplitude of a monitor signal, or alternatively, may be a mathematical expression showing a relationship between the bias voltage applied to the illumination light pulse generator 14 and the amplitude of the monitor signal.

Figure 20:
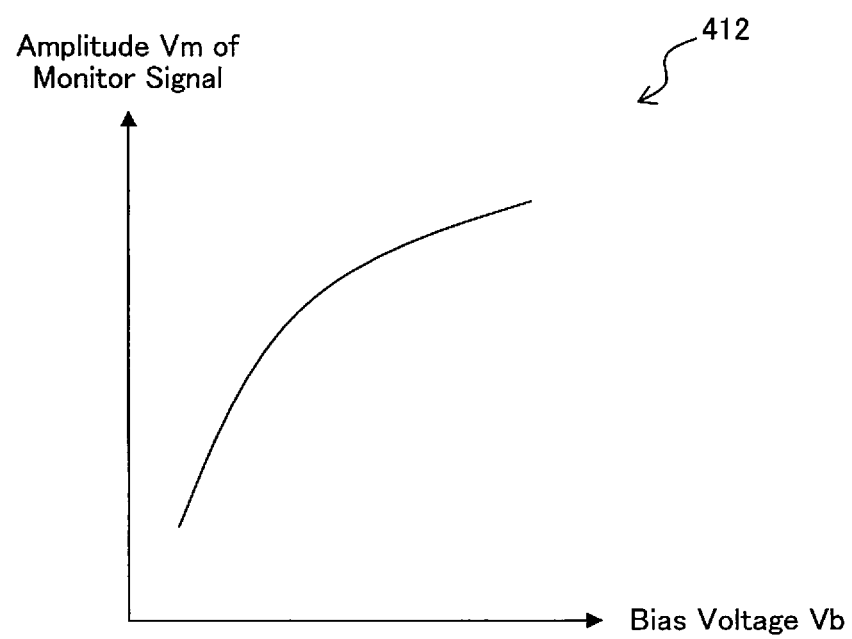
FIG. 20 is a graph showing one example of information recorded by the monitor and bias amplitude characteristic recording unit 412.

FIG. 20 is a graph showing one example of information recorded by the monitor and bias amplitude characteristic recording unit 412. As the bias voltage rises that is applied to the illumination light pulse generator 14, the amplitude Vm of the monitor signal varies (e.g., increases monotonously). Note that although, in FIG. 20, the amplitude Vm of the monitor signal is shown in a curve, the amplitude is also thought to follow in a straight line. The bias voltage that is applied to the illumination light pulse generator 14 is in some cases described hereinafter as "bias voltage."

The amplitude measuring unit 414 measures the amplitude of the monitor signal at a plurality of times.

Figure 21:
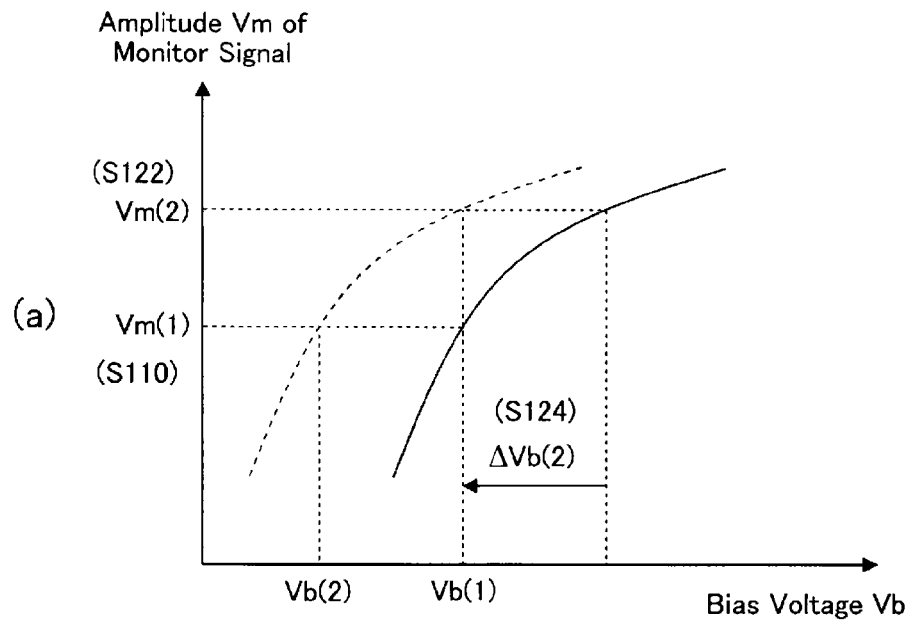
FIG. 21 is a graph showing a correction value of a bias voltage, derived by the correction value derivation unit 418.
Figure 21:
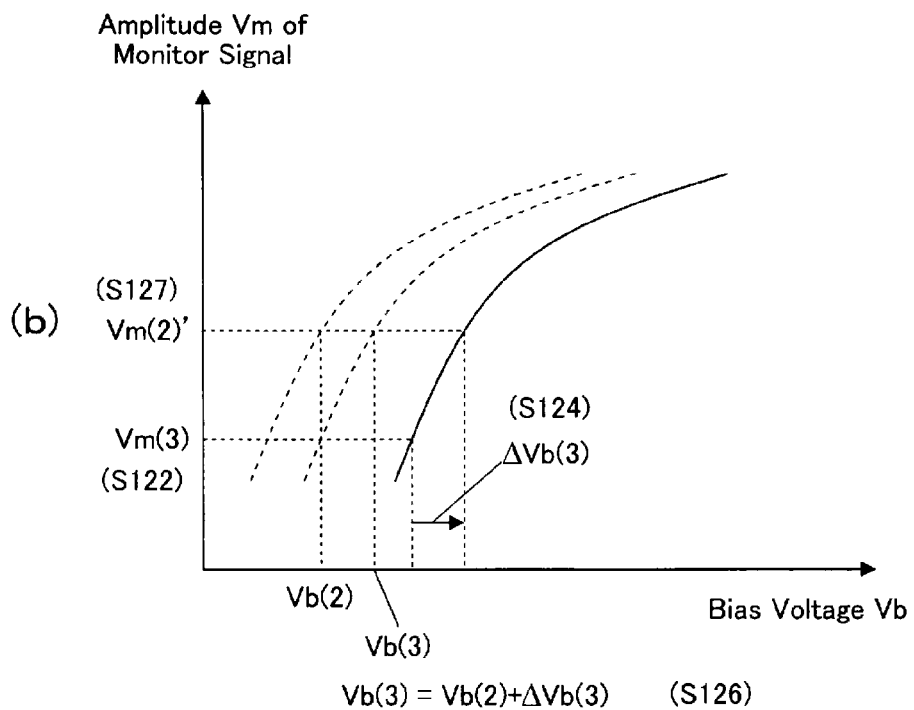

The measurement amplitude recoding unit 416 records measurement results (e.g., amplitudes of a monitor signal, Vm(2), Vm(3)) obtained by the amplitude measuring unit 414 (refer to FIG. 21).

The reference amplitude recording unit 415 records measurement results (e.g., amplitudes of a monitor signal, Vm(1), Vm(2)') obtained by the amplitude measuring unit 414 before a point in time when the measurement result obtained by the amplitude measuring unit 414 (what is recorded in the measurement amplitude record unit 416) is obtained (refer to FIG. 21).

For example, the measurement amplitude recording unit 416 records the measurement result Vm(2) at the second time of the amplitude of the monitor signal, and the reference amplitude recording unit 415 records the measurement result Vm(1) at the first time of the amplitude of the monitor signal (refer to FIG. 21(a)).

For example, the measurement amplitude recording unit 416 records the measurement result Vm(3) at the third time of the amplitude of the monitor signal, and the reference amplitude recording unit 415 records the measurement result Vm(2)' at the second time of the amplitude of the monitor signal (refer to FIG. 21(b)).

Based on the information recorded by the monitor and bias amplitude characteristic recording unit 412, the correction value derivation unit 418 derives a correction value of the bias voltage, ΔVb for causing the measurement result obtained by the amplitude measuring unit 414 (information recorded by the measurement amplitude recording unit 416) to correspond to the measurement result (information recorded by the reference amplitude recording unit 415) obtained by the amplitude measuring unit 414 before a point in time when the former measurement result is obtained.

For example, the correction value derivation unit 418 derives correction values of the bias voltage, $\Delta Vb(2)$, $\Delta Vb(3)$, based on the measurement result obtained by the amplitude measuring unit 414 (information recorded by the measurement amplitude recording unit 416, $Vm(2)$, $Vm(3)$), and the last measurement result obtained by the amplitude measuring unit 414 (information recorded by the reference amplitude recording unit 415, $Vm(1)$, $Vm(2)'$) (refer to FIG. 21).

The solid line in FIG. 21 represents information recorded by the monitor and bias amplitude characteristic recording unit 412 as illustrated in FIG. 20. The dotted line curve in FIG. 21 represents a relationship of the amplitude of the monitor signal with respect to the actual bias voltage. Although the dotted line curve in FIG. 21 is shown shifted, owing to changes of e.g., the environmental temperature, from the information recorded by the monitor and bias amplitude characteristic recording unit 412, the curve can be regarded as the same in form as the actual solid line curve in FIG. 21.

Referring FIG. 21(*a*), in order to cause $Vm(2)$ to correspond to $Vm(1)$, it will suffice if the bias voltage $Vb(1)$ is changed to $Vb(2)$ by causing the voltage to vary by $\Delta Vb(2)$ ($<0$).

The correction value derivation unit 418 derives correction values of the bias voltage, $\Delta Vb(3)$, based on the measurement result obtained by the amplitude measuring unit 414 (information recorded by the measurement amplitude recording unit 416, $Vm(3)$), and the measurement result obtained by the amplitude measuring unit 414—which is a measurement result (information recorded by the reference amplitude recording unit 415, $Vm(2)'$) that has been corrected by the bias voltage applying unit (amplitude error correction unit) 50 (refer to FIG. 21(*b*)).

Referring FIG. 21 (*a*), in order to cause $Vm(3)$ to correspond to $Vm(2)'$, it will suffice if the bias voltage $Vb(2)$ is changed to $Vb(3)$ by causing the voltage to vary by $\Delta Vb(3)$ 0).

The operation of the fifth embodiment will next be described.

Figure 19:
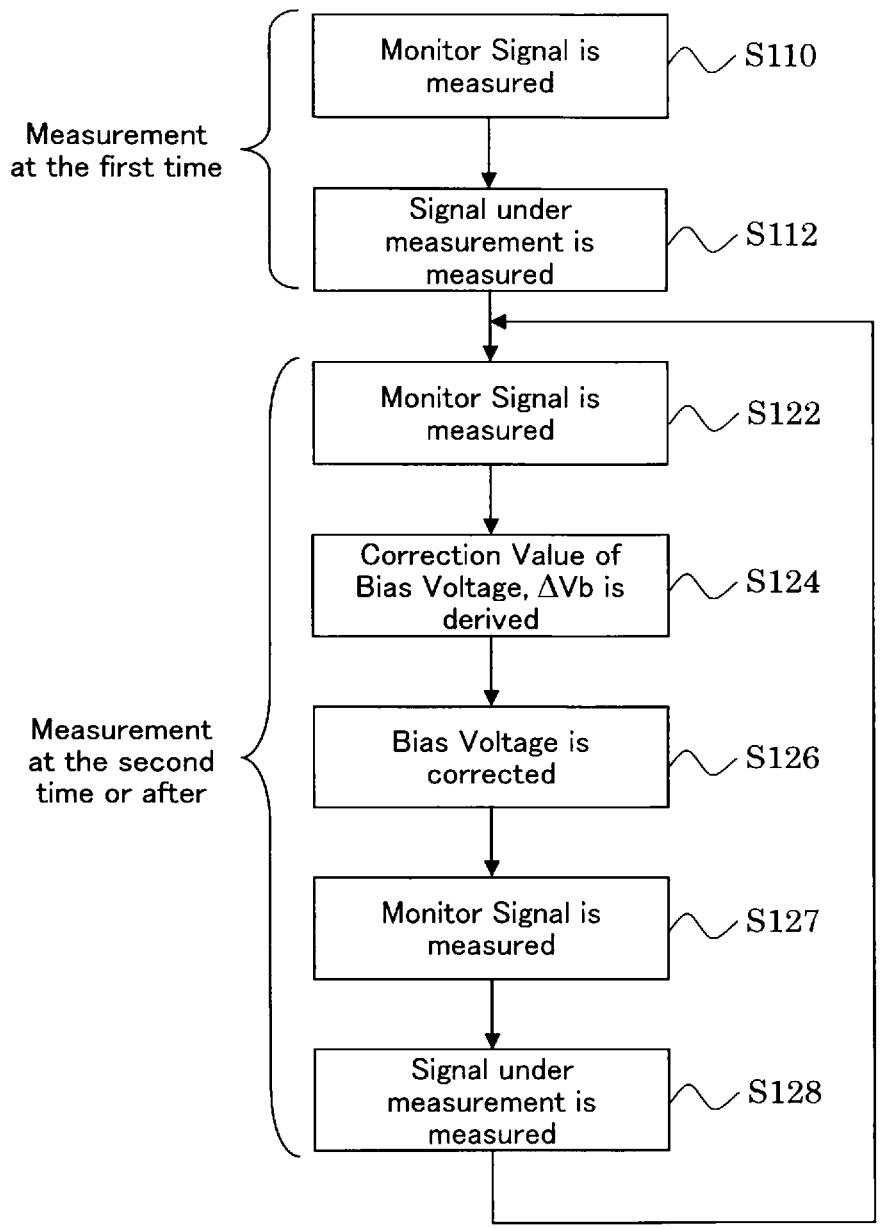
FIG. 19 is a flow chart showing the operation of the fifth embodiment.

FIG. 19 is a flow chart showing the operation of the fifth embodiment. FIG. 21 is a graph showing a correction value of a bias voltage, derived by the correction value derivation unit 418.

A master laser light pulse generated as an output from the master laser 11 is provided via the half mirror M11 to the illumination light pulse generator 14. The bias voltage $Vb(1)$ is applied to the illumination light pulse generator 14. An illumination light pulse is generated as an output from the illumination light pulse generator 14. The illumination light pulse passes through the half mirror M21 and further through the object under measurement 2, and then becomes a light pulse under measurement, which is provided to the signal-under-measurement generator 16. In addition, the illumination light pulse is reflected from the half mirror M21 and further from the mirror M22, and then provided to the monitor signal generator 18.

Moreover, a slave laser light pulse generated as an output from the slave laser 12 is provided via the half mirrors M12, M23 to the signal-under-measurement generator 16. The slave laser light pulse passes through the half mirror M12, and is reflected from the half mirror M23 and the mirror M24 and then provided to the monitor signal generator 18.

A signal under measurement (which is a current signal) is generated as an output from the signal-under-measurement generator 16 and is converted, while being amplified by the first I/V amplifier 22, into a voltage signal, which is provided to the waveform display device 40. A monitor signal (which is a current signal) is generated as an output from the monitor signal generator 18 and is converted, while being amplified by the second I/V amplifier 24, into a voltage signal, which is provided to the waveform display device 40.

Note that the master laser light pulse and the slave laser light pulse are reflected from the half mirrors M11, M12, respectively, and are provided to the trigger signal generator 32. Note again that the trigger signal generator 32 generates an output trigger signal at a point in time when simultaneously receiving the master laser light pulse and the slave laser light pulse, and that the trigger signal is provided to the waveform display device 40.

The signal under measurement and the trigger signal are provided to the signal measuring unit 42, and the monitor signal and the trigger signal are provided to the amplitude measuring unit 414.

Here, the amplitude measuring unit 414 measures the amplitude of the monitor signal, $Vm(1)$ (S110: measurement at the first time) (refer to FIG. 21(*a*)). Note that the environmental temperature and the like at the time of measuring the amplitude of the monitor signal, $Vm(1)$ are assumed to be equal to those at the time of acquiring information recorded by the monitor and bias amplitude characteristic recording unit 412. In such a situation, referring to FIG. 21(*a*), the coordinates ($Vb(1)$, $Vm(1)$) are on a solid line curve representing information recorded by the monitor and bias amplitude characteristic recording unit 412.

Further, the signal measuring unit 42 measures the output point (e.g., output start point) of the signal under measurement relative to the trigger signal, and the amplitude of the signal under measurement (S112: measurement at the first time).

The measurement result $Vm(1)$ obtained by the amplitude measuring unit 414 is recorded in the reference amplitude recording unit 415. The measurement result obtained by the signal measuring unit 42 is displayed on the display unit 43.

After a certain period of time has elapsed after the signal under measurement has been measured (S112: measurement at the first time), the amplitude measuring unit 414 measures the amplitude of the monitor signal $Vm(2)$ (S122: measurement at the second time) (refer to FIG. 21(*a*)), however, with the bias voltage $Vb(1)$ remaining unchanged.

Although the bias voltage $Vb(1)$ remains unchanged, the amplitude of the monitor signal varies from $Vm(1)$ to $Vm(2)$ owing to variations of environmental temperature and the like. This is thought to be because the relationship of the amplitude of the monitor signal with respect to the bias voltage is parallel shifted from the curve of solid line to the curve of dotted lines.

The measurement result $Vm(2)$ at the second time obtained by the amplitude measuring unit 414 is recorded in the measurement amplitude recording unit 416.

Based on the information recorded by the monitor and bias amplitude characteristic recording unit 412, the correction value derivation unit 418 derives a correction value of the bias voltage, $\Delta Vb(2)$ for causing the measurement result (information recorded by the measurement amplitude recording unit 416, $Vm(2)$) obtained by the amplitude measuring unit 414 to correspond to the measurement result (information recorded by the reference amplitude recording unit 415, $Vm(1)$) obtained by the amplitude measuring unit 414 before a point in time when the former measurement result is obtained (S124: measurement at the second time).

Referring to FIG. 21(a), if the relationship of the amplitude of the monitor signal with respect to the bias voltage is assumed to be on a curve of dotted lines, then shifting the bias voltage from Vb(1) to Vb(2) allows the amplitude of the monitor signal to correspond to Vm(1). Here, since the dotted lines and the solid line in FIG. 21 can be regarded to be the same in form, Vb(2)−Vb(1) (variation value of the bias voltage, required for varying the amplitude of the monitor signal from Vm(2) to Vm(1) in the solid line curve) is equal to ΔVb(2).

Thus, based on the information (solid line curve in FIG. 21(a)) recorded by the monitor and bias amplitude characteristic recording unit 412, Vm(2) and Vm(1), the correction value derivation unit 418 derives the value ΔVb(2), and the derived ΔVb(2) is determined to be a correction value of the bias voltage.

The correction value of the bias voltage, ΔVb(2) is provided from the correction derivation unit 418 of the waveform display device 40 to the bias voltage applying unit (amplitude error correction unit) 50. The bias voltage applying unit 50 causes the bias voltage to vary by the correction value ΔVb(2) of the bias voltage. In other words, the bias voltage applying unit 50 adds the correction value ΔVb(2) of the bias voltage to the bias voltage Vb(1), and changes the bias voltage to Vb(2) (=Vb(1)+ΔVb(2)) (S126: measurement at the second time).

Thereafter, the amplitude measuring unit 414 measures the amplitude of the monitor signal, Vm(2)' (S127: measurement at the second time). The value Vm(2)' is substantially equal to Vm(1). The measurement result Vm(2)' obtained by the amplitude measuring unit 414 is recorded in the reference amplitude recording unit 415.

Add to this, the signal measuring unit 42 measures an output point (e.g., output start point) of a signal under measurement relative to a trigger signal, and the amplitude of the signal under measurement (S128: measurement at the second time). The measurement result of the amplitude of the signal under measurement is what has been acquired for the signal under measurement whose amplitude is corrected by the bias voltage applying unit 50.

Further, after a certain period of time has elapsed after the signal under measurement has been measured (S128: measurement at the second time), the amplitude measuring unit 414 measures the amplitude of the monitor signal, Vm(3) (S122: measurement at the third time) (refer to FIG. 21(b)), however, with the bias voltage Vb(2) remaining unchanged.

Although the bias voltage Vb(2) remains unchanged, the amplitude of the monitor signal varies from Vm(2)' to Vm(3) owing to variations of the environmental temperature and the like. The relationship of the amplitude of the monitor signal with respect to the bias voltage is thought to be parallel shifted from the dotted line curve (what is on the left side) to the dotted line curve (what is on the right side).

The measurement result Vm(3) at the third time obtained by the amplitude measuring unit 414 is recorded in the measurement amplitude recording unit 416.

Based on the information recorded by the monitor and bias amplitude characteristic recording unit 412, the correction value derivation unit 418 derives a correction value of the bias voltage, ΔVb(3), the correction value for causing the measurement result (information recorded by the measurement amplitude recording unit 416, Vm(3)) obtained by the amplitude measuring unit 414 to correspond to the measurement result (information recorded by the reference amplitude recording unit 415, Vm(2)') obtained by the amplitude measuring unit 414 before a point in time when the former measurement result is obtained (S124: measurement at the third time).

Referring to FIG. 21(b), if the relationship of the amplitude of the monitor signal with respect to the bias voltage is assumed to be on a dotted line curve (what is on the right side), then shifting the bias voltage from Vb(2) to Vb(3) allows the amplitude of the monitor signal to correspond to Vm(2)'. Here, since the dotted lines and the solid line in FIG. 21 can be regarded to be the same in form, Vb(3)−Vb(2) (variation value of the bias voltage, required for varying the amplitude of the monitor signal from Vm(3) to Vm(2)' in the solid line curve) is equal to ΔVb(3).

Thus, based on the information (solid line curve in FIG. 21(b)) recorded by the monitor and bias amplitude characteristic recording unit 412, Vm(3) and Vm(2)', the correction value derivation unit 418 derives the value ΔVb(3), and the derived ΔVb(3) is determined to be a correction value of the bias voltage.

The correction value of the bias voltage, ΔVb(3) is provided from the correction value derivation unit 418 of the waveform display device 40 to the bias voltage applying unit (amplitude error correction unit) 50. The bias voltage applying unit 50 causes the bias voltage to vary by the correction value ΔVb(3) of the bias voltage. In other words, the bias voltage applying unit 50 adds the correction value ΔVb(3) of the bias voltage to the bias voltage Vb(2), and changes the bias voltage to Vb(3) (=Vb(2)+ΔVb(3)) (S126: measurement at the third time).

Thereafter, the amplitude measuring unit 414 measures the amplitude of the monitor signal, Vm(3)' (S127: measurement at the third time). The value Vm(3)' is substantially equal to Vm(2)'. The value Vm(2)' is substantially equal to Vm(1), thereby resulting in the value Vm(3)' being substantially equal to Vm(1). The measurement result Vm(3)' obtained by the amplitude measuring unit 414 is recorded in the reference amplitude recording unit 415.

Add to this, the signal measuring unit 42 measures the output point (e.g., output start point) of the signal under measurement relative to the trigger signal, and the amplitude of the signal under measurement (S128: measurement at the third time). The measurement result of the amplitude of the signal under measurement is what has been acquired for the signal under measurement whose amplitude is corrected by the bias voltage applying unit 50.

According to the fifth embodiment, an error of the measurement result (amplitude of the signal under measurement) of the object under measurement 2 by means of light, such as terahertz light (illumination light pulse)—the error resulting from the changed ambient temperature (environmental temperature) and the like of the light measurement apparatus 1—can be canceled by varying by ΔVb the bias voltage that is applied to the illumination light pulse generator 14 and thus, the amplitude of the signal under measurement can be obtained correctly.

Figure 26:
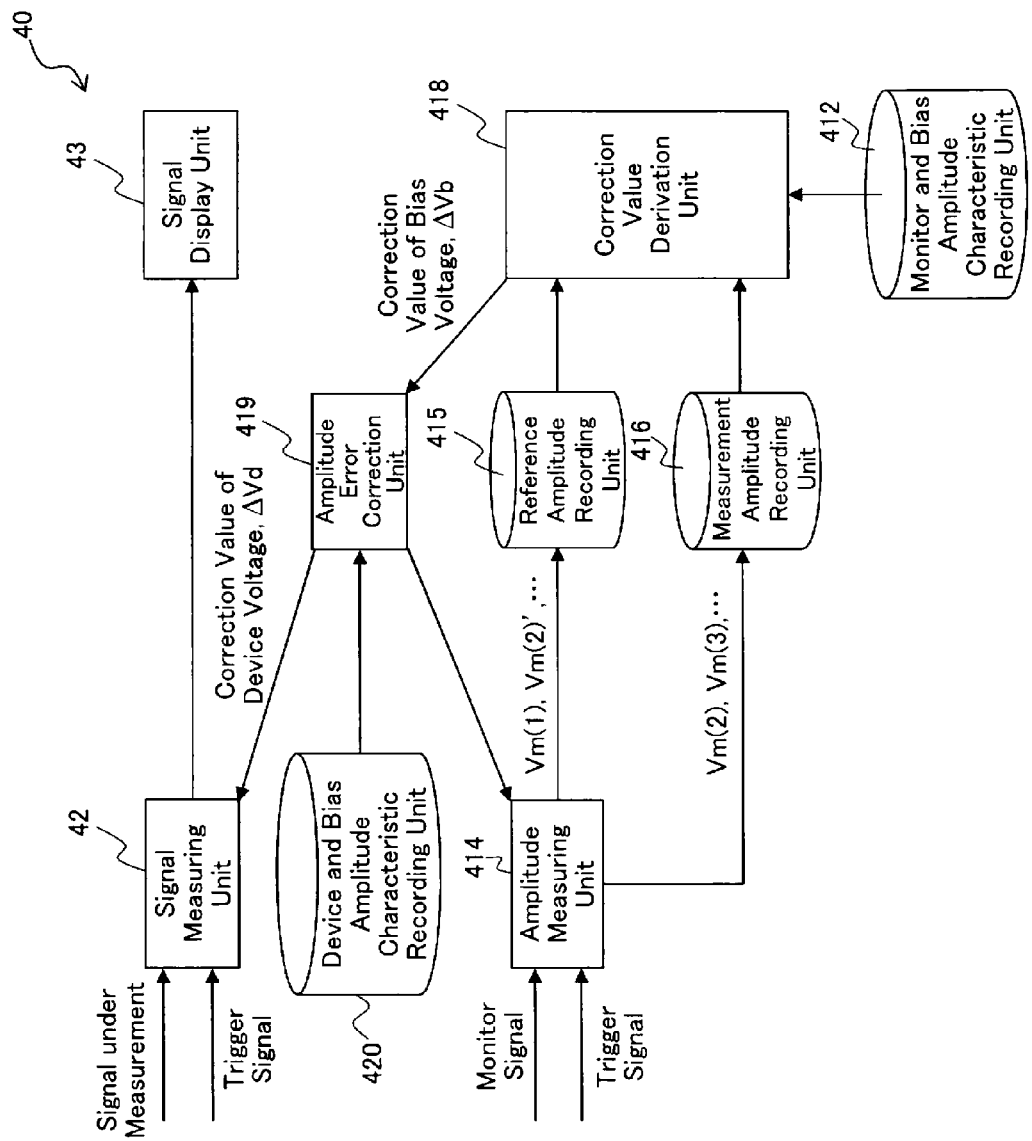
FIG. 26 is a functional block diagram showing a configuration of the waveform display device 40 according to a modification (where amplitude error is corrected without varying the bias voltage) of the fifth embodiment.

Note that although in the fifth embodiment the amplitude error of the signal under measurement has been corrected by varying the bias voltage by ΔVb, the amplitude error can also be corrected without varying the bias voltage. FIG. 26 is a functional block diagram showing a configuration of the waveform display device 40 according to a modification (where amplitude error is corrected without varying the bias voltage) of the fifth embodiment.

The waveform display device 40 according to the modification of the fifth embodiment is configured to further add an amplitude error correction unit 419 and a device and bias amplitude characteristic recording unit 420 to the waveform display device 40 according to the fifth embodiment.

The device and bias amplitude characteristic recording unit 420 records the relationship of the amplitude of the output from the signal-under-measurement generator 16 with respect to the bias voltage that is applied to the illumination light pulse generator 14. The amplitude of the output from the signal-under-measurement generator 16 may in some cases vary according to changes of e.g., the ambient temperature (environmental temperature) of the light measurement apparatus 1, even if the bias voltage is constant that is applied to the illumination light pulse generator 14. Thus, the above described relationship can be acquired by measuring the amplitude of the output from the signal-under-measurement generator 16 while varying the bias voltage that is applied to the illumination light pulse generator 14 with the environmental temperature and the like maintained constant and with the object under measurement 2 placed out of the light measurement apparatus 1. Note that the relationship to be recorded may be data between a bias voltage that is applied to the illumination light pulse generator 14 and the amplitude of an output from the signal-under-measurement generator 16, or alternatively, may be a mathematical expression showing a relationship between the bias voltage applied to the illumination light pulse generator 14 and the amplitude of the output from the signal-under-measurement generator 16.

Figure 27:
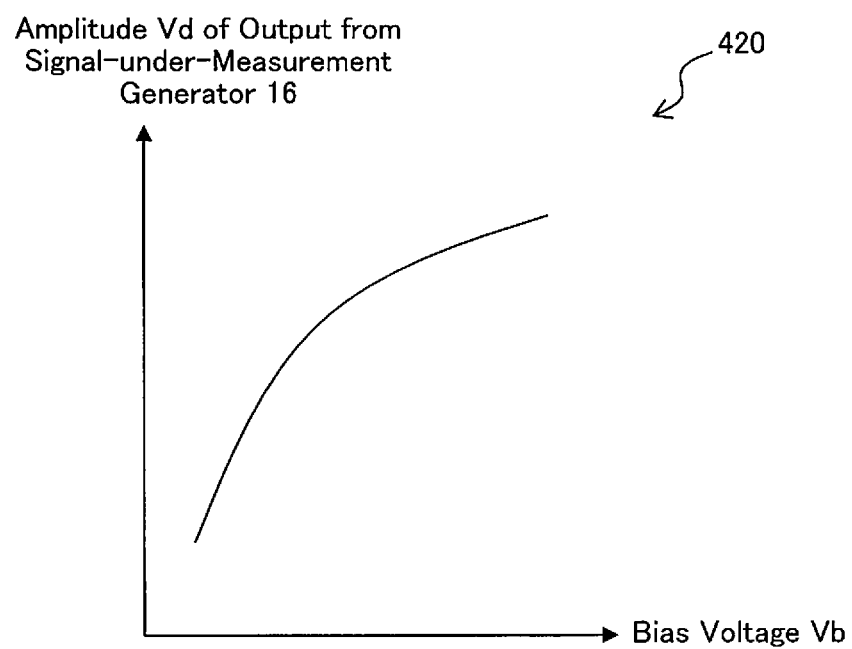
FIG. 27 is a graph showing an example of information recorded by the device and bias amplitude characteristic recording unit 420.

FIG. 27 is a graph showing an example of information recorded by the device and bias amplitude characteristic recording unit 420. As the bias voltage rises that is applied to the illumination light pulse generator 14, the amplitude Vd of the output from the signal-under-measurement generator 16 (where the object under measurement 2 is placed out of the light measurement apparatus 1) varies (e.g., increases monotonously). Note that although, in FIG. 27, the amplitude Vd of the output from the signal-under-measurement generator 16 is shown in a curve, the amplitude is also thought to follow in a straight line.

The amplitude error correction unit 419 receives a correction value ΔVb of the bias voltage from the correction value derivation unit 418. Further, based on the information recorded by the device and bias amplitude characteristic recording unit 420, the amplitude error correction unit 419 corrects by a variation value ΔVd the measurement result obtained by the signal measuring unit 42, the variation value being of the amplitude of the signal under measurement and corresponding to the correction value ΔVb of the bias voltage.

Figure 28:
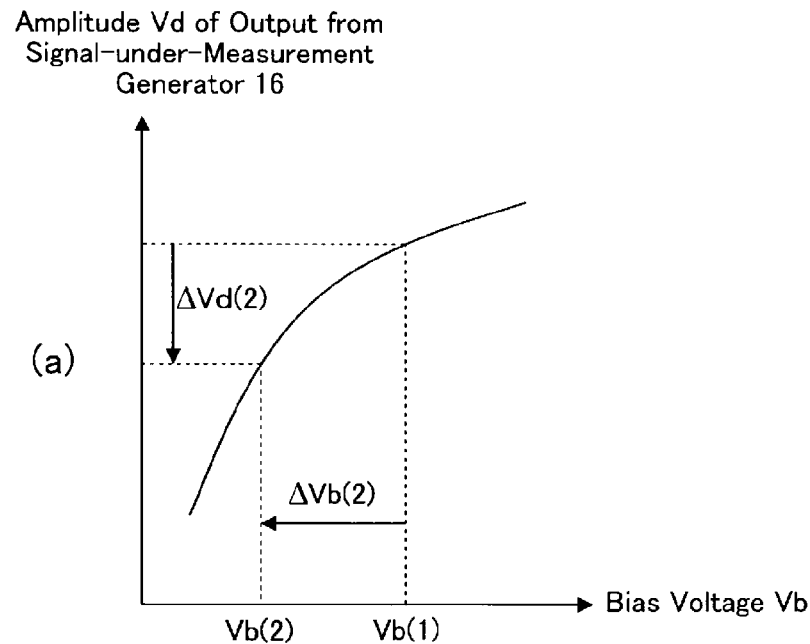
FIG. 28 is a set of graphs each showing the variation value ΔVd of the amplitude of the signal under measurement, derived by the amplitude error correction unit 419.
Figure 28:
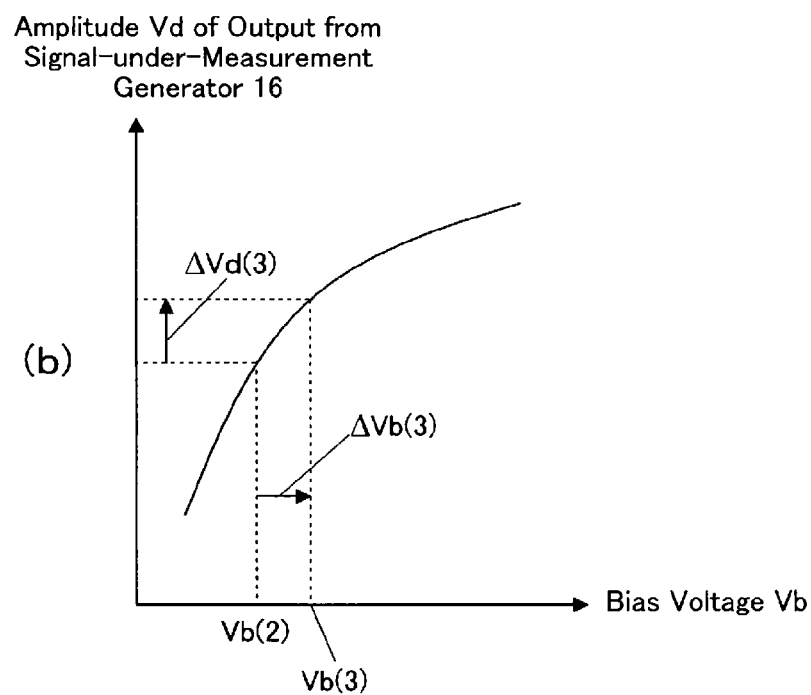

FIG. 28 is a set of graphs each showing the variation value ΔVd of the amplitude of the signal under measurement, derived by the amplitude error correction unit 419. Note that the solid line curve in FIG. 28 is information (refer to FIG. 27) recorded by the device and bias amplitude characteristic recording unit 420.

FIG. 28(a) is a graph showing a variation value ΔVd(2) of the amplitude of the signal under measurement, the value corresponding to a correction value ΔVb(2) of the bias voltage.

The amplitude error correction unit 419 receives from the correction value derivation unit 418 the correction value ΔVb(2) of the bias voltage corresponding to the fact that the bias voltage is caused to vary from Vb(1) to Vb(2). And then, the amplitude error correction unit 419 derives the difference ΔVd(2) (<0) between the amplitude of the signal under measurement corresponding to Vb(2) and that of the signal under measurement corresponding to Vb(1). Further, the amplitude error correction unit 419 adds ΔVd(2) to the measurement result of the amplitude of the signal under measurement, obtained by the signal measuring unit 42, and corrects the measurement result of the amplitude of the signal under measurement. This allows, without varying the bias voltage, for correction of the measurement result of the amplitude of the signal under measurement, the amplitude corresponding to the change of the bias voltage from Vb(1) to Vb(2).

Note that the amplitude measuring unit 414 measures the amplitude of the monitor signal just before the correction of the measurement result of the amplitude of the signal under measurement. The amplitude error correction unit 419 adds the value Vm(1)−Vm(2) to the measurement result, yielding Vm(2)'. It will suffice if the amplitude error correction unit 419 receives the values Vm(1) and Vm(2) from the correction value derivation unit 418.

FIG. 28(b) is a graph showing the variation value ΔVd(3) of the amplitude of the signal under measurement, the value corresponding to the correction value ΔVb(3) of the bias voltage.

The amplitude error correction unit 419 receives from the correction value derivation unit 418 the correction value ΔVb(3) of the bias voltage corresponding to the fact that the bias voltage is caused to vary from Vb(2) to Vb(3). And then, the amplitude error correction unit 419 derives the difference ΔVd(3) 0) between the amplitude of the signal under measurement corresponding to Vb(3) and that of the signal under measurement corresponding to Vb(2). Further, the amplitude error correction unit 419 adds ΔVd(3) to the measurement result (what is the one in which the correction to add ΔVd(2) has already been made) of the amplitude of the signal under measurement, obtained by the signal measuring unit 42, and corrects the measurement result of the amplitude of the signal under measurement. This allows, without varying the bias voltage, for correction of the measurement result of the amplitude of the signal under measurement, the amplitude corresponding to the change of the bias voltage from Vb(2) to Vb(3).

Note that the amplitude measuring unit 414 measures the amplitude of the monitor signal just before the correction of the measurement result of the amplitude of the signal under measurement. The amplitude error correction unit 419 adds the value Vm(2)'−Vm(3) to the measurement result, yielding Vm(3)'. It will suffice if the amplitude error correction unit 419 receives the values Vm(2)' and Vm(3) from the correction value derivation unit 418.

Sixth Embodiment

The light measurement apparatus 1 according to the sixth embodiment differs from the apparatus 1 of the fifth embodiment in that the signal-under-measurement generator 16 doubles as a monitor signal generator.

Figure 22:
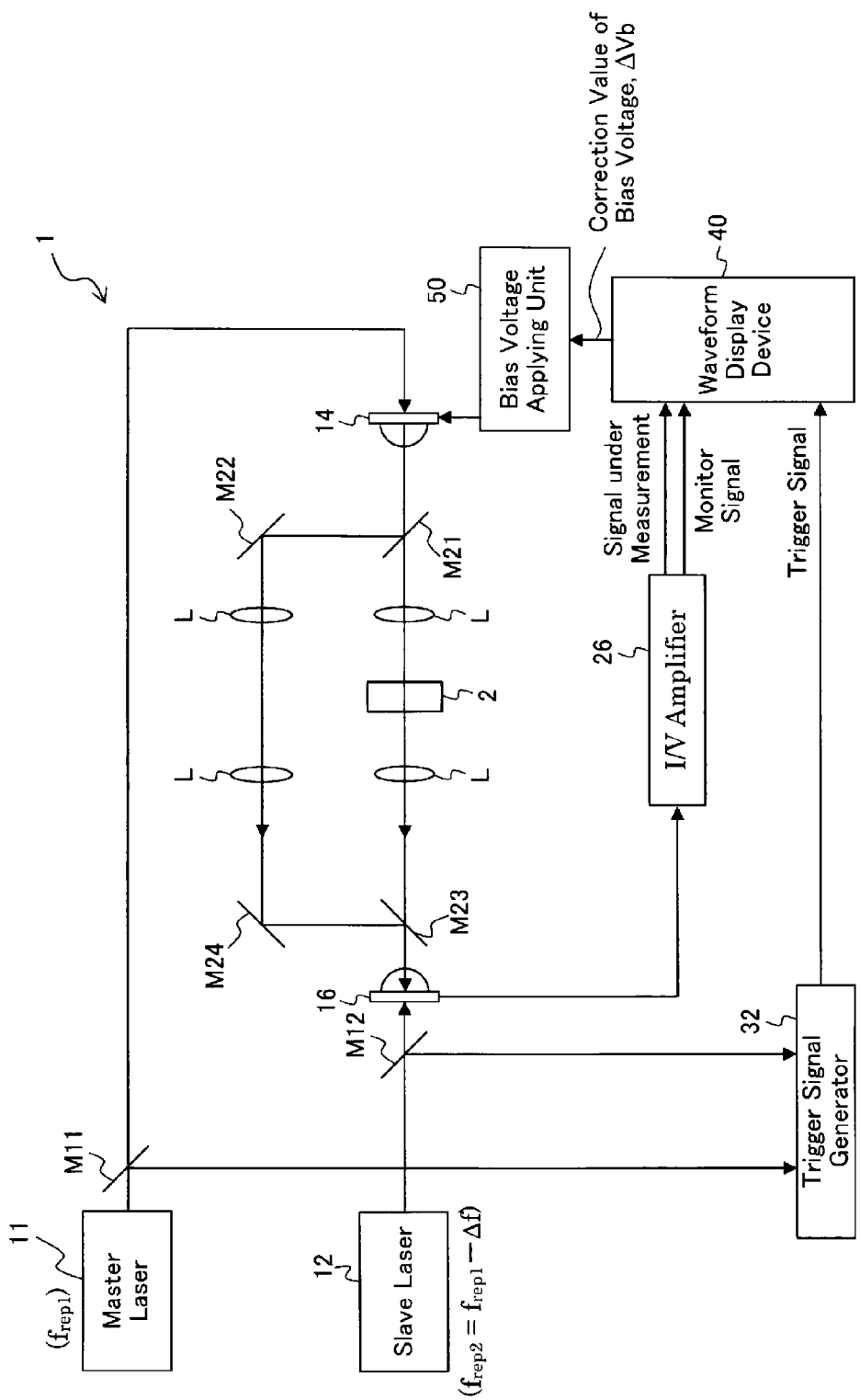
FIG. 22 is a diagram showing a configuration of the light measurement apparatus 1 according to the sixth embodiment of the present invention.

FIG. 22 is a diagram showing a configuration of the light measurement apparatus 1 according to the sixth embodiment of the present invention. The light measurement apparatus 1 according to the sixth embodiment includes the master laser 11, the slave laser 12, the half mirrors M11, M12, M21 and M23, the mirrors M22, M24, the lens L, the illumination light pulse generator 14, the signal-under-measurement generator 16, the I/V amplifier 26, the trigger signal generator 32, the waveform display device 40, and the bias voltage applying unit (amplitude error correction unit) 50. Elements similar to the fifth embodiment are designated hereinafter with the same reference numerals as those of the fifth embodiment, and their description will not be provided herein.

The master laser 11, the slave laser 12, the half mirrors M11, M12, the lens L, the illumination light pulse generator 14, the trigger signal generator 32, the waveform display device 40, and the bias voltage applying unit (amplitude error correction unit) 50, are the same as those in the fifth embodiment and thus, their description will not be provided.

A slave laser light pulse generated as an output from the slave laser 12 passes through the half mirror M12 and is provided to the signal-under-measurement generator 16.

An illumination light pulse is separated by the half mirror M21 into light to be directed toward the object under measurement 2 and light not to be directed theretoward. The former (light to be directed toward the object under measurement 2) passes through the object under measurement 2 (light pulse under measurement) and is provided to the signal-under-measurement generator 16, which receives the light pulse under measurement and generates as an output a signal under measurement. The latter (light not to be directed toward the object under measurement 2: illumination light pulse) is reflected from the mirrors M22, M24 and the half mirror M23, and then provided to the signal-under-measurement generator 16. The signal-under-measurement generator 16 receives the latter (illumination light pulse) and generates as an output a monitor signal.

In this way, the signal-under-measurement generator 16 generates as an output a signal under measurement, and also a monitor signal. In other words, the signal-under-measurement generator 16 doubles as a monitor signal generator.

The I/V amplifier 26 converts, while amplifying the signal under measurement and the monitor signal each generated as an output from the signal-under-measurement generator 16, the amplified signals into voltage signals, which are provided to the waveform display device 40.

Figure 23:
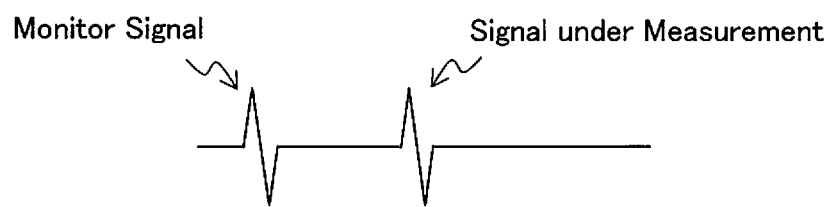
FIG. 23 is a diagram showing a waveform of the signal under measurement and the monitor signal each generated as an output from the I/V amplifier 26 according to the sixth embodiment.

FIG. 23 is a diagram showing a waveform of the signal under measurement and the monitor signal each generated as an output from the I/V amplifier 26 according to the sixth embodiment. Note that in FIG. 23, the vertical axis represents voltage and the horizontal axis, time. Referring to FIG. 23, the signal under measurement and the monitor signal do not overlap with each other in the time domain. For this purpose, it will suffice if the light pulse under measurement and the illumination light pulse may be received by the signal-under-measurement generator 16 in such a way that the pulses do not overlap with each other in the time domain. In the sixth embodiment, by increasing the difference in optical path between an optical path where the object under measurement 2 is present (path of light passing through the object under measurement 2) and an optical path where the object under measurement 2 is not present (path of light reflected from the mirrors M22, M24)—each path being located between the illumination light pulse generator 14 and the signal-under-measurement generator 16—the light pulse under measurement and the illumination light pulse are configured or designed to be received by the signal-under-measurement generator 16 in such a way that both pulses do not overlap with each other in the time domain.

The operation of the sixth embodiment is the same as that of the fifth embodiment.

According to the sixth embodiment, advantageous effects similar to those of the fifth embodiment can be achieved without using the monitor signal generator 18.

Note that as with the modification (refer to FIG. 26) of the fifth embodiment, also in the sixth embodiment, the amplitude errors can be corrected without causing the bias voltage to vary.

Seventh Embodiment

The light measurement apparatus 1 according to the seventh embodiment differs from the apparatus 1 of the sixth embodiment in that the former includes an optical system (the mirrors M21, M22, M23, M24, and stages Stg 1, Stg 2) in which any selected one of a light pulse under measurement and an illumination light pulse is provided to the signal-under-measurement generator 16.

Figure 24:
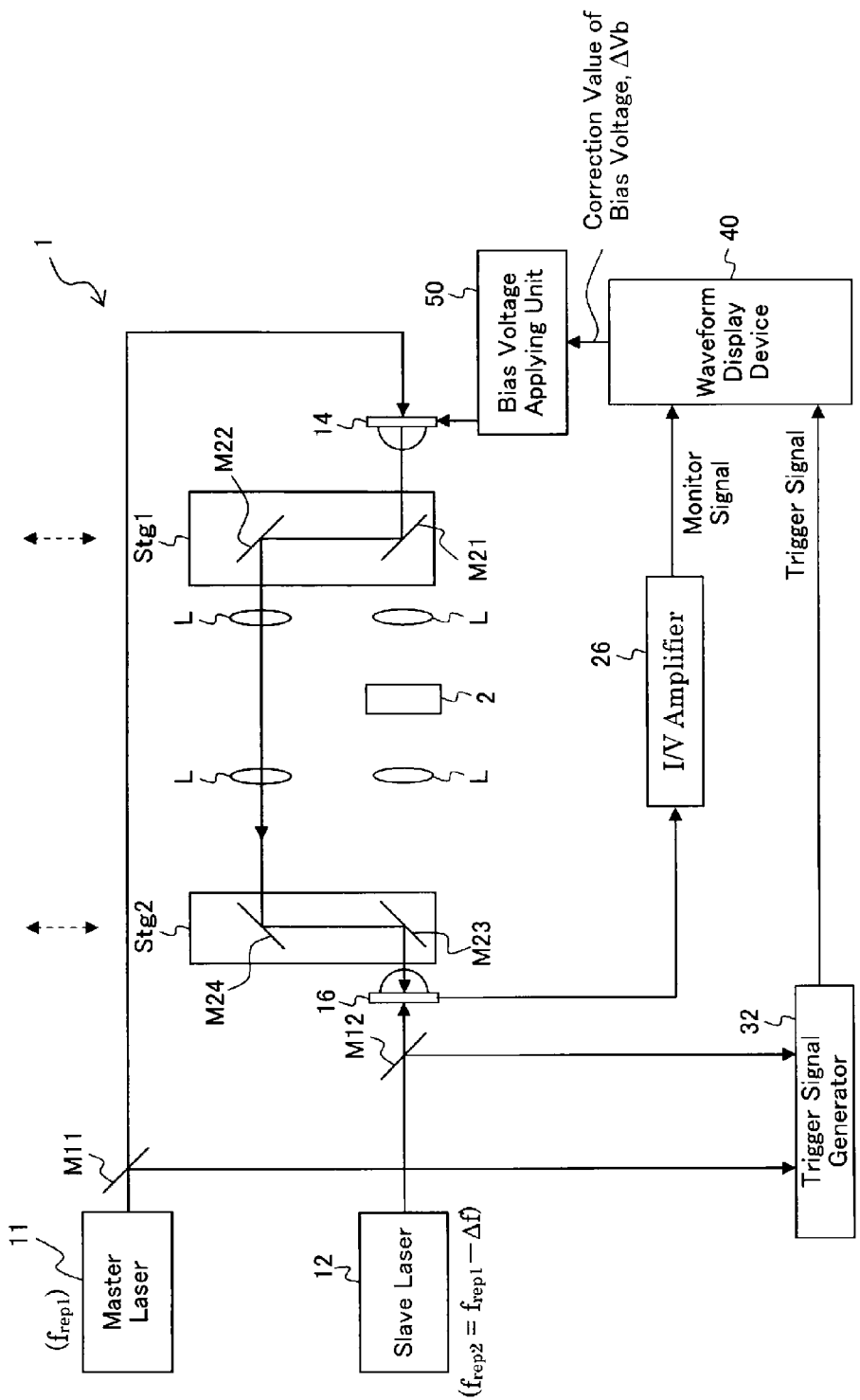
FIG. 24 is a diagram showing a configuration of the light measurement apparatus 1 according to the seventh embodiment of the present invention (at the time when the monitor signal is acquired)
Figure 25:
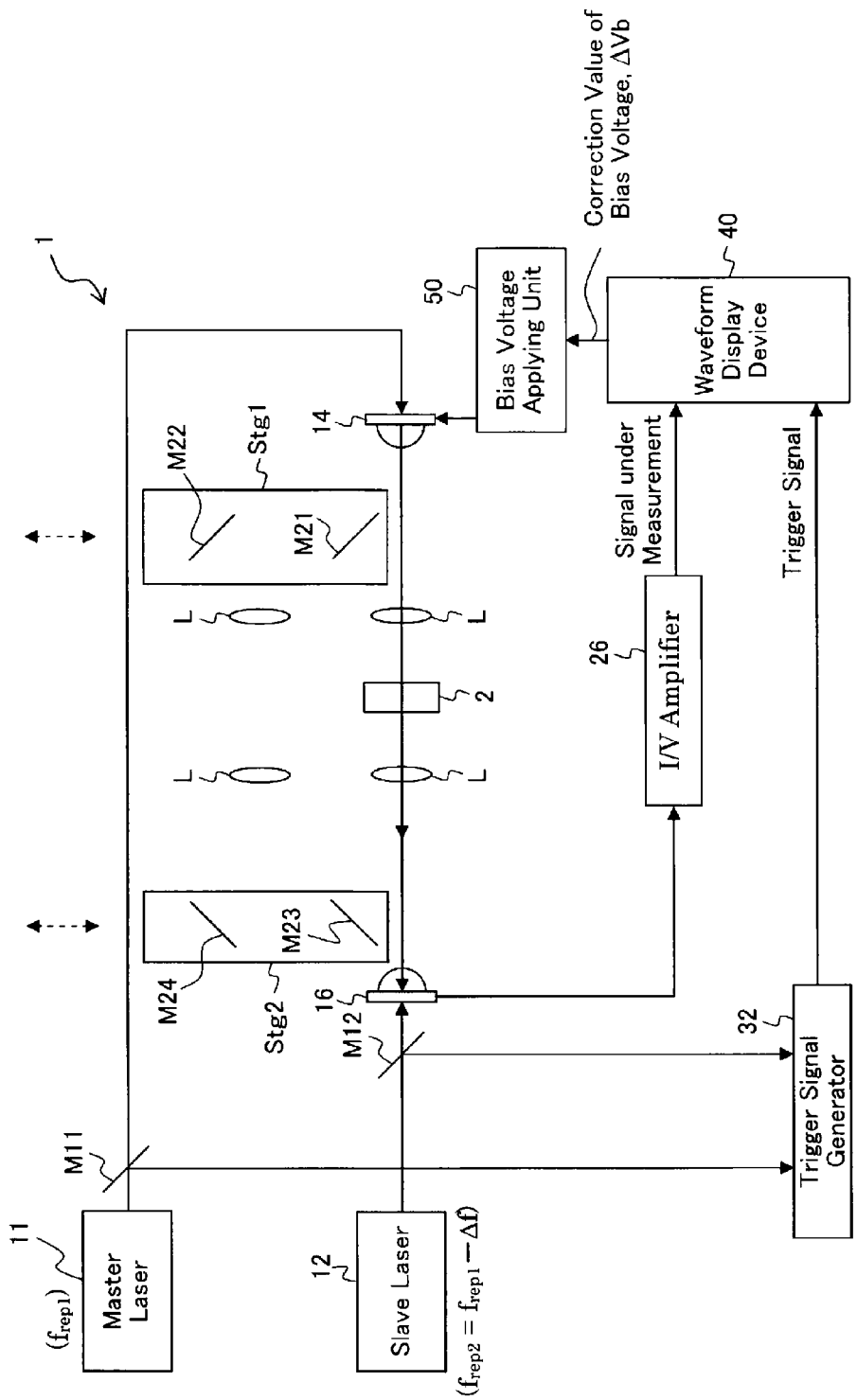
FIG. 25 is a diagram showing a configuration of the light measurement apparatus 1 according to the seventh embodiment of the present invention (at the time when the signal under measurement is acquired)

FIG. 24 is a diagram showing a configuration of the light measurement apparatus 1 according to the seventh embodiment of the present invention (at the time when the monitor signal is acquired). FIG. 25 is a diagram showing a configuration of the light measurement apparatus 1 according to the seventh embodiment of the present invention (at the time when the signal under measurement is acquired). The light measurement apparatus 1 according to the seventh embodiment includes the master laser 11, the slave laser 12, the half mirrors M11, M12, the mirrors M21, M23, M22 and M24, the stages Stg1, Stg2, the lens L, the illumination light pulse generator 14, the signal-under-measurement generator 16, the I/V amplifier 26, the trigger signal generator 32, the waveform display device 40, and the bias voltage applying unit (amplitude error correction unit) 50. Elements similar to the sixth embodiment are designated hereinafter with the same reference numerals as those of the sixth embodiment, and their description will not be provided herein.

The master laser 11, the slave laser 12, the half mirrors M11, M12, the lens L, the illumination light pulse generator 14, the signal-under-measurement generator 16, the I/V amplifier 26, the trigger signal generator 32, the waveform display device 40, and the bias voltage applying unit (amplitude error correction unit) 50, are the same as those in the sixth embodiment and thus, their description will not be provided.

Although in the sixth embodiment, reference numerals M21 and M23 each represent a half mirror, they represent a mirror in the seventh embodiment. The mirrors M21, M22 are mounted on the stage Stg1, while the mirrors M23, M24 are mounted on the stage Stg2.

The stage Stg1 allows the mirror M21 to move to a place where the mirror reflects an illumination light pulse (refer to FIG. 24) or alternatively, where the mirror does not reflect the illumination light pulse (refer to FIG. 25). The stage Stg2 allows the mirror M23 to move to a place where the mirror reflects an illumination light pulse (refer to FIG. 24) or alternatively, where the mirror does not reflect the illumination light pulse (refer to FIG. 25). Note that dotted arrows in FIG. 24 and FIG. 25 indicate directions in which the stage Stg1 and the stage Stg2 are allowed to move.

Referring to FIG. 24, in situations where the stage Stg1 and the stage Stg2 causes the mirror M21 and the mirror M23 to move, respectively, to the place where they reflect an illumination light pulse, the illumination light pulse is provided from the illumination light pulse generator 14 to the signal-under-measurement generator 16. Thus, the signal-under-measurement generator 16 generates as an output a monitor signal.

Referring to FIG. 25, in situations where the stage Stg1 and the stage Stg2 causes the mirror M21 and the mirror M23 to move, respectively, to the place where they do not reflect an illumination light pulse, the light pulse under measurement is provided to the signal-under-measurement generator 16. Thus, the signal-under-measurement generator 16 generates as an output a signal under measurement.

This causes the light pulse under measurement and the illumination light pulse to be received by the signal-under-measurement generator 16 in such a way that the pulses do not overlap with each other in the time domain. In the seventh embodiment, the difference in optical path may be zero if it is a constant value between an optical path (refer to FIG. 25) where the object under measurement 2 is present and that (refer to FIG. 24) where the object under measurement 2 is not present, each path being located between the illumination light pulse generator 14 and the signal-under-measurement generator 16.

The operation of the seventh embodiment is similar to that of the fifth embodiment.

According to the seventh embodiment, advantageous effects similar to those of the fifth embodiment are achieved without using the monitor signal generator 18.

Note that, as with the modifications of the fifth embodiment (refer to FIG. 26), also in the seventh embodiment, error correction can be made without causing the bias voltage to vary.

Eighth Embodiment

The eighth embodiment differs from the fifth embodiment in that an error in measurement of an amplitude of the signal under measurement is corrected by measuring an ambient temperature (environmental temperature) of the light measurement apparatus 1 without using a monitor signal.

Figure 29:
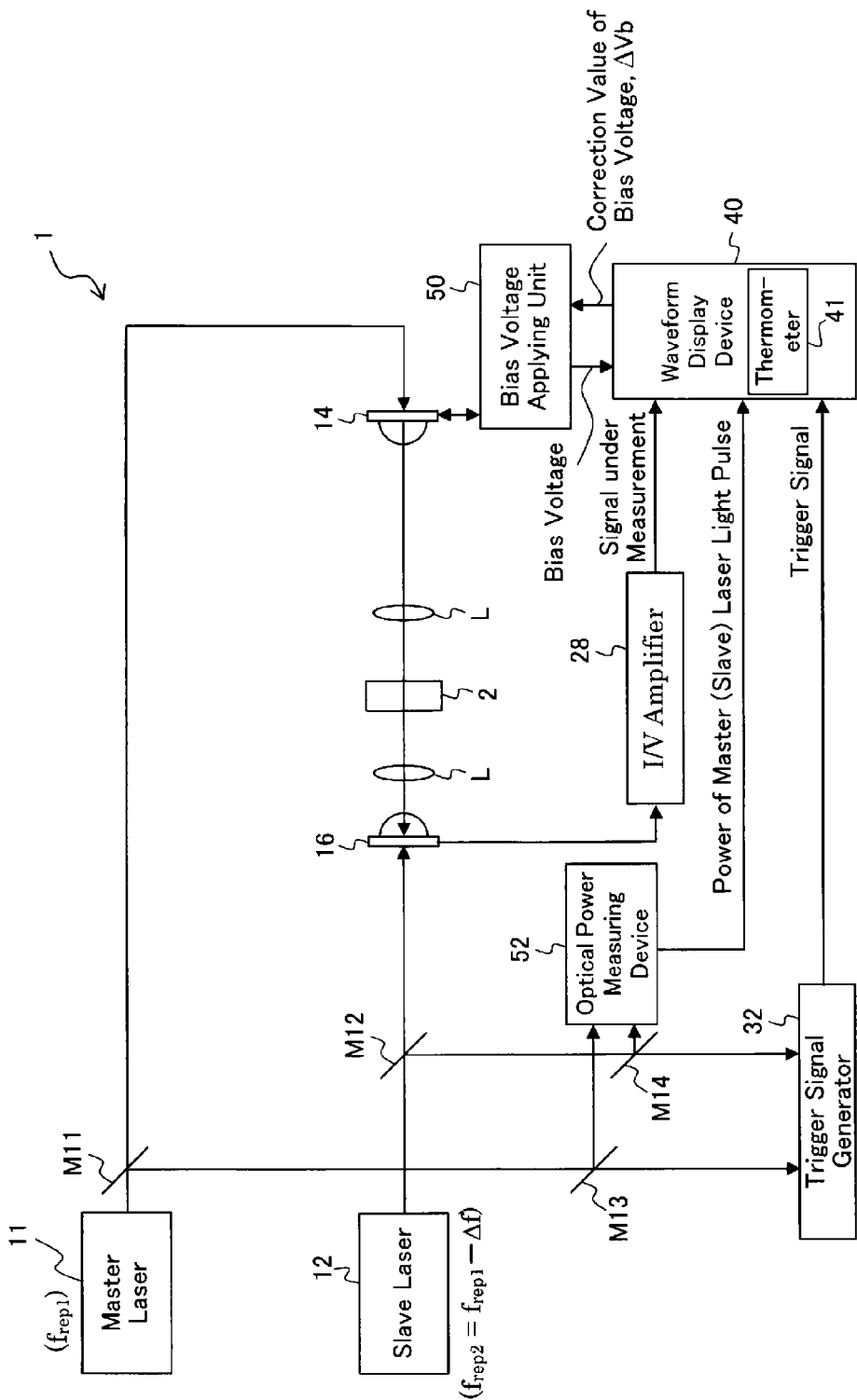
FIG. 29 is a diagram showing a configuration of the light measurement apparatus 1 according to the eighth embodiment of the present invention.

FIG. 29 is a diagram showing a configuration of the light measurement apparatus 1 according to the eighth embodiment of the present invention. The light measurement apparatus 1 according to the eighth embodiment includes the master laser 11, the slave laser 12, the half mirrors M11, M12, M13 and M14, the lens L, the illumination light pulse generator 14, the signal-under-measurement generator 16, the I/V amplifier 28, the trigger signal generator 32, the waveform display device 40, the bias voltage applying unit (amplitude error correction unit) 50, and an optical power measuring device 52. Elements similar to the fifth embodiment are designated hereinafter with the same reference numerals as those of the fifth embodiment, and their description will not be provided herein.

The master laser 11, the slave laser 12, the half mirrors M11, M12, the lens L, the illumination light pulse generator 14, the signal-under-measurement generator 16, the trigger signal generator 32, are the same as those in the fifth embodiment and thus, their description will not be provided.

The I/V amplifier 28, while amplifying the signal under measurement (which is a current signal) generated as an output from the signal-under-measurement generator 16, converts the amplified signal into a voltage signal, which is provided to the waveform display device 40.

The bias voltage applying unit (amplitude error correction unit) 50 applies a bias voltage to the illumination light pulse generator 14. The bias voltage applying unit 50 corrects the amplitude of a signal under measurement by causing a bias voltage that is applied to the illumination light pulse generator 14 to vary by a result (bias voltage correction value $\Delta Vb$) derived by a correction value derivation unit 426 of the waveform display device 40. The amplitude of the signal under measurement varies according to the amplitude of a light pulse under measurement; the amplitude of the light pulse under measurement varies according to the amplitude of an illumination light pulse; and the amplitude of the illumination light pulse varies according to a bias voltage that is applied to the illumination light pulse generator 14. Thus, varying the bias voltage that is applied to the illumination light pulse generator 14 allows for correction of the amplitude of the signal under measurement.

Note that the bias voltage applying unit 50 measures the bias voltage that is applied to the illumination light pulse generator 14, to provide the measured voltage to the correction value derivation unit 426 of the waveform display device 40.

The half mirror M13 partially guides to the optical power measuring unit 52 the master laser light pulse directing from the half mirror M11 toward the trigger signal generator 32.

The half mirror M14 partially guides to the light power measuring unit 52 the slave laser light pulse directing from the half mirror M12 toward the trigger signal generator 32.

The optical power measuring unit 52 measures the power of the master laser light pulse and the slave laser light pulse to provide the measured power to the waveform display device 40.

The waveform display device 40 displays a waveform of a signal under measurement.

Figure 30:
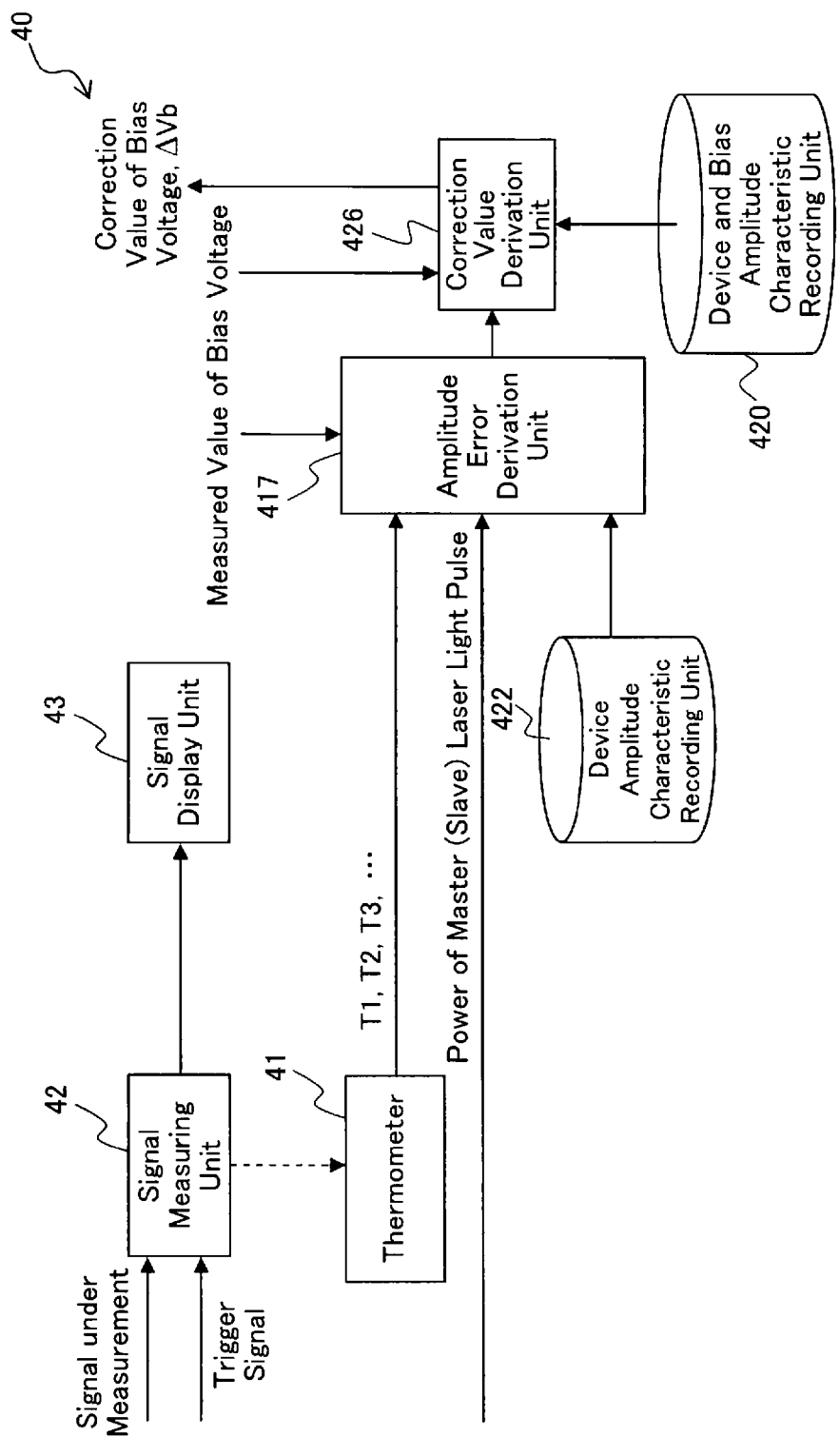
FIG. 30 is a functional block diagram showing a configuration of the waveform display device 40 according to the eighth embodiment.

FIG. 30 is a functional block diagram showing a configuration of the waveform display device 40 according to the eighth embodiment. The waveform display device 40 according to the eighth embodiment has the thermometer 41, the signal measuring unit 42, the signal display unit 43, an amplitude error derivation unit 417, the device and bias amplitude characteristic recording unit 420, a device amplitude characteristic recording unit 422, and the correction value derivation unit 426. The signal measuring unit 42 and the signal display unit 43 are the same as those in the fifth embodiment, and their description will not be provided. The signal measuring unit 42, however, communicates to the thermometer 41 an instruction that the signal measuring unit 42 starts measurement of a signal under measurement and makes measurements at a plurality of times.

The thermometer 41, at a point in time when receiving from the signal measuring unit 42 the instruction that the signal measuring unit 42 starts the measurement of the signal under measurement, measures the ambient temperatures of the light measurement apparatus 1 (environmental temperatures T1, T2, T3, . . . ), and provides them to the amplitude error derivation unit 417. For example, the environmental temperature of the signal under measurement at the first time measurement is represented as T1, the environmental temperature of the signal under measurement at the second time measurement is represented as T2, and the environmental temperature of the signal under measurement at the third time measurement is represented as T3. Strictly speaking, the environmental temperature measurement by the thermometer 41 is made just before measuring the signal under measurement. However, since in general, environmental temperatures will not cause a large momentary variation, environmental temperatures measured just before (or just after) measuring the signal under measurement can be regarded as those at the time of measuring the signal under measurement.

Note that although the foregoing description assumes that the thermometer 41 is contained within the waveform display device 40, the invention is not limited to the fact that the thermometer 41 is placed within the waveform display device 40. The thermometer 41 may be disposed, for example, in the neighborhood of the bias voltage applying unit 50. In other words, it will suffice if the thermometer 41 may be located at any place that allows for measurement of environmental temperatures.

The device and bias amplitude characteristic recording unit 420 is the same as the modification of the fifth embodiment (refer to FIG. 26), and their description will not be provided.

The device amplitude characteristic recording unit 422 records the relationship of the amplitude of the output from the signal-under-measurement generator 16 with respect to the amplitude variation factor. Note, however, that the amplitude variation factor refers to any one or more of the bias voltage applied to the illumination light pulse generator 14, the power of the master laser light pulse, the power of the slave laser light pulse, and the environmental temperature.

The amplitude of the output from the signal-under-measurement generator 16 may in some cases vary according to changes in the amplitude variation factor. Thus, the above described relationship can be acquired by measuring the amplitude of the output from the signal-under-measurement generator 16 while varying one of the amplitude variation factors (e.g., environmental temperature) with the remaining amplitude variation factors (e.g., bias voltage, power of the master laser light pulse and power of the slave laser light pulse) maintained constant and with the object under measurement 2 placed out of the light measurement apparatus 1. Note that the relationship to be recorded may be data between an amplitude variation factor and the amplitude of an output from the signal-under-measurement generator 16, or alternatively, may be a mathematical expression showing a relationship between the amplitude variation factor and the amplitude of the output from the signal-under measurement generator 16.

Figure 31:
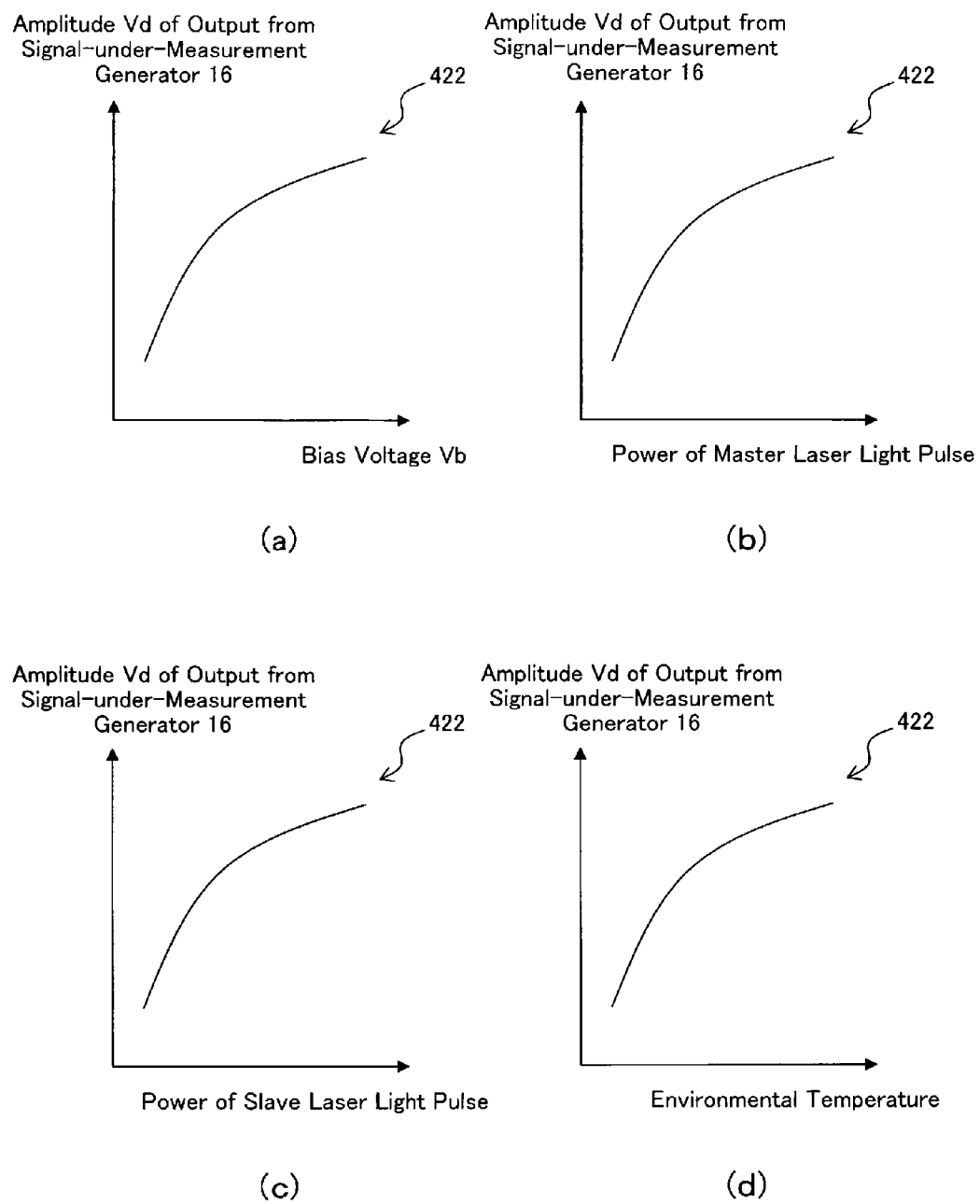
FIG. 31 is a set of graphs showing examples of information recorded by the device amplitude characteristic recording unit 422.

FIG. 31 is a set of graphs showing examples of information recorded by the device amplitude characteristic recording unit 422. The device amplitude characteristic recording unit 422 records the relationship between the bias voltage applied to the illumination light pulse generator 14 and the amplitude Vd of the output from the signal-under-measurement generator 16 (refer to FIG. 31(*a*)), the relationship between the power of the master laser light pulse and the amplitude Vd of the output from the signal-under-measurement generator 16 (refer to FIG. 31(*b*)), the relationship between the power of the slave laser light pulse and the amplitude Vd of the output from the signal-under-measurement generator 16 (refer to FIG. 31(*c*)), and the relationship between the environmental temperature and the amplitude Vd of the output from the signal-under-measurement generator 16 (refer to FIG. 31(*d*)). However, any one has been measured with the object under measurement 2 placed out of the light measurement apparatus 1.

As the amplitude variation factor increases, the amplitude of the output from the signal-under-measurement generator 16, Vd (where, the object under measurement 2 is placed out of the light measurement apparatus 1) varies (e.g., increases monotonously). Note that although, in FIG. 31, the amplitude Vd of the output from the signal-under-measurement generator 16 is shown in a curve, the amplitude is also thought to follow in a straight line.

Figure 33:
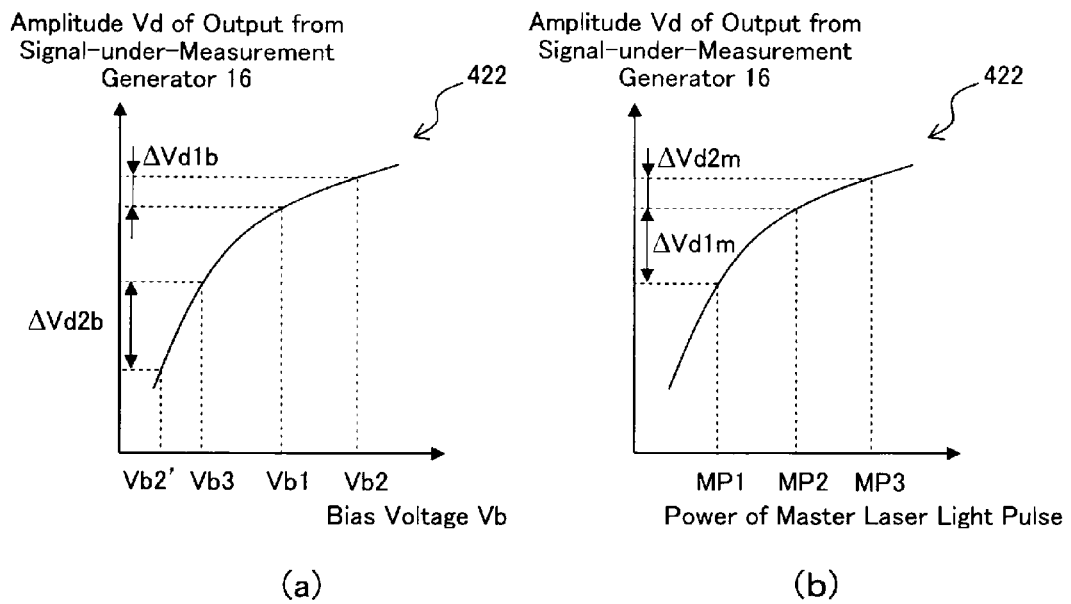
FIG. 33 is a set of graphs for illustrating the amplitude error derived by the amplitude error derivation unit 417.
Figure 33:
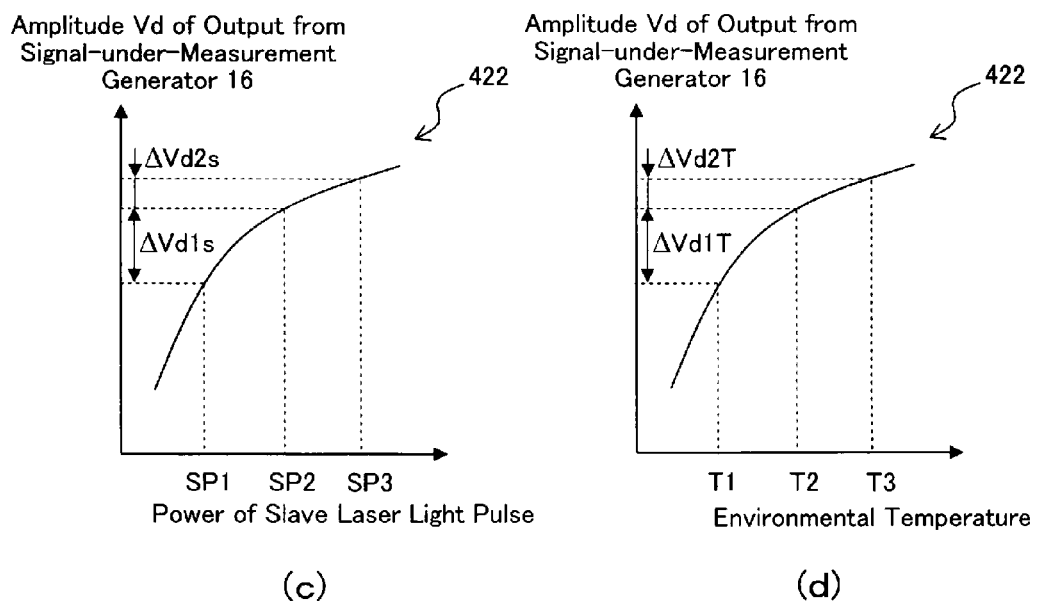

FIG. 33 is a set of graphs for illustrating the amplitude error derived by the amplitude error derivation unit 417. FIG. 33 shows an amplitude error resulting from the variation of the bias voltage (refer to FIG. 33(*a*)), an amplitude error resulting from the variation of the power of the master laser light pulse (refer to FIG. 33(*b*)), an amplitude error resulting from the variation of the power of the slave laser light pulse (refer to FIG. 33(*c*)), and an amplitude error resulting from the variation of the environmental temperature (refer to FIG. 33(*d*)). Note that the solid line curve in FIG. 33 is the same as that in FIG. 31 (information recorded by the device amplitude characteristic recording unit 422).

Based on the information recorded by the device amplitude characteristic recording unit 422, the amplitude error derivation unit 417 derives an error in the amplitude of the signal under measurement between the reference amplitude variation factors (Vb1, MP1, SP1 and T1) (Vb2', MP2, SP2 and T2) and the measurement amplitude variation factors (Vb2, MP2, SP2 and T2) (Vb3, MP3, SP3 and T3) at the point in time when the signal under measurement was measured. Note that the amplitude error derivation unit 417 also acquires another amplitude variation factor, simultaneously with the acquisition of the environmental temperature.

A factor at the point in time when the signal under measurement was measured at the last time may apply to the reference amplitude variation factor.

For example, the amplitude error derivation unit 417 derives an error in the amplitude of the signal under measurement between the measurement amplitude variation factor at a point in time when the signal under measurement has been measured at the first time (reference amplitude variation factors: Vb1, MP1, SP1 and T1) and the measurement amplitude variation factor at a point in time when the signal under measurement has been measured at the second time (Vb2, MP2, SP2 and T2).

Referring to FIG. 33(*a*), the variation of the amplitude of the signal under measurement resulting from the bias voltage varying from Vb1 to Vb2 is $\Delta Vd1b$. Referring to FIG. 33(*b*), the variation of the amplitude of the signal under measurement resulting from the power of the master laser light pulse varying from MP1 to MP2 is $\Delta Vd1m$. Referring to FIG. 33(*c*), the variation of the amplitude of the signal under measurement resulting from the power of the slave laser light pulse varying from SP1 to SP2 is $\Delta Vd1s$. Referring to FIG. 33(*d*), the variation of the amplitude of the signal under measurement resulting from the environmental temperature varying from T1 to T2 is $\Delta Vd1T$. In this case, the error $\Delta Vd1$ in the amplitude of the signal under measurement is the sum of $\Delta Vd1b + \Delta Vd1m + \Delta Vd1s + \Delta Vd1T$.

For example, the amplitude error derivation unit 417 derives an error in the amplitude of the signal under measurement between the measurement amplitude variation factor at a point in time when the signal under measurement has been measured at the second time (reference amplitude variation factors: Vb2', MP2, SP2 and T2) and the measurement amplitude variation factor at the time when the signal under measurement has been measured at the third time (Vb3, MP3, SP3 and T3), however, with the bias voltage Vb2' being the one that causes the bias voltage Vb2 to vary from Vb2 to Vb2' for the correction of the amplitude error.

Referring to FIG. 33(*a*), the variation of the amplitude of the signal under measurement resulting from the bias voltage varying from Vb2' to Vb3 is $\Delta Vd2b$. Referring to FIG. 33(*b*), the variation of the amplitude of the signal under measurement resulting from the power of the master laser light pulse varying from MP2 to MP3 is $\Delta Vd2m$. Referring to FIG. 33(*c*), the variation of the amplitude of the signal under measurement resulting from the power of the slave laser light pulse varying from SP2 to SP3 is $\Delta Vd2s$. Referring to FIG. 33(*d*), the variation of the amplitude of the signal under measurement resulting from the environmental temperature varying from T2 to T3 is $\Delta Vd2T$. In this case, the error in the amplitude of the signal under measurement, $\Delta Vd2$ is the sum of $\Delta Vd2b + \Delta Vd2m + \Delta Vd2s + \Delta Vd2T$.

Based on information recorded by the device and bias amplitude characteristic recording unit 420, the correction value derivation unit 426 derives the correction values $\Delta Vb1$, $\Delta Vb2$ of the bias voltage required to vary the amplitude of the signal under measurement by values that cancel the errors $\Delta Vd1$, $\Delta Vd2$ of the amplitude of the signal under measurement, the error being derived by the amplitude error derivation unit 417.

Figure 34:
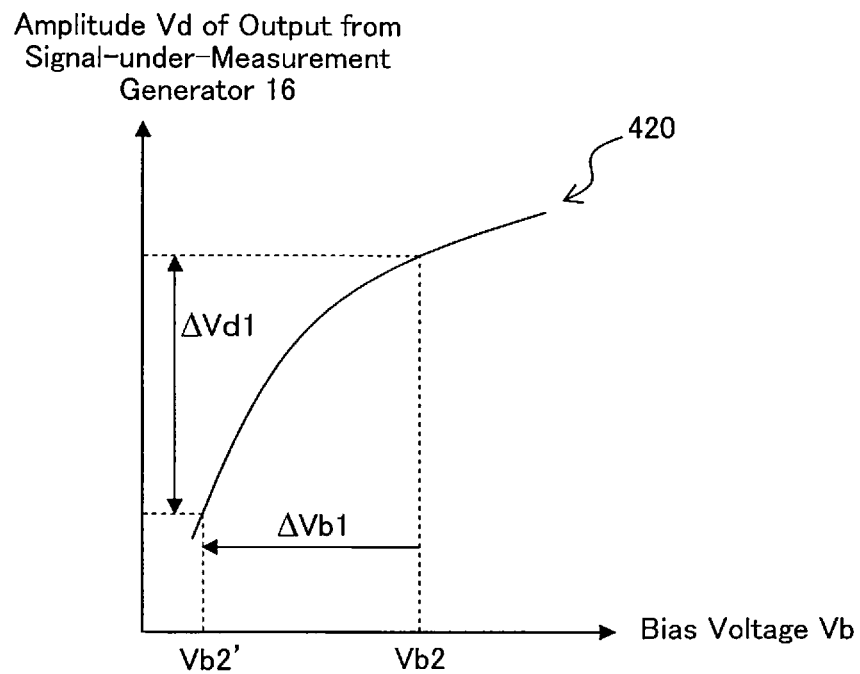
FIG. 34 is a graph illustrating derivation of the correction values of the bias voltage by the correction value derivation unit 426.

FIG. 34 is a graph illustrating derivation of the correction values of the bias voltage by the correction value derivation unit 426. The solid line curve in FIG. 34 represents information (refer to FIG. 27) recorded by the device and bias amplitude characteristic recording unit 420.

The amplitude error of the signal under measurement, $\Delta Vd1$ (>0) is the sum of $\Delta Vd1b+\Delta Vd1m+\Delta Vd1s+\Delta Vd1T$, as described above. The bias voltage at this time is Vb2. In order to cancel (reduce) the amplitude error $\Delta Vd1$, it will suffice if the bias voltage is reduced from Vb2 to Vb2'. The bias voltage Vb2' is a bias voltage that corresponds to a value resulting from the amplitude error $\Delta Vd1$ being reduced from the amplitude of output from the signal-under-measurement generator unit 16, the amplitude corresponding to the bias voltage Vb2. The correction value $\Delta Vb1$ of the bias voltage is Vb2'−Vb2.

The bias voltage applying unit (amplitude error correction unit) 50 causes the bias voltage that is applied to the illumination light pulse generator 14 to vary by the correction value $\Delta Vb$ of the bias voltage derived by the correction value derivation unit 426. Note that the correction value derivation unit 426 has derived the correction value $\Delta Vb$ of the bias voltage, based on the error $\Delta Vd$ of the amplitude of the signal under measurement derived by the amplitude error derivation unit 417. Thus, the bias voltage applying unit 50 corrects the amplitude of the signal under measurement, based on the result derived by the amplitude error derivation unit 417.

The operation of the eighth embodiment will next be described.

Figure 32:
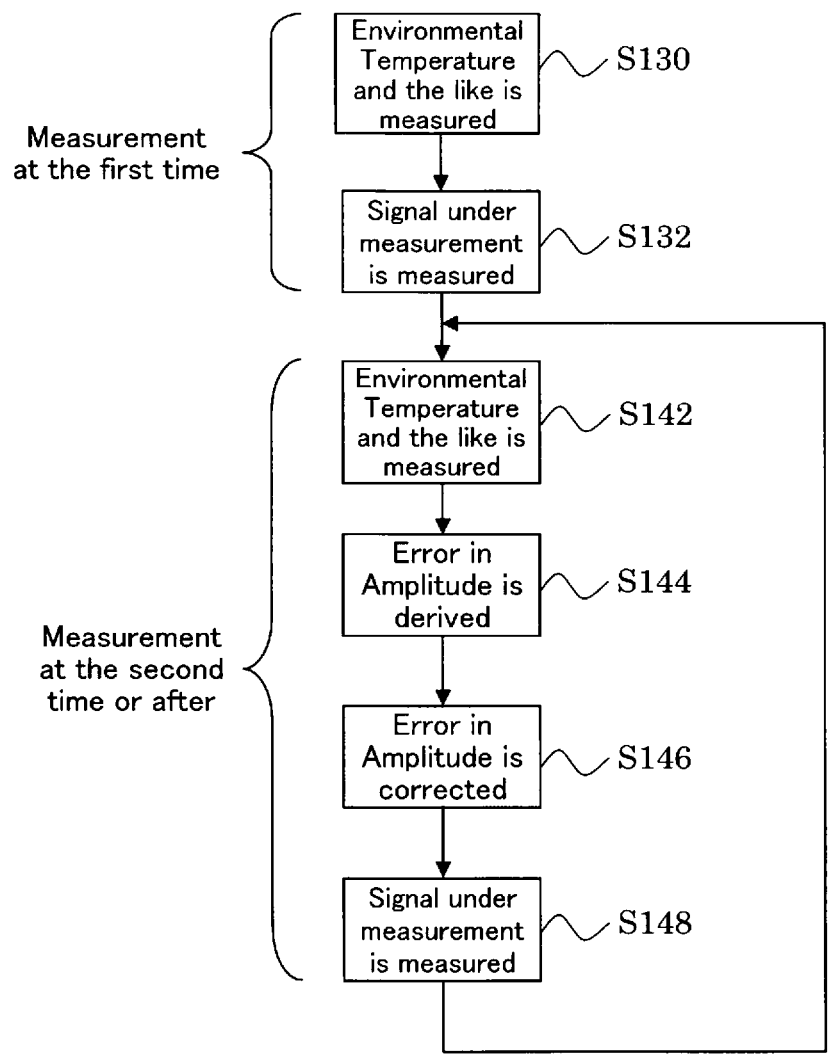
FIG. 32 is a flow chart showing the operation of the eighth embodiment.

FIG. 32 is a flow chart showing the operation of the eighth embodiment.

A master laser light pulse generated as an output from the master laser 11 is provided via the half mirror M11 to the illumination light pulse generator 14. An illumination light pulse is generated as an output from the illumination light pulse generator 14. The illumination light pulse passes through the object under measurement 2, and then becomes a light pulse under measurement, which is provided to the signal-under-measurement generator 16.

Moreover, a slave laser light pulse generated as an output from the slave laser 12 is provided via the half mirror M12 to the signal-under-measurement generator 16.

A signal under measurement (which is a current signal) is generated as an output from the signal-under-measurement generator 16 and is converted, while being amplified by the I/V amplifier 28, into a voltage signal, which is provided to the waveform display device 40.

Note that the master laser light pulse and the slave laser light pulse are reflected from the half mirrors M11, M12 and then provided to the trigger signal generator 32.

The trigger signal generator 32 generates an output trigger signal at a point in time when simultaneously receiving a master laser light pulse and a slave laser light pulse. Note that the trigger signal is provided to the waveform display device 40.

Here, the thermometer 41 measures the environmental temperature T1 (S130: measurement at the first time). Note that the measurement of the amplitude variation factor is made other than the environmental temperatures. The environmental temperature T1 measured is provided to the amplitude error derivation unit 417. Simultaneously with this operation, the power MP1 of the master laser light pulse and the power SP1 of the slave laser light pulse, each measured by the optical power measuring device 52, and the bias voltage Vb1 measured by the bias voltage applying unit 50, are provided to the amplitude error derivation unit 417.

Further, the signal measuring unit 42 measures an output point (e.g., output start point) of a signal under measurement relative to a trigger signal, and the amplitude of the signal under measurement (S132: measurement at the first time).

After a certain period of time has elapsed after the signal under measurement has been measured (S132: measurement at the first time), the thermometer 41 measures the environmental temperature T2 (S142: measurement at the second time). Note that the measurement of the amplitude variation factor is made other than the environmental temperatures. The environmental temperature T2 measured is provided to the amplitude error derivation unit 417. Simultaneously with this operation, the power MP2 of the master laser light pulse and the power SP2 of the slave laser light pulse, each measured by the optical power measuring device 52, and the bias voltage Vb2 measured by the bias voltage applying unit 50, are provided to the amplitude error derivation unit 417.

Here, based on the information recorded by the device amplitude characteristic recording unit 422, the amplitude error derivation unit 417 derives an error $\Delta Vd1$ in the amplitude of the signal under measurement between the measurement amplitude variation factor at a point in time when the signal under measurement has been measured at the first time (reference amplitude variation factors: Vb1, MP1, SP1 and T1) and the measurement amplitude variation factor at the time when the signal under measurement has been measured at the second time (Vb2, MP2, SP2 and T2) (S144: measurement at the second time). Note that, referring to FIG. 33, the value $\Delta Vd1$ is the sum of $\Delta Vd1b+\Delta Vd1m+\Delta Vd1s+\Delta Vd1T$.

Based on the information (refer to FIG. 27) recorded by the device and bias amplitude characteristic recording unit 420, the correction value derivation 426 derives (refer to FIG. 34) the correction value $\Delta Vb1$ of the bias voltage required to vary the amplitude of the signal under measurement by a value that cancels the error $\Delta Vd1$ of amplitude of the signal under measurement, the error being derived by the amplitude error derivation unit 417. The correction value $\Delta Vb1$ of the bias voltage is provided to the bias voltage applying unit 50. The bias voltage applying unit 50 varies by the correction value $\Delta Vb1$ of the bias voltage the bias voltage Vb2 that is applied to the illumination light pulse generator 14, to thereby change the voltage to Vb2' (=Vb2+$\Delta Vb1$), and then reduces the amplitude of the signal under measurement by the amplitude error $\Delta Vd1$, to correct the amplitude error of the signal under measurement (S146: measurement at the second time).

Thereafter, the signal measuring unit 42 measures the output point (e.g., output start point) of the signal under measurement relative to the trigger signal, and the amplitude of the signal under measurement (S148: measurement at the second time).

After a certain period of time has elapsed after the signal under measurement has been measured (S148: measurement at the second time), the thermometer 41 measures the environmental temperature T3 (S142: measurement at the third time). Note that the measurement of the amplitude variation factor is made other than the environmental temperatures. The environmental temperature T3 measured is provided to the amplitude error derivation unit 417. Simultaneously with this operation, the power MP3 of the master laser light pulse and the power SP3 of the slave laser light pulse, each measured by the optical power measuring device 52, and the bias voltage Vb3 measured by the bias voltage applying unit 50, are provided to the amplitude error derivation unit 417.

Here, based on the information recorded by the device amplitude characteristic recording unit 422, the amplitude error derivation unit 417 derives an error $\Delta Vd2$ of the amplitude of the signal under measurement between the measurement amplitude variation factor at a point in time when the signal under measurement has been measured at the second time (reference amplitude variation factors: Vb2', MP2, SP2 and T2) and the measurement amplitude variation factor at the time when the signal under measurement has been measured at the third time (Vb3, MP3, SP3 and T3) (S144: measurement at the third time). Note that referring to FIG. 33, the value ΔVd2 is the sum of ΔVd2$b$+ΔVd2$m$+ΔVd2$s$+ΔVd2T.

Based on information (refer to FIG. 27) recorded by the device and bias amplitude characteristic recording unit 420, the correction value derivation 426 derives the correction value ΔVb2 of the bias voltage required to vary the amplitude of the signal under measurement by a value that cancels the error ΔVd2 of the amplitude of the signal under measurement, the error being derived by the amplitude error derivation unit 417. The method of deriving the correction value ΔVb2 of the bias voltage is the same as that of deriving the value ΔVb1 (refer to FIG. 34). The correction value ΔVb2 of the bias voltage is provided to the bias voltage applying unit 50. The bias voltage applying unit 50 varies by the correction value ΔVb2 of the bias voltage the bias voltage Vb3 that is applied to the illumination light pulse generator 14, to thereby change the voltage to Vb3' Vb3+ ΔVb2), and then reduces the amplitude of the signal under measurement by the amplitude error ΔVd2 to thereby correct the amplitude error of the signal under measurement (S146: measurement at the third time).

Thereafter, the signal measuring unit 42 measures the output point (e.g., output start point) of the signal under measurement relative to the trigger signal, and the amplitude of the signal under measurement (S148: measurement at the third time).

According to the eighth embodiment, the amplitude error derivation unit 417 presumes from the amplitude variation factor an error of the measurement result (output point) of the object under measurement 2 by means of light, such as terahertz light (illumination light pulse), the error resulting from the changed amplitude variation factor of the ambient temperature (environmental temperature) and the like of the light measurement apparatus 1, and then the bias voltage applying unit 50 corrects the error; as a result, the amplitude of the signal under measurement can be obtained correctly.

Figure 35:
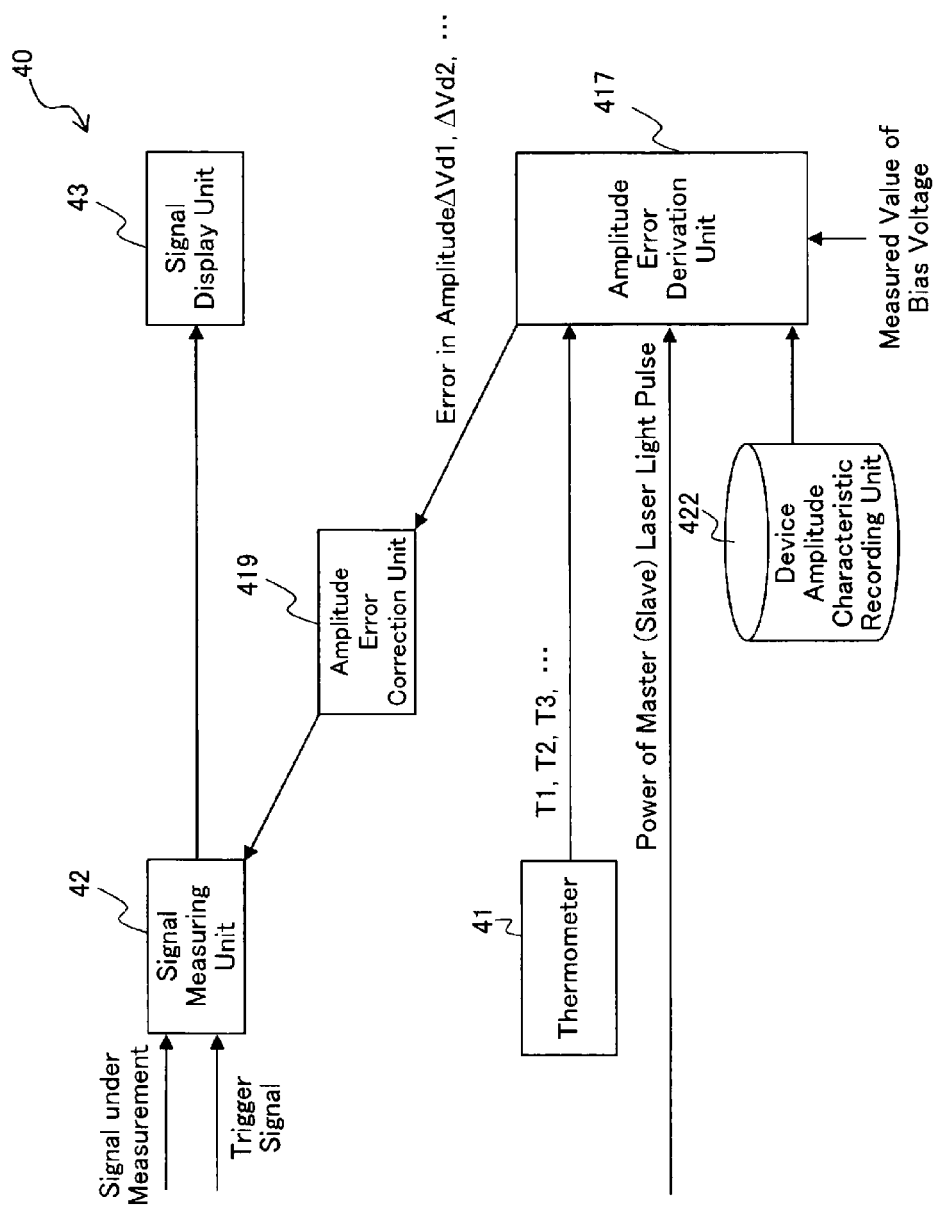
FIG. 35 is a functional block diagram of a configuration of the waveform display device 40 according to a modification (where correction of the amplitude error is made independent of the bias voltage) of the eighth embodiment.

Note that although in the eighth embodiment the amplitude error is corrected by causing the bias voltage applying unit 50 to vary the bias voltage, the correction of the amplitude error can be made independent of variation in the bias voltage. FIG. 35 is a functional block diagram of a configuration of the waveform display device 40 according to a modification (where correction of the amplitude error is made independent of the bias voltage) of the eighth embodiment.

The waveform display device 40 according to the modification of the eighth embodiment is configured such that the device and bias amplitude characteristic recording unit 420, and the correction value derivation unit 426 are deleted from the waveform display device 40 according to the eighth embodiment and then the amplitude error correction unit 419 is added to the waveform display device 40.

The amplitude error derivation unit 417 in the waveform display device 40 according to the modification of the eighth embodiment provides the derived amplitude errors ΔVd1, ΔVd2, . . . not to the bias voltage applying unit 50, but to the amplitude error correction unit 419. The amplitude error correction unit 419 provides the amplitude errors ΔVd1, ΔVd2, . . . to the signal measuring unit 42, where the amplitude of the signal under measurement is shifted by −ΔVd1, −ΔVd2, . . . , to cancel the amplitude errors ΔVd1, ΔVd2, . . . . Note that if the signal measuring unit 42 is assumed to be the one that generate the output measurement result as digital data, the signal measuring unit 42 generates as an output the data of amplitude in the digital data by varying the data by −ΔVd1, −ΔVd2, . . . . In this way, the measurement result obtained by the signal measuring unit 42 is corrected.

Further, the above embodiments can be achieved as below. A computer with a CPU, a hard disk, and a media (floppy (trademark) disk, CD-ROM, etc.) reader is adapted to read media that store therein programs for achieving the above described components, e.g., each part of the waveform display device 40. Then, the media read are installed in the hard disk. Even this method can achieve the above described functions.

The invention claimed is:

1. A light measurement apparatus that corrects an error in a measurement of a signal under measurement, the apparatus comprising:
    a master laser that generates as an output a master laser light pulse;
    a slave laser that generates as an output a slave laser light pulse having a repetition frequency or a phase different from that of the master laser light pulse;
    an illumination light pulse generator that receives the master laser light pulse and generates as an output an illumination light pulse; and
    a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement;
    wherein the apparatus corrects an error in measurement at an output point of the signal under measurement;
    wherein the apparatus further comprises:
        a signal measuring unit that measures the output point of the signal under measurement;
        a monitor signal generator that receives the illumination light pulse and the slave laser light pulse and generates as an output a monitor signal;
        a time measuring unit that measures an output point of the monitor signal;
        a time difference derivation unit that derives a lag between a measurement result obtained by the time measuring unit and a measurement result obtained by the time measuring unit before a point in time when the former measurement result is obtained; and
        an error correction unit that corrects the output point of the signal under measurement, based on a result derived by the time difference derivation unit, and
    wherein a difference in time between the signal under measurement and the monitor signal is constant.

2. The light measurement apparatus according to claim 1, further comprising a trigger signal generator that generates as an output a trigger signal at a point in time when simultaneously receiving the master laser light pulse and the slave laser light pulse, wherein the signal measuring unit measures the output point of the signal under measurement relative to the trigger signal, and wherein the error correction unit corrects an output point of the trigger signal generated from the trigger signal generator.

3. The light measurement apparatus according to claim 1, wherein the error correction unit corrects the measurement result obtained by the signal measuring unit.

4. The light measurement apparatus according to claim 1, wherein the time measuring unit measures the monitor signal at a plurality times, and wherein the time difference derivation unit derives the lag between the measurement result obtained by the time measuring unit and the measurement result obtained at the last time by the time measuring unit.

5. The light measurement apparatus according to claim 4, wherein the time difference derivation unit derives a lag between the measurement result obtained by the time measuring unit and the measurement result obtained at the last time by the time measuring unit, the latter result being a result that has been corrected by the error correction unit.

6. The light measurement apparatus according to claim 1, wherein the signal-under-measurement generator doubles as the monitor signal generator, and wherein the light pulse under measurement and the illumination light pulse are received by the signal-under-measurement generator in such a way that both pulses do not overlap with each other in a time domain.

7. The light measurement apparatus according to claim 6, wherein the difference in optical path between an optical path where the object under measurement is present and an optical path where the object under measurement is not present, each path being located between the illumination light pulse generator and the signal-under-measurement generator, is great enough for the signal-under-measurement generator to receive the light pulse under measurement and the illumination light pulse in such a way that both pulses do not overlap with each other in the time domain.

8. The light measurement apparatus according to claim 6, comprising an optical system in which any selected one of the light pulse under measurement and the illumination light pulse is provided to the signal-under-measurement generator.

9. A method of measuring light with using a light measurement apparatus including:
  a master laser that generates as an output a master laser light pulse;
  a slave laser that generates as an output a slave laser light pulse having a repetition frequency or a phase different from that of the master laser light pulse;
  an illumination light pulse generator that receives the master laser light pulse and generates as an output an illumination light pulse;
  and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement, said method comprising:
  a correcting step that corrects an error in a measurement of a signal under measurement
  wherein the apparatus corrects an error in measurement at an output point of the signal under measurement;
  wherein the apparatus further comprises:
    a signal measuring unit that measures the output point of the signal under measurement;
    a monitor signal generator that receives the illumination light pulse and the slave laser light pulse and generates as an output a monitor signal;
    a time measuring unit that measures an output point of the monitor signal;
    a time difference derivation unit that derives a lag between a measurement result obtained by the time measuring unit and a measurement result obtained by the time measuring unit before a point in time when the former measurement result is obtained;
    and an error correction unit that corrects the output point of the signal under measurement, based on a result derived by the time difference derivation unit, and
  wherein a difference in time between the signal under measurement and the monitor signal is constant.

10. A non-transitory computer-readable medium having a program of instructions for execution by a computer to perform a process for measuring light with using a light measurement apparatus including:
  a master laser that generates as an output a master laser light pulse;
  a slave laser that generates as an output a slave laser light pulse having a repetition frequency or a phase different from that of the master laser light pulse;
  an illumination light pulse generator that receives the master laser light pulse and generates as an output an illumination light pulse;
  and a signal-under-measurement generator that, at a point in time when receiving a light pulse under measurement obtained by illuminating the object under measurement with the illumination light pulse and further the slave laser light pulse, generates as an output the signal under measurement according to a power of the light pulse under measurement, said process comprising:
  a correcting step that corrects an error in a measurement of a signal under measurement;
  wherein the apparatus corrects an error in measurement at an output point of the signal under measurement;
  wherein the apparatus further comprises:
    a signal measuring unit that measures the output point of the signal under measurement;
    a monitor signal generator that receives the illumination light pulse and the slave laser light pulse and generates as an output a monitor signal;
    a time measuring unit that measures an output point of the monitor signal;
    a time difference derivation unit that derives a lag between a measurement result obtained by the time measuring unit and a measurement result obtained by the time measuring unit before a point in time when the former measurement result is obtained; and
  an error correction unit that corrects the output point of the signal under measurement, based on a result derived by the time difference derivation unit, and
  wherein a difference in time between the signal under measurement and the monitor signal is constant.

* * * * *